(12) United States Patent
Wu et al.

(10) Patent No.: US 9,706,957 B2
(45) Date of Patent: *Jul. 18, 2017

(54) SLEEP STAGE DETECTION

(71) Applicant: Medtronic, Inc., Minneapolis, MN (US)

(72) Inventors: Jianping Wu, Shoreview, MN (US); Gregory F. Molnar, Blaine, MN (US); Gabriela C. Molnar, Blaine, MN (US); Timothy J. Denison, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/733,349

(22) Filed: Jun. 8, 2015

(65) Prior Publication Data

US 2015/0265207 A1 Sep. 24, 2015

Related U.S. Application Data

(63) Continuation of application No. 12/238,105, filed on Sep. 25, 2008, now Pat. No. 9,072,870.

(Continued)

(51) Int. Cl.
*A61N 1/00* (2006.01)
*A61N 1/08* (2006.01)
(Continued)

(52) U.S. Cl.
CPC .......... *A61B 5/4812* (2013.01); *A61B 5/0031* (2013.01); *A61B 5/02055* (2013.01);
(Continued)

(58) Field of Classification Search
CPC ............ A61B 5/36067; A61B 5/36078; A61B 5/36082; A61B 5/36096
(Continued)

(56) References Cited

U.S. PATENT DOCUMENTS 1,342,885 A 6/1920 Armstrong
3,130,373 A 4/1964 Braymer
(Continued)

FOREIGN PATENT DOCUMENTS

CN 86102707 A 11/1986
CN 86102810 A 11/1986
(Continued)

OTHER PUBLICATIONS

Notice on Reexamination, and translation thereof, from counterpart Chinese Application No. 200880125611.1, dated Mar. 14, 2016, 17 pp.

(Continued)

*Primary Examiner* — Allen Porter, Jr.
(74) *Attorney, Agent, or Firm* — Shumaker & Sieffert, P.A.

(57) ABSTRACT

Therapy delivery to a patient may be controlled based on a determined sleep stage of the patient. In examples, the sleep stage may be determined based on a frequency characteristic of a biosignal indicative of brain activity of the patient. A frequency characteristic may include, for example, a power level within one or more frequency bands of the biosignal, a ratio of the power level in two or more frequency bands, or a pattern in the power level of one or more frequency bands over time. A therapy program may be selected or modified based on the sleep stage determination. Therapy may be delivered during the sleep stage according to the selected or modified therapy program. In some examples, therapy delivery may be controlled after making separate determinations of a sleep stage based on the biosignal and another physiological parameter, and confirming that the sleep stage determinations are consistent.

36 Claims, 19 Drawing Sheets

Related U.S. Application Data

(60) Provisional application No. 61/049,166, filed on Apr. 30, 2008, provisional application No. 61/023,522, filed on Jan. 25, 2008.

(51) Int. Cl.

| | | |
|---|---|---|
| *A61B 5/00* | (2006.01) | |
| *A61B 5/04* | (2006.01) | |
| *A61B 5/048* | (2006.01) | |
| *A61M 21/02* | (2006.01) | |
| *A61B 5/0205* | (2006.01) | |
| *A61B 5/0402* | (2006.01) | |
| *A61B 5/0478* | (2006.01) | |
| *A61B 5/11* | (2006.01) | |
| *A61M 5/172* | (2006.01) | |
| *A61N 1/36* | (2006.01) | |
| *A61M 21/00* | (2006.01) | |
| *G06F 19/00* | (2011.01) | |
| *A61B 5/01* | (2006.01) | |
| *A61B 5/024* | (2006.01) | |

(52) U.S. Cl.
CPC ............ *A61B 5/0402* (2013.01); *A61B 5/048* (2013.01); *A61B 5/04014* (2013.01); *A61B 5/04015* (2013.01); *A61B 5/0478* (2013.01); *A61B 5/1116* (2013.01); *A61B 5/1118* (2013.01); *A61B 5/4839* (2013.01); *A61M 5/1723* (2013.01); *A61M 21/02* (2013.01); *A61N 1/36078* (2013.01); *A61N 1/36139* (2013.01); *A61B 5/01* (2013.01); *A61B 5/024* (2013.01); *A61B 5/4082* (2013.01); *A61M 2005/1726* (2013.01); *A61M 2021/0072* (2013.01); *A61M 2205/3523* (2013.01); *A61M 2205/3553* (2013.01); *A61M 2205/3584* (2013.01); *A61M 2205/3592* (2013.01); *A61M 2205/50* (2013.01); *A61M 2205/52* (2013.01); *A61M 2230/005* (2013.01); *A61M 2230/04* (2013.01); *A61M 2230/08* (2013.01); *A61M 2230/10* (2013.01); *A61M 2230/205* (2013.01); *A61M 2230/30* (2013.01); *A61M 2230/42* (2013.01); *A61M 2230/50* (2013.01); *A61M 2230/60* (2013.01); *A61M 2230/63* (2013.01); *A61M 2230/65* (2013.01); *G06F 19/3406* (2013.01); *G06F 19/3481* (2013.01)

(58) Field of Classification Search
USPC .......................................................... 607/45
See application file for complete search history.

(56) References Cited

U.S. PATENT DOCUMENTS

| | | |
|---|---|---|
| 3,603,997 A | 9/1971 | Brouwer et al. |
| 3,780,725 A | 12/1973 | Goldberg |
| 4,013,068 A | 3/1977 | Settle et al. |
| 4,138,649 A | 2/1979 | Schaffer |
| 4,177,819 A | 12/1979 | Kofsky et al. |
| 4,188,586 A | 2/1980 | Egami |
| 4,279,258 A | 7/1981 | John |
| 4,579,125 A | 4/1986 | Strobl et al. |
| 4,610,259 A | 9/1986 | Cohen et al. |
| 4,612,934 A | 9/1986 | Borkan |
| 4,733,667 A | 3/1988 | Olive et al. |
| 4,776,345 A | 10/1988 | Cohen et al. |
| 4,933,642 A | 6/1990 | Lee |
| 4,979,230 A | 12/1990 | Marz |
| 5,024,221 A | 6/1991 | Morgan |
| 5,061,593 A | 10/1991 | Yoerger et al. |
| 5,105,167 A | 4/1992 | Peczalski |
| 5,113,143 A | 5/1992 | Wei |
| 5,154,180 A | 10/1992 | Blanchet et al. |
| 5,179,947 A | 1/1993 | Meyerson et al. |
| 5,205,285 A | 4/1993 | Baker, Jr. |
| 5,206,602 A | 4/1993 | Baumgartner et al. |
| 5,215,086 A | 6/1993 | Terry, Jr. et al. |
| 5,282,840 A | 2/1994 | Hudrlik |
| 5,293,879 A | 3/1994 | Vonk et al. |
| 5,299,569 A | 4/1994 | Wernicke et al. |
| 5,311,876 A | 5/1994 | Olsen et al. |
| 5,334,222 A | 8/1994 | Salo et al. |
| 5,335,657 A | 8/1994 | Terry, Jr. et al. |
| 5,458,117 A | 10/1995 | Chamoun et al. |
| 5,477,481 A | 12/1995 | Kerth |
| 5,489,759 A | 2/1996 | Litt et al. |
| 5,619,536 A | 4/1997 | Gourgue |
| 5,663,680 A | 9/1997 | Nordeng |
| 5,716,377 A | 2/1998 | Rise et al. |
| 5,725,558 A | 3/1998 | Warnke |
| 5,769,877 A | 6/1998 | Barreras, Sr. |
| 5,782,884 A | 7/1998 | Stotts et al. |
| 5,833,709 A | 11/1998 | Rise et al. |
| 5,840,040 A | 11/1998 | Altschuler et al. |
| 5,843,139 A | 12/1998 | Goedeke et al. |
| 5,928,272 A | 7/1999 | Adkins et al. |
| 5,995,868 A | 11/1999 | Dorfmeister et al. |
| 6,011,990 A | 1/2000 | Schultz et al. |
| 6,018,682 A | 1/2000 | Rise |
| 6,024,700 A | 2/2000 | Nemirovski et al. |
| 6,061,593 A | 5/2000 | Fischell et al. |
| 6,064,257 A | 5/2000 | Sauer |
| 6,066,163 A | 5/2000 | John |
| 6,070,101 A | 5/2000 | Struble et al. |
| 6,094,598 A | 7/2000 | Elsberry et al. |
| 6,129,681 A | 10/2000 | Kuroda et al. |
| 6,130,578 A | 10/2000 | Tang |
| 6,157,857 A | 12/2000 | Dimpfel |
| 6,161,042 A | 12/2000 | Hartley et al. |
| 6,214,016 B1 | 4/2001 | Williams et al. |
| 6,262,626 B1 | 7/2001 | Bakker et al. |
| 6,272,378 B1 | 8/2001 | Baumgart-Schmitt |
| 6,287,263 B1 | 9/2001 | Briskin |
| 6,315,740 B1 | 11/2001 | Singh |
| 6,331,160 B1 | 12/2001 | Bardy |
| 6,353,762 B1 | 3/2002 | Baudino et al. |
| 6,356,784 B1 | 3/2002 | Lozano et al. |
| 6,360,123 B1 | 3/2002 | Kimchi et al. |
| 6,366,813 B1 | 4/2002 | DiLorenzo |
| 6,456,159 B1 | 9/2002 | Brewer |
| 6,459,936 B2 | 10/2002 | Fischell et al. |
| 6,463,328 B1 | 10/2002 | John |
| 6,468,234 B1 | 10/2002 | Van der Loos et al. |
| 6,483,355 B1 | 11/2002 | Lee et al. |
| 6,522,914 B1 | 2/2003 | Huvelle et al. |
| 6,539,261 B2 | 3/2003 | Dal Molin |
| 6,584,351 B1 | 6/2003 | Ekwall |
| 6,597,953 B2 | 7/2003 | Boling |
| 6,605,038 B1 | 8/2003 | Teller et al. |
| 6,617,838 B1 | 9/2003 | Miranda et al. |
| 6,625,436 B1 | 9/2003 | Tolson et al. |
| 6,658,287 B1 | 12/2003 | Litt et al. |
| 6,667,760 B1 | 12/2003 | Limberg |
| 6,674,322 B2 | 1/2004 | Motz |
| 6,725,091 B2 | 4/2004 | Dal Molin |
| 6,754,535 B2 | 6/2004 | Noren et al. |
| 6,810,285 B2 | 10/2004 | Pless et al. |
| 6,819,956 B2 | 11/2004 | DiLorenzo |
| 6,839,594 B2 | 1/2005 | Cohen et al. |
| 6,876,842 B2 | 4/2005 | Davie |
| 6,904,321 B1 | 6/2005 | Bornzin et al. |
| 6,914,539 B2 | 7/2005 | Hoctor et al. |
| 6,954,524 B2 | 10/2005 | Gibson et al. |
| 6,993,380 B1 | 1/2006 | Modarres |
| 7,006,872 B2 | 2/2006 | Gielen et al. |
| 7,010,347 B2 | 3/2006 | Schecter |
| 7,098,823 B2 | 8/2006 | O'Dowd et al. |
| 7,110,820 B2 | 9/2006 | Tcheng et al. |
| 7,120,486 B2 | 10/2006 | Leuthardt et al. |
| 7,142,917 B2 | 11/2006 | Fukui |

(56) References Cited

U.S. PATENT DOCUMENTS

| | | |
|---|---|---|
| 7,146,208 B2 | 12/2006 | Holmstrom et al. |
| 7,146,218 B2 | 12/2006 | Esteller et al. |
| 7,151,961 B1 | 12/2006 | Whitehurst et al. |
| 7,171,258 B2 | 1/2007 | Goode |
| 7,177,609 B1 | 2/2007 | Wong |
| 7,209,788 B2 | 4/2007 | Nicolelis et al. |
| 7,233,198 B2 | 6/2007 | Niederkorn |
| 7,239,927 B2 | 7/2007 | Ganion |
| 7,299,088 B1 | 11/2007 | Thakor et al. |
| 7,376,463 B2 | 5/2008 | Salo et al. |
| 7,385,443 B1 | 6/2008 | Denison |
| 7,391,257 B1 | 6/2008 | Denison et al. |
| 7,491,181 B2 | 2/2009 | Heruth et al. |
| 7,519,431 B2 | 4/2009 | Goetz et al. |
| 7,595,648 B2 | 9/2009 | Ungaretti et al. |
| 7,622,988 B2 | 11/2009 | Denison et al. |
| 7,671,672 B2 | 3/2010 | McConnell |
| 7,684,867 B2 | 3/2010 | Jaax et al. |
| 7,769,464 B2 | 8/2010 | Gerber et al. |
| 7,813,802 B2 | 10/2010 | Tcheng et al. |
| 7,826,894 B2 | 11/2010 | Musallam et al. |
| 7,847,628 B2 | 12/2010 | Denison |
| 7,957,814 B2 | 6/2011 | Goetz et al. |
| 7,974,703 B2 | 7/2011 | Goetz et al. |
| 8,032,229 B2 | 10/2011 | Gerber et al. |
| 8,121,694 B2 | 2/2012 | Molnar et al. |
| 8,290,596 B2 | 10/2012 | Wei et al. |
| 8,380,314 B2 | 2/2013 | Panken et al. |
| 8,554,325 B2 | 10/2013 | Molnar et al. |
| 8,738,145 B2 | 5/2014 | Goetz et al. |
| 8,751,007 B2 | 6/2014 | Goetz et al. |
| 9,072,870 B2 | 7/2015 | Wu et al. |
| 2002/0002390 A1 | 1/2002 | Fischell et al. |
| 2002/0017782 A1 | 2/2002 | Patton et al. |
| 2002/0038137 A1 | 3/2002 | Stein |
| 2002/0091332 A1 | 7/2002 | Bombardini |
| 2002/0103512 A1 | 8/2002 | Echauz et al. |
| 2002/0177882 A1 | 11/2002 | DiLorenzo |
| 2003/0046254 A1 | 3/2003 | Ryu et al. |
| 2003/0105409 A1 | 6/2003 | Donoghue et al. |
| 2003/0146786 A1 | 8/2003 | Gulati et al. |
| 2003/0149457 A1 | 8/2003 | Tcheng et al. |
| 2003/0158587 A1 | 8/2003 | Esteller et al. |
| 2003/0171791 A1 | 9/2003 | KenKnight et al. |
| 2004/0002635 A1 | 1/2004 | Hargrove et al. |
| 2004/0015211 A1 | 1/2004 | Nurmikko et al. |
| 2004/0077967 A1 | 4/2004 | Jordan |
| 2004/0077987 A1 | 4/2004 | Rapacki et al. |
| 2004/0082875 A1 | 4/2004 | Donoghue et al. |
| 2004/0122483 A1 | 6/2004 | Nathan et al. |
| 2004/0138516 A1* | 7/2004 | Osorio ............... A61N 1/36132 600/9 |
| 2004/0141558 A1 | 7/2004 | Plisch et al. |
| 2004/0158119 A1 | 8/2004 | Osorio et al. |
| 2004/0167418 A1 | 8/2004 | Nguyen et al. |
| 2004/0176809 A1 | 9/2004 | Cho et al. |
| 2004/0215286 A1 | 10/2004 | Stypulkowski |
| 2004/0249302 A1 | 12/2004 | Donoghue et al. |
| 2004/0249422 A1 | 12/2004 | Gliner et al. |
| 2005/0007091 A1 | 1/2005 | Makeig et al. |
| 2005/0033376 A1* | 2/2005 | Whitehurst ....... A61M 5/14276 607/45 |
| 2005/0043652 A1 | 2/2005 | Lovett et al. |
| 2005/0065427 A1 | 3/2005 | Magill et al. |
| 2005/0080461 A1* | 4/2005 | Stahmann ............. A61B 5/0031 607/17 |
| 2005/0081847 A1 | 4/2005 | Lee et al. |
| 2005/0107838 A1* | 5/2005 | Lovett ................ A61B 5/02055 607/17 |
| 2005/0113744 A1 | 5/2005 | Donoghue et al. |
| 2005/0118968 A1 | 6/2005 | Cowley |
| 2005/0143589 A1 | 6/2005 | Donoghue et al. |
| 2005/0182447 A1 | 8/2005 | Schecter |
| 2005/0197588 A1 | 9/2005 | Freeberg |
| 2005/0203366 A1 | 9/2005 | Donoghue et al. |
| 2005/0209511 A1 | 9/2005 | Heruth et al. |
| 2005/0209512 A1 | 9/2005 | Heruth et al. |
| 2005/0209644 A1 | 9/2005 | Heruth et al. |
| 2005/0216064 A1 | 9/2005 | Heruth et al. |
| 2005/0240242 A1 | 10/2005 | DiLorenzo |
| 2005/0246003 A1 | 11/2005 | Black et al. |
| 2005/0282517 A1 | 12/2005 | Cowley |
| 2006/0041221 A1 | 2/2006 | Stypulkowski |
| 2006/0049957 A1 | 3/2006 | Surgenor et al. |
| 2006/0055456 A1 | 3/2006 | Niederkorn |
| 2006/0058627 A1 | 3/2006 | Flaherty et al. |
| 2006/0106275 A1 | 5/2006 | Raniere |
| 2006/0116591 A1 | 6/2006 | Cooper |
| 2006/0133550 A1 | 6/2006 | Bolton et al. |
| 2006/0135877 A1 | 6/2006 | Giftakis et al. |
| 2006/0135879 A1 | 6/2006 | Liley |
| 2006/0139192 A1 | 6/2006 | Morrow et al. |
| 2006/0139193 A1 | 6/2006 | Morrow et al. |
| 2006/0149338 A1 | 7/2006 | Flaherty et al. |
| 2006/0161219 A1 | 7/2006 | Mock et al. |
| 2006/0167530 A1 | 7/2006 | Flaherty et al. |
| 2006/0169282 A1 | 8/2006 | Izumi et al. |
| 2006/0173259 A1 | 8/2006 | Flaherty et al. |
| 2006/0173494 A1 | 8/2006 | Armstrong et al. |
| 2006/0173501 A1 | 8/2006 | Stickney et al. |
| 2006/0184060 A1 | 8/2006 | Belalcazar et al. |
| 2006/0189899 A1 | 8/2006 | Flaherty et al. |
| 2006/0206167 A1 | 9/2006 | Flaherty et al. |
| 2006/0206174 A1 | 9/2006 | Honeycutt et al. |
| 2006/0212089 A1 | 9/2006 | Tass |
| 2006/0212090 A1 | 9/2006 | Lozano et al. |
| 2006/0212093 A1 | 9/2006 | Pless et al. |
| 2006/0229687 A1 | 10/2006 | Goetz et al. |
| 2006/0241357 A1 | 10/2006 | Chirife |
| 2006/0253166 A1 | 11/2006 | Flaherty et al. |
| 2006/0253168 A1 | 11/2006 | Wyler et al. |
| 2006/0258930 A1 | 11/2006 | Wu et al. |
| 2006/0259099 A1 | 11/2006 | Goetz et al. |
| 2006/0265022 A1 | 11/2006 | John et al. |
| 2006/0281427 A1 | 12/2006 | Isaac et al. |
| 2006/0293604 A1 | 12/2006 | Carlson et al. |
| 2006/0293720 A1 | 12/2006 | DiLorenzo |
| 2007/0010755 A1 | 1/2007 | Sarkela et al. |
| 2007/0016095 A1 | 1/2007 | Low et al. |
| 2007/0032737 A1 | 2/2007 | Causevic et al. |
| 2007/0032738 A1 | 2/2007 | Flaherty et al. |
| 2007/0032834 A1 | 2/2007 | Gliner et al. |
| 2007/0038265 A1 | 2/2007 | Tcheng et al. |
| 2007/0046486 A1 | 3/2007 | Donoghue et al. |
| 2007/0073355 A1 | 3/2007 | Dilorenzo |
| 2007/0077907 A1 | 4/2007 | Rector |
| 2007/0123758 A1 | 5/2007 | Miesel et al. |
| 2007/0150025 A1 | 6/2007 | Dilorenzo et al. |
| 2007/0179534 A1 | 8/2007 | Firlik et al. |
| 2007/0213785 A1 | 9/2007 | Osorio et al. |
| 2007/0216477 A1 | 9/2007 | McConnell |
| 2007/0249953 A1 | 10/2007 | Frei et al. |
| 2008/0015659 A1 | 1/2008 | Zhang et al. |
| 2008/0051839 A1 | 2/2008 | Libbus et al. |
| 2008/0071314 A1 | 3/2008 | John |
| 2008/0077191 A1 | 3/2008 | Morrell |
| 2008/0154111 A1 | 6/2008 | Wu et al. |
| 2008/0180278 A1 | 7/2008 | Denison |
| 2008/0195166 A1 | 8/2008 | Sun et al. |
| 2008/0243005 A1 | 10/2008 | Jung et al. |
| 2008/0269630 A1 | 10/2008 | Denison et al. |
| 2008/0269631 A1 | 10/2008 | Denison et al. |
| 2008/0269812 A1 | 10/2008 | Gerber et al. |
| 2008/0269841 A1 | 10/2008 | Grevious et al. |
| 2009/0018617 A1 | 1/2009 | Skelton et al. |
| 2009/0082691 A1 | 3/2009 | Denison et al. |
| 2009/0082829 A1 | 3/2009 | Panken et al. |
| 2009/0082831 A1 | 3/2009 | Paul et al. |
| 2009/0099627 A1 | 4/2009 | Molnar et al. |
| 2009/0105785 A1 | 4/2009 | Wei et al. |
| 2009/0118786 A1 | 5/2009 | Meadows et al. |
| 2009/0118787 A1 | 5/2009 | Moffitt et al. |
| 2009/0131995 A1 | 5/2009 | Sloan et al. |
| 2009/0192556 A1 | 7/2009 | Wu et al. |

(56) References Cited

U.S. PATENT DOCUMENTS

| | | | |
|---|---|---|---|
| 2009/0264789 A1 | 10/2009 | Molnar et al. |
| 2010/0033240 A1 | 2/2010 | Denison et al. |
| 2010/0113964 A1 | 5/2010 | Wahlstrand et al. |
| 2010/0114223 A1 | 5/2010 | Wahlstrand et al. |
| 2010/0324442 A1 | 12/2010 | Blomqvist |
| 2010/0327887 A1 | 12/2010 | Denison et al. |
| 2011/0004268 A1 | 1/2011 | Tcheng et al. |
| 2011/0015469 A1 | 1/2011 | Walter et al. |
| 2011/0068861 A1 | 3/2011 | Denison |
| 2011/0112590 A1 | 5/2011 | Wu et al. |
| 2011/0230940 A1 | 9/2011 | Goetz et al. |
| 2012/0053508 A1 | 3/2012 | Wu et al. |
| 2013/0131755 A1 | 5/2013 | Panken et al. |

FOREIGN PATENT DOCUMENTS

| | | |
|---|---|---|
| CN | 2683027 Y | 3/2005 |
| CN | 2754557 Y | 2/2006 |
| CN | 2882531 Y | 3/2007 |
| CN | 101099670 A | 1/2008 |
| DE | 19649991 A1 | 6/1998 |
| EP | 0354060 A2 | 2/1990 |
| EP | 0438945 A1 | 7/1991 |
| EP | 0789449 A2 | 8/1997 |
| EP | 1943944 A1 | 7/2008 |
| EP | 2008581 A2 | 12/2008 |
| GB | 1249395 A | 10/1971 |
| GB | 2447640 A | 9/2008 |
| JP | S4717841 | 10/1972 |
| JP | S5615112 U | 2/1981 |
| JP | H06224659 A | 8/1994 |
| JP | H07120207 A | 5/1995 |
| JP | H10504099 A | 4/1998 |
| JP | 2006279377 A | 10/2006 |
| JP | 2008154681 A | 7/2008 |
| KR | 20010096372 A | 11/2001 |
| RU | 2144310 C1 | 1/2000 |
| WO | WO 97/10747 A1 | 3/1997 |
| WO | WO 00/10455 A1 | 3/2000 |
| WO | WO 02/01711 A1 | 1/2002 |
| WO | WO 02/03087 A1 | 1/2002 |
| WO | WO 02/49500 A2 | 6/2002 |
| WO | WO 02/058536 A2 | 8/2002 |
| WO | WO 03/101532 A2 | 12/2003 |
| WO | WO 2005/001707 A2 | 1/2005 |
| WO | WO 2005/046469 A2 | 5/2005 |
| WO | WO 2005/089641 A1 | 9/2005 |
| WO | WO 2005/089646 A1 | 9/2005 |
| WO | WO 2005/092183 A1 | 10/2005 |
| WO | WO 2006/015002 A1 | 2/2006 |
| WO | WO 2006/020794 A2 | 2/2006 |
| WO | WO 2006/066098 A1 | 6/2006 |
| WO | WO 2006/073915 A2 | 7/2006 |
| WO | WO 2006/074029 A2 | 7/2006 |
| WO | WO 2006/076164 A2 | 7/2006 |
| WO | WO 2006/121455 A1 | 11/2006 |
| WO | WO 2006/126186 A2 | 11/2006 |
| WO | WO 2007/112092 A2 | 10/2007 |
| WO | WO 2008/103078 A1 | 8/2008 |
| WO | WO 2008/105692 A1 | 9/2008 |
| WO | WO 2009/039294 A1 | 3/2009 |
| WO | WO 2009/042170 A1 | 4/2009 |
| WO | WO 2009/042172 A2 | 4/2009 |
| WO | WO 2009/042313 A2 | 4/2009 |
| WO | WO 2009/059041 A1 | 5/2009 |

OTHER PUBLICATIONS

Aaron et al., "Horizons in Prosthesis Dvelopment for the Restoration of Limb Function," Journal of the American Academy of Orthopaedic Surgeons, vol. 14, No. 10, Sep. 2006, pp. S198-S204.
Abidi, "CMOS wireless transceivers: the new wave," IEEE Communications Magazine 37, Aug. 1999, pp. 119-124.
Academic Press Dictionary of Science and Technology, definition of "baseband" Oxford: Elsevier Science and Technology, 1992, 2 pp. (Applicant points out that, in accordance with MPEP 609.04(a), the 1992 year of publication is sufficiently earlier than the effective U.S. filing date and any foregn priority date so that the particular month of publication is not in issue.).
Acuna et al., "Cognitive mechanisms of transitive inference," Exp Brain Res, vol. 146, Sep. 2002, pp. 1-10.
Acuna et al., "Frontal and Parietal Lobe Activation during Transitive Inference in Humans," Cerebral Cortex, vol. 12, No. 12, Dec. 2002, pp. 1312-1321.
Anderson et al., "Recording Advances for Neural Prosthetics," Engineering in Medicine and Biology Society, IEMBS 2004, 26th Annual International Conference of the IEEE, vol. 7, Sep. 2004, pp. 5352-5355.
Anderson et al., "Selecting the signals for a brain-machine interface," Curr Opin Neurobiol, vol. 14, Dec. 2004, pp. 720-726.
Antonini et al., "Deep brain stimulation and its effect on sleep in Parkinson's disease," Sleep Medicine 5, Mar. 2004, pp. 211-214.
Authoritative Dictionary of IEEE Standard Terms (Seventh Edition), definition of "baseband" pp. 86, New York: IEEE, 2000, 3 pp. (Applicant points out that, in accordance with MPEP 609.04(a), the 2000 year of publication is sufficiently earlier than the effective U.S. filing and any foreign priority date so that the particular month of publication is not in issue.).
Avestruz et al., "A 5 uW/Channel Spectral Analysis IC for Chronic Bidirectional Brain- Machine Interfaces," IEEE Journal of Solid-State Circuits, vol. 43, No. 12, Dec. 2008, 19 pp.
Bakker et al., "A CMOS Nested-Chopper Instrumentation Amplifier with 100-nV Offset," IEEE Journal of Solid-State Circuits, vol. 35, No. 12, Dec. 2000, pp. 1877-1883.
Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plaasche, J.H. Huijsing, and W.M.C. Sansen (eds.), Kluwer Academic Publishers, Nov. 1997, 20 pp.
Brown et al., "Basal ganglia local field potential activity: Character and functional significance in the human," Clinical Neurology, vol. 116, Nov. 2005, pp. 2510-2519.
Brown, "Oscillatory Nature of Human Basal Ganglia Activity: Relationship to the Pathophysiology of Parkinson's Disease," Movement Disorders, vol. 18, No. 4, Apr. 2003, pp. 357-363.
Burt et al., "A Micropower Chopper-Stabilized Operational Amplifier using an SC Notch Filter with Synchronous Integration inside the Continuous-Time Signal Path," ISSCC Digest of Technical Papers 2006, Paper 19.6, Feb. 2006, 2 pp.
Cohen et al., "The physiology of brain-computer interfaces," Journal of Physiology, vol. 579, No. 3, Mar. 2007, p. 570.
Denison et al., "A 2 µW 100 nV/rtHz Chopper-Stabilized Instrumentation Amplifier for Chronic Measurement of Neural Field Potentials," Solid-state circuits, IEEE Journal, vol. 42, Dec. 2007, pp. 2934-2945.
Denison et al., "A 2.2µW 94 nV/vHz, Chopper-Stabilized Instrumentation Amplifier for EEG Detection in Chronic Implants," Soli-State Circuits Conference, Digest of Technical Papers, IEEE International, Feb. 2007, 3 pp.
Denison et al., "An 8 µW heterodyning chopper amplifier for direct extraction of 2 µVrms Neuronal Brain Biomarkers," ISSCC, Paper 8.1, Jul. 2008, 3 pp.
Donoghue et al., "Assistive technology and robotic control using motor cortex ensemble-based neural interface systems in humans with tetraplegia," Journal of Physiology 579.3 Mar. 2007, pp. 603-611.
Donoghue et al., "Development of neuromotor prostheses for humans," Advances in Clinical Neurophysiology, Supplements to Clinical Neurophysiology, vol. 57, 2004, pp. 592-606 (Applicant points out that, in accordance with MPEP 609.04(a), the 2004 year of publication is sufficiently earlier than the effective U.S. filing date and any foreign priority date so that the particular month of publication is not in issue.).
Donoghue et al., "Motor Areas of the Cerebral Cortex," Journal of Clinical Neurophysiology, vol. 11, No. 4, Jul. 1994, pp. 382-396.

(56) References Cited

OTHER PUBLICATIONS

Donoghue, "Connecting cortex to machines: recent advances in brain interfaces," Nature Neuroscience, supplement, vol. 5, Nov. 2002, pp. 1085-1088.
Dzwonczyk et al., "Myocardial Electrical Impedance Responds to Ischemia and Reperfusion in Humans," IEEE Transactions on Biomedical Engineering, IEEE Service Center, vol. 51, No. 12, Dec. 2004, pp. 2206-2209.
Eden et al., "Reconstruction of Hand Movement Trajectories from a Dynamic Ensemble of Spiking Motor Cortical Neurons," Proceedings of the 26th Annual International Conference of the IEEE EMBS, San Francisco, CA, USA, Sep. 1-5, 2004, pp. 4017-4020.
Enz et al., "Circuit Techniques for Reducing the Effects of Opamp Imperfections," Proc. of the IEEE, vol. 84, No. 11, Nov. 1996, pp. 1584-1614.
Fetz, "Volitional control of neural activity: implications for brain-computer interfaces," Journal of Physiology, vol. 579, No. 3, 2007, pp. 571-579.
Foffani et al., "Analysis of local field potentials from the human subthalamic nucleus," Proceedings of the 25th Annual International Conference of the IEEE EMBS, Sep. 17-21, Sep. 2003, 3 pp.
Friehs et al., "Brain-Machine and Brain-Computer Interfaces," Stroke, vol. 35, No. 11, Supplement 1, Nov. 2004, pp. 2702-2705.
Haddad et al., "An ultra low-power dynamic translinear cardiac sense amplifier for pacemakers," Circuits and Systems, vol. 5, Mar. 2003, pp. V-37-V40.
Haddad et al., "Analog wavelet transform employing dynamic translinear circuits for cardiac signal characterization," Circuits and Systems, vol. 1, May 2003, pp. 1-121-1-124.
Hadiashar et al., "A Chopper Stabilized CMOS Analog Multiplier with Ultra Low DC Offsets," Solid-State Circuits Conference, Sep. 2006, pp. 364-367.
Harrison et al., "A Low-Power Integrated Circuit for a Wireless 100—Electrode Neural Recording System," IEEE Journal of Solid State Circuits, vol. 42, No. 1, Jan. 2007, pp. 123-133.
Harrison et al., "A Low-Power Low-Noise CMOS Amplifier for Neural Recording Applications," IEEE Journal of Solid-State Circuits, vol. 38, No. 6, Jun. 2003, pp. 958-965.
Harrison et al., "Local Field Potential Measurement with Low-Power Analog Integrated Circuit," Proceedings of the 26th Annual International Conference of the IEEE EMBS, Sep. 1-5, 2004, 4 pp.
Hatsopoulos et al., "Cortically controlled brain-machine interface," Proceedings of the 2005 IEEE, Engineering in Medicine and Biology 27th Annual Conference, Sep. 1-4, 2005, pp. 7660-7663.
Heldman et al., "Local Field Potential Spectral Tuning in Motor Cortex During Reaching," IEEE Transactions on Neural Systems and Rehabilitation Engineering, vol. 14, No. 2, Jun. 2006, pp. 180-183.
Hess et al., "Long-Term Potentiation of Horizontal Connections Provides a Mechanism to Reorganize Cortical Motor Maps," Journal of Neurophysiology, vol. 71, No. 6, Jun. 1994, pp. 2543-2547.
Hochberg et al., "Neuronal ensemble control of prosthetic devices by a human with tetraplegia," Nature, vol. 442, Jul. 2006, pp. 164-171.
Hochberg et al., "Sensors for Brain-Computer Interfaces: Options for Turning Thought into Action," IEEE Engineering in Medicine and Biology Magazine, Sep./Oct. 2006, pp. 32-38.
Hoshi,"Functional specialization within the dorsolateral prefrontal cortex: A review of anatomical and physiological studies of non-human primates," Neuroscience Research 54, Feb. 2006, pp. 73-84.
Jianping et al., "Study on Feature Extraction of the Sleep-Multigraph," Journal of Biomedical Engineering, vol. 22, No. 5, Dec. 31, 2005, pp. 906-909 (Translation provided for only the abstract).
Krusienski et al.,"A μ-Rhythm Matched Filter for Continuous Control of a Brain-Computer Interface," IEEE Transactions on Biomedical Engineering, vol. 54, Feb. 2007, pp. 273-280.
Kun et al., "Algorithm for Tissue Ischemia Estimation Based on Electrical Impedance Spectroscopy," IEEE Transactions on Biomedical Engineering, IEEE Service Center, vol. 50, No. 12, Dec. 2003, pp. 1352-1359.
Lai et al. "Muscle Tone Suppression and Stepping Produced by Stimulation of Midbrain and Rostral Pontine Reticular Formation," The Journal of Neuroscience, vol. 10, No. 8, Aug. 1990, 8 pp.
Lee et al., "A 64 Channel Programmable Closed-Loop Deep Brain Stimulator with 8 channel Neural Amplifier and Logarithmic ADC," 2008 Symposium on VLSI Circuits Digest of Technical Papers, Mar. 2008, pp. 76-77.
Lima et al., "The Role of the Substantia Nigra Pars Compacta in Regulating Sleep Patterns in Rats," PLoS ONE, www.plosone.org, Issue 6, e514, Jun. 2007, 7 pp.
Makinwa et al., "A CMOS Temperature-to-frequency converter with an Inaccuracy of less than ±0.5 ° C. (3o) from −40 ° C. to 105 ° C.," IEEE Journal of Solid State Circuits, vol. 41, No. 12, Dec. 2006, pp. 2992-2997.
Makinwa, "Dynamic Offset Cancellation Techniques," Smart Sensor Systems '02, May 2002, 42 pp.
Martins et al., "A CMOS IC for Portable EEG Acquisition Systems," IEEE Transactions on Instrumentation and Measurement, vol. 47, No. 5, Oct. 1998, pp. 1191-1196.
Masui, "A 0.6 V Supply CMOS Amplifier Using Noise Reduction Technique of Autozeroing and Chopper Stabilization," 21st Century COE Program, Hiroshima University, Proceedings of the Fifth Hiroshima International Workshop, Jan. 2007, 5 pp.
Maynard et al., "Neuronal Interactions Improve Cortical Population Coding of Movement Direction," The Journal of Neuroscience, vol. 19, No. 18, Sep. 15, 1999, pp. 8083-8093.
Min et al., "Electrical Impedance and Cardiac Monitoring—Technology, Potential and Applications," International Journal of Bioelectromagnetism, International Society for Bioelectromagnetism, vol. 5 No. 1 Jan. 2003, pp. 53-56.
Neagu et al. "PPN Evoked Potentials During STN Stimulation of Parkinson's Disease Patients," Presentation Abstract, 40th Annual Meeting Neuroscience, Nov. 16, 2010, 2 pp.
Ng et al., "A CMOS Analog Front-End IC for Portable EEG/ECG Monitoring Applications," IEEE Trans. on Circuits and Systems, vol. 52, No. 11, Nov. 2005, 13 pp.
Ojakangas et al, "Decoding movement intent from human premotor cortex neurons for neural prosthetic applications," Journal of Clinical Neurophysiology, vol. 23, No. 6, Dec. 2006, pp. 1-14.
Paninski et al., "Spatiotemporal Tuning of Motor Cortical Neurons for Hand Position and Velocity," Journal of Neurophysiology, vol. 91, Jan. 2004, pp. 515-532.
Paninsiu et al., "Superlinear Population Encoding of Dynamic Hand Trajectory in Primary Motor Cortex," The Journal of Neuroscience, vol. 24, No. 39, Sep. 29, 2004, pp. 8551-8561.
Patterson et al., "A Microelectrode/Microelectronic Hybrid Device for Brain Implantable Neuroprosthesis Applications," IEEE Transactions on Biomedical Engineering, vol. 51, No. 10, Oct. 2004, pp. 1845-1853.
Piette et al., "A unique episode of REM sleep behavior disorder triggered during surgery for Parkinson's disease," Journal of the Neurological Sciences, vol. 253, Feb. 2007, pp. 73-76.
Rauscher et al., "Practical Realization of an Analyzer Operating on the Heterodyne Principle," Chapter 4 (partial) of Fundamentals of Spectrum Analysis, Rohde & Schwarz, 2001, pp. 34-64 (Applicant points out that, in accordance with MPEP 609.04(a), the 2001 year of publication is sufficiently earlier than the effective U.S. filing date and any foreign priority date so that the particular month of publication is not in issue.).
Rudell et al. "Recent Developments in High Integration Multi-Standard CMOS Transceivers for Personal Communication Systems," 1998 International Symposium on Low Power Electronics and Design, Aug. 1998, pp. 149-154.
Salthouse et al., "A practical micropower programmable bandpass filter for use in bionic ears," Solid-state Circuits, IEEE Journal, vol. 38, Jan. 2003, pp. 63-70.
Sanduleanu et al., "A Low Noise, Low Residual Offset, Chopped Amplifier for Mixed Level Applications," IEEE, 0-7803-5008-1/98, Sep. 1998, pp. 333-336.

(56) References Cited

OTHER PUBLICATIONS

Sanes et al., "Plasticity and Primary Motor Cortex," Annual Review of Neuroscience, vol. 23, Mar. 2000, pp. 393-415.
Sarpeshkar et al., "An ultra-low-power programmable analog bionic ear processor," Biomedical Engineering, IEEE Transactions, vol. 52, Apr. 2005, pp. 711-727.
Sarpeshkar et al., "Low power circuits for brain—machine interfaces," Circuits and Systems, Sep. 2007, pp. 2068-2071.
Sarpeshkar, "Borrowing from biology makes for low-power computing," IEEE Spectrum, May 2006, pp. 24-29.
Schwartz, "Useful signals from motor cortex", Journal of Physiology, vol. 579, No. 3, 2007, pp. 581-601.
Serruya et al., "Instant neural control of a movement signal," Nature, vol. 416, Mar. 2002, pp. 141-142.
Serruya et al., "Robustness of neuroprosthetic decoding algorithms," Biological Cybernetics, vol. 88, Feb. 2003, pp. 219-228.
Shoham et al., "Statistical Encoding Model for a Primary Motor Cortical Brain-Machine Interface," IEEE Transactions on Biomedical Engineering, vol. 52, No. 7, Jul. 2005, pp. 1312-1322.
Silberstein et al., "Patterning of globus pallidus local field potentials differs between Parkinson's disease and dystonia," Brain, vol. 126, Aug. 2003, pp. 2597-2608.
Smart et al., "Automatic Detection of High Frequency Epileptiform Oscillations from Intracranial EEG Recordings of Patients with Neocortical Epilepsy," Technical, Professional and Student Development Workshop, 2005, IEEE Region 5 and IEEE Denver Section, Apr. 2005, pp. 53-58.
Song et al., "Development of a Chipscale Integrated Microelectrode/Microelectronic Device for Brain Implantable Neuroengineering Applications," IEEE Transactions on Neural Systems and Rehabilitation Engineering, vol. 13, No. 2, Jun. 2005, pp. 220-226.
Song et al., "Development of an Integrated Microelectrode/Microelectronic Device for Brain Implantable Neuroengineering Applications," Proceedings of the 26th Annual International Conference of the IEEE EMBS, San Francisco, CA, USA, Sep. 1-5, 2004, pp. 4053-4056.
Suner et al., "Reliability of Signals From a Chronically Implanted, Silicon-Based Electrode Array in Non-Human Primate Primary Motor Cortex," IEEE Transactions on Neural Systems and Rehabilitation Engineering, vol. 13, No. 4, Dec. 2005, pp. 524-541.
Takakusaki et al., "Evidence for a role of basal ganglia in the regulation of rapid eye movement sleep by electrical and chemical stimulation for the pedunculopontine tegmental nucleus and the substantia nigra pars reticulata in decerebrate cats," Neuroscience, 2004, vol. 124, No. 1, pp. 207-220 (Abstract Only) (Applicant points out that, in accordance with MPEP 609.04(a), the 2004 year of publication is sufficiently earlier than the effective U.S. filing and any foreign priority date so that the particular month of publication is not in issue.).
Tornqvist et al., "Effects of Different Electrical Parameter Settings on the Intelligibility of Speech in Patients with Parkinson's Disease Treated With Subthalamic Deep Brain Stimulation," Movement Disorders, vol. 20, No. 4, Apr. 2005, pp. 416-423.
Wattanapanitch et al., "An energy-efficient micropower neural recording amplifier," Biomedical Circuits and Systems, IEEE Transactions, vol. 1, Jun. 2007, pp. 136-147.
Wingeier et al., "Intra-operative STN DBS attenuates the prominent beta rhythm in the STN in Parkinson's disease," Experimental Neurology, Nov. 2005, 8 pp.
Wolpaw, "Brain-computer interfaces as new brain output pathways," Journal of Physiology, vol. 579, No. 3, Jan. 2007, pp. 613-619.
Wood et al., "Automatic Spike Sorting for Neural Decoding," Proceedings of the 26th Annual International Conference of the IEEE EMBS, San Francisco, CA, USA, Sep. 1-5, 2004, pp. 4009-4012.
Wood et al., "Inferring Attentional State and Kinematics from Motor Cortical Firing Rates," Proceedings of the 2005 IEEE, Engineering in Medicine and Biology 27th Annual Conference, Sep. 1-4, 2005, pp. 149-152.
Wood et al., "On the Variability of Manual Spike Sorting," IEEE Transactions on Biomedical Engineering, vol. 51, No. 6, Jun. 2004, pp. 912-918.
Wu et al., "A IV 2.3µW Biomedical Signal Acquisition IC," ISSCC Digest of Technical Papers 2006, paper 2.7, Feb. 2006, 2 pp.
Wu et al., "Bayesian Population Decoding of Motor Cortical Activity Using a Kalman Filter," Neural Computation, vol. 18, No. 1, Jan. 2006, pp. 80-118.
Wu et al., "Closed-Loop Neural Control of Cursor Motion using a Kalman Filter," Proceedings of the 26th Annual International Conference of the IEEE EMBS, San Francisco, CA, USA, Sep. 1-5, 2004, pp. 4126-4129.
Wu et al., "Modeling and Decoding Motor Cortical Activity Using a Switching Kalman Filter," IEEE Transactions on Biomedical Engineering, vol. 51, No. 6, Jun. 2004, pp. 933-942.
Yates et al., "An ultra low power low noise chopper amplifier for wireless EEG," In 49th IEEE International Midwest Symposium on Circuits and Systems, Jan. 2006, MWSCAS '06, vol. 2, 2006, pp. 449-452.
Yazicioglu et al., "A 200µW Eight-Channel Acquisition ASIC for Ambulatory EEG Systems," Solid-state circuits conference, Jul. 2008, 3 pp.
Yazicioglu et al., "A 60 µW 60nV/ vHz Readout Front-End for Portable Biopotential Acquisition Systems," ISSCC Digest of Technical Papers 2006, paper 2.6, Feb. 2006, 2 pp.
Ying, "Chopper Stabilized Amplifiers," Term Paper, Department of Electrical and Computer Engineering, University of Toronto, Nov. 12, 2001, 17 pp.
International Preliminary Report on Patentability for International Application No. PCT/US2008/077720, mailed Apr. 19, 2010, 11 pages.
Reply to Written Opinion for International Application No. PCT/US2008/077720, filed Nov. 23, 2009, 16 pp.
Decision on Rejection, and translation thereof, from counterpart Chinese Patent Application No. 200880125611.1, dated Oct. 31, 2014, 18 pp.
Fourth Office Action, and translation thereof, from counterpart Chinese Patent Application No. 200880125611.1, dated Dec. 3, 2013, 17 pp.
Fifth Office Action, and translation thereof, from counterpart Chinese Application No. 200880125611.1, dated Jul. 3, 2014, 12 pp.
International Search Report and Written Opinion of International Application No. PCT/US2008/077720, mailed Jun. 29, 2009, 14 pp.
Office Action from counterpart Chinese Application No. 200880125611.1, dated Aug. 17, 2011, 10 pp.
Third Office Action from Chinese Patent Application No. 200880125611.1, dated Jul. 31, 2013, 13 pp.
Prosecution History from U.S. Pat. No. 9,072,870, dated Dec. 27, 2011 through Jun. 8, 2015, 285 pp.
Prosecution History from U.S. Appl. No. 12/616,513, dated Apr. 16, 2012 through Nov. 12, 2014, 154 pp.
Prosecution History from U.S. Appl. No. 13/211,904, dated Sep. 16, 2013 through Aug. 24, 2015, 117 pp.
U.S. Appl. No. 60/999,097, filed Oct. 16, 2007, entitled, "Responsive Therapy System".
Urrestarazu et al., "Beta Activity in the Subthalamic Nucleus During Sleep in Patients with Parkinson's Disease," Movement Disorders, vol. 24, Issue No. 2, published online Oct. 24, 2008, (pp. 254-260).
Decision on Appeal from U.S. Appl. No. 12/616,513, dated Oct. 28, 2016, 6 pp.
Notice of Allowance from U.S. Appl. No. 12/616,513, dated Jan. 9, 2017, 6 pp.

* cited by examiner

| Program Table Record | Patient State/ Sleep Stage | Amplitude (V) | Pulse Width (μs) | Frequency (Hz) | Electrode Configuration |
|---|---|---|---|---|---|
| 1 | STAGE 1 | 10 | 325 | 150 | 3+ 3- |
| 2 | STAGE 2 | 5 | 180 | 50 | 0 0 |
| 3 | DEEP SLEEP | 0 | 0 | 0 | 0 0 |
| 4 | REM | 10 | 325 | 150 | 1- 3+ |
| 4 | AWAKE | 10 | 325 | 150 | 1- 3+ |

| PATIENT STATE/ SLEEP STAGE | BETA BAND POWER | THERAPY PROGRAM |
|---|---|---|
| AWAKE | > THRESHOLD A | THERAPY PROGRAM A |
| STAGE 1 | > THRESHOLD A | THERAPY PROGRAM A |
| STAGE 2 | < THRESHOLD A | THERAPY PROGRAM B |
| DEEP SLEEP | < THRESHOLD A | THERAPY PROGRAM B |
| REM | > THRESHOLD A | THERAPY PROGRAM A |

FIG. 8

| PATIENT STATE/ SLEEP STAGE | ALPHA BAND POWER |
|---|---|
| AWAKE | > THRESHOLD B |
| STAGE 1 | < THRESHOLD B |
| STAGE 2 | < THRESHOLD B |
| DEEP SLEEP | < THRESHOLD B |
| REM | < THRESHOLD B |

FIG. 9

| PATIENT STATE/ SLEEP STAGE | SIGMA BAND POWER/ HIGH BETA BAND POWER | THERAPY PROGRAM |
|---|---|---|
| AWAKE | < THRESHOLD C | THERAPY PROGRAM C |
| STAGE 1 | < THRESHOLD C | THERAPY PROGRAM C |
| STAGE 2 | > THRESHOLD C | THERAPY PROGRAM D |
| DEEP SLEEP | > THRESHOLD C | THERAPY PROGRAM D |
| REM | < THRESHOLD C | THERAPY PROGRAM C |

FIG. 15A

| PATIENT STATE/ SLEEP STAGE | BETA BAND POWER/ ALPHA BAND POWER | THERAPY PROGRAM |
|---|---|---|
| AWAKE | > THRESHOLD D<br>< THRESHOLD E | THERAPY PROGRAM E |
| STAGE 1 | > THRESHOLD D<br>< THRESHOLD E | THERAPY PROGRAM E |
| STAGE 2 | < THRESHOLD D | THERAPY PROGRAM F |
| DEEP SLEEP | < THRESHOLD D | THERAPY PROGRAM F |
| REM | > THRESHOLD E | THERAPY PROGRAM G |

FIG. 15B

| PATIENT STATE/ SLEEP STAGE | THETA BAND POWER/ ALPHA BAND POWER | THERAPY PROGRAM |
|---|---|---|
| GROUP A<br>AWAKE<br>STAGE 1<br>REM | < THRESHOLD F | THERAPY PROGRAM H |
| GROUP B<br>STAGE 2<br>DEEP SLEEP | > THRESHOLD F | THERAPY PROGRAM I |

FIG. 15C

SLEEP STAGE DETECTION

This application is a continuation of U.S. patent application Ser. No. 12/238,105 by Wu et al., which is entitled "SLEEP STAGE DETECTION," and was filed on Sep. 25, 2008, and which claims the benefit of U.S. Provisional Application No. 61/049,166 to Wu et al., which is entitled, "SLEEP STAGE DETECTION" and was filed on Apr. 30, 2008, and U.S. Provisional Application No. 61/023,522 to Stone et al., which is entitled, "THERAPY PROGRAM SELECTION" and was filed on Jan. 25, 2008. The entire contents of above-identified U.S. patent application Ser. No. 12/238,105 and U.S. Provisional Application Nos. 61/049,166 and 61/023,522 are incorporated herein by reference.

TECHNICAL FIELD

The disclosure relates to medical therapy systems, and, more particularly, control of medical therapy systems.

BACKGROUND

In some cases, an ailment or medical condition may affect the quality of a patient's sleep. For example, neurological disorders may cause a patient to have difficulty falling asleep, and may disturb the patient's sleep, e.g., cause the patient to wake frequently during the night and/or early in the morning. Further, neurological disorders may cause the patient to have difficulty achieving deep sleep stages, such as one or more of the nonrapid eye movement (NREM) sleep stages.

Examples of neurological disorders that may negatively affect patient sleep quality include movement disorders, such as tremor, Parkinson's disease, multiple sclerosis, or spasticity. The uncontrolled movements associated with such movement disorders may cause a patient to have difficulty falling asleep, disturb the patient's sleep, or cause the patient to have difficulty achieving deep sleep stages. Parkinson's disease may also cause rapid eye movement (sleep) behavior disorders (RBD), in which case, a patient may act out dramatic and/or violent dreams, shout or make other noises (e.g., grunting) during the rapid eye movement (REM) stage sleep.

Epilepsy is another example of a neurological disorder that may affect sleep quality. In some patients, epileptic seizures may be triggered by sleep or transitions between sleep stages, and may occur more frequently during sleep. Furthermore, the occurrence of seizures may disturb sleep, e.g., wake the patient. Often, epilepsy patients are unaware of the seizures that occur while they sleep, and suffer from the effects of disturbed sleep, such as daytime fatigue and concentration problems, without ever knowing why.

Psychological disorders, such as depression, mania, bipolar disorder, or obsessive-compulsive disorder, may also similarly affect the ability of a patient to sleep, or at least experience quality sleep. In the case of depression, a patient may "sleep" for long periods of the day, but the sleep is not restful, e.g., includes excessive disturbances and does not include deeper, more restful sleep stages. Further, chronic pain, whether of neurological origin or not, as well as congestive heart failure, gastrointestinal disorders and incontinence, may disturb sleep or otherwise affect sleep quality.

Drugs are often used to treat neurological disorders. In some cases, neurological disorders are treated via an implantable medical device (IMD), such as an implantable stimulator or drug delivery device. The treatments for neurological orders may themselves affect sleep quality.

Further, in some cases, poor sleep quality may increase the symptoms experienced by a patient. For example, poor sleep quality may result in increased movement disorder symptoms in movement disorder patients. The link between poor sleep quality and increased symptoms is not limited to ailments that negatively impact sleep quality, such as those listed above. Nonetheless, the condition of a patient with such an ailment may progressively worsen when symptoms disturb sleep quality, which may, in turn, increase the frequency and/or intensity of symptoms of the patient's condition.

SUMMARY

In general, the disclosure is directed to determining a sleep stage of a patient's sleep state based on a frequency characteristic of a biosignal from a brain of the patient. A frequency characteristic of the biosignal may include, for example, a power level (or energy) within one or more frequency bands of the biosignal, a ratio of the power level in two or more frequency bands, a correlation in change of power between two or more frequency bands, a pattern in the power level of one or more frequency bands over time, and the like. In some cases, a frequency characteristic of the biosignal may be associated with more than one sleep stage. Accordingly, a sleep stage determination may include a determination of whether a patient is generally in a sleep stage that is part of a group of sleep stages associated with the same or similar biosignal frequency characteristic.

In some examples, therapy delivered to the patient during the sleep state may be controlled based on the determined sleep stage. For example, a therapy program may be selected based on the detected sleep stage or a therapy program may be modified based on the detected sleep stage. Therapy to the patient during the detected sleep stage may be delivered according to the selected or modified therapy program.

In some examples, therapy delivery to the patient may be controlled after making a first determination of a patient sleep stage based on the biosignal sensed within the patient's brain and a second determination of a patient sleep stage based on another physiological parameter of patient. If the first and second sleep stage determinations are consistent, therapy delivery to the patient may be controlled according to the determined sleep stage. If the first and second sleep stage determinations are not consistent, the therapy delivery may not be adjusted, but, rather, the therapy parameter values that were implemented prior to the first and second sleep stage determinations may be maintained.

In one aspect, the disclosure is directed to a method comprising receiving a biosignal that is indicative of activity within a brain of a patient, determining a frequency characteristic of the biosignal, comparing the frequency characteristic of the biosignal to at least one of a threshold value or template, and determining a sleep stage of the patient based on the comparison between the frequency characteristic of the biosignal and the at least one of the threshold value or template, wherein the sleep stage occurs during a sleep state of the patient, the sleep state comprising a plurality of sleep stages.

In another aspect, the disclosure is directed to a method comprising sensing a biosignal from a brain of a patient, determining a frequency characteristic of the biosignal, determining whether the patient is in at least one of an awake state, a first sleep stage or a second sleep stage based on the frequency characteristic of the biosignal, activating therapy delivery to the patient if the patient is in the awake state or the first sleep stage, and deactivating or decreasing an intensity of therapy delivered to the patient if the patient is in the second sleep stage.

In another aspect, the disclosure is directed to a system comprising a sensing module that senses a biosignal generated within a brain of a patient, and a processor that receives the biosignal, determines a frequency characteristic of the biosignal, compares the frequency characteristic of the biosignal to at least one of a threshold value or template, and determines a sleep stage of the patient based on the comparison between the frequency characteristic of the biosignal and the at least one of the threshold value or the template, wherein the sleep stage occurs during a sleep state of the patient, the sleep state comprising a plurality of sleep stages.

In another aspect, the disclosure is directed to a system comprising means for receiving a biosignal that is indicative of activity within a brain of a patient, means for determining a frequency characteristic of the biosignal, means for comparing the frequency characteristic of the biosignal to at least one of a threshold value or template, and means for determining a sleep stage of the patient based on the comparison between the frequency characteristic of the biosignal and the at least one of the threshold value or template, wherein the sleep stage occurs during a sleep state of the patient, the sleep state comprising a plurality of sleep stages.

In another aspect, the disclosure is directed to a computer-readable medium containing instructions. The instructions cause a programmable processor to receive a biosignal that is indicative of activity within a brain of a patient, determine a frequency characteristic of the biosignal, compare the frequency characteristic of the biosignal to at least one of a threshold value or template, and determine a sleep stage of the patient based on the comparison between the frequency characteristic of the biosignal and the at least one of the threshold value or template, wherein the sleep stage occurs during a sleep state of the patient, the sleep state comprising a plurality of sleep stages.

In another aspect, the disclosure is directed to a method comprising monitoring a biosignal during a sleep state of a patient, wherein the biosignal is indicative of activity within a brain of a patient, evaluating one or more frequency characteristics of the biosignal, determining a sleep stage of the patient, wherein the sleep stage occurs during the sleep state of the patient, the sleep state comprising a plurality of sleep stages, and associating the one or more frequency characteristics of the biosignal with the sleep stage, wherein the one or more frequency characteristics comprises at least one of a threshold value or a template.

In another aspect, the disclosure is directed to a computer-readable medium containing instructions. The instructions cause a programmable processor to evaluate one or more frequency characteristics of a biosignal that is indicative of activity within a brain of a patient, determine a sleep stage of the patient, wherein the sleep stage occurs during a sleep state of the patient, the sleep state comprising a plurality of sleep stages, and associate the one or more frequency characteristics of the biosignal with the sleep stage, wherein the one or more frequency characteristics comprises at least one of a threshold value or a template.

In another aspect, the disclosure is directed to a system comprising a sensing module that generates a biosignal indicative of activity within a brain of a patient, and a processor that receives the biosignal during a sleep state of the patient, determines a frequency characteristic of the biosignal, evaluates one or more frequency characteristics of the biosignal, determines a sleep stage of the patient, wherein the sleep stage occurs during the sleep state of the patient, the sleep state comprising a plurality of sleep stages, and associates the one or more frequency characteristics of the biosignal with the sleep stage, wherein the one or more frequency characteristics comprises at least one of a threshold value or a template.

In another aspect, the disclosure is directed to a computer-readable medium comprising instructions. The instructions cause a programmable processor to perform any of the techniques described herein.

The details of one or more examples of the disclosure are set forth in the accompanying drawings and the description below. Other features, objects, and advantages of the systems, methods, and devices in accordance with the disclosure will be apparent from the description and drawings, and from the claims.

BRIEF DESCRIPTION OF DRAWINGS

FIG. 8 illustrates an example table that associates different sleep stages and a patient awake state with threshold power values within a beta frequency band and with therapy programs.

FIG. 9 illustrates an example table that associates different sleep stages and a patient awake state with threshold power values within an alpha frequency band.

FIG. 15A illustrates an example table that associates different sleep stages and a patient awake state with therapy programs and a common threshold value indicative of a ratio of powers between sigma and high beta frequency bands.

FIG. 15B illustrates an example table that associates different sleep stages and a patient awake state with therapy programs and a different threshold values indicative of a ratio of powers between beta and alpha frequency bands.

FIG. 15C illustrates an example table that associates different sleep stages and a patient awake state with therapy programs and a common threshold value indicative of a ratio of powers between theta and alpha frequency bands.

DETAILED DESCRIPTION

Figure 1:
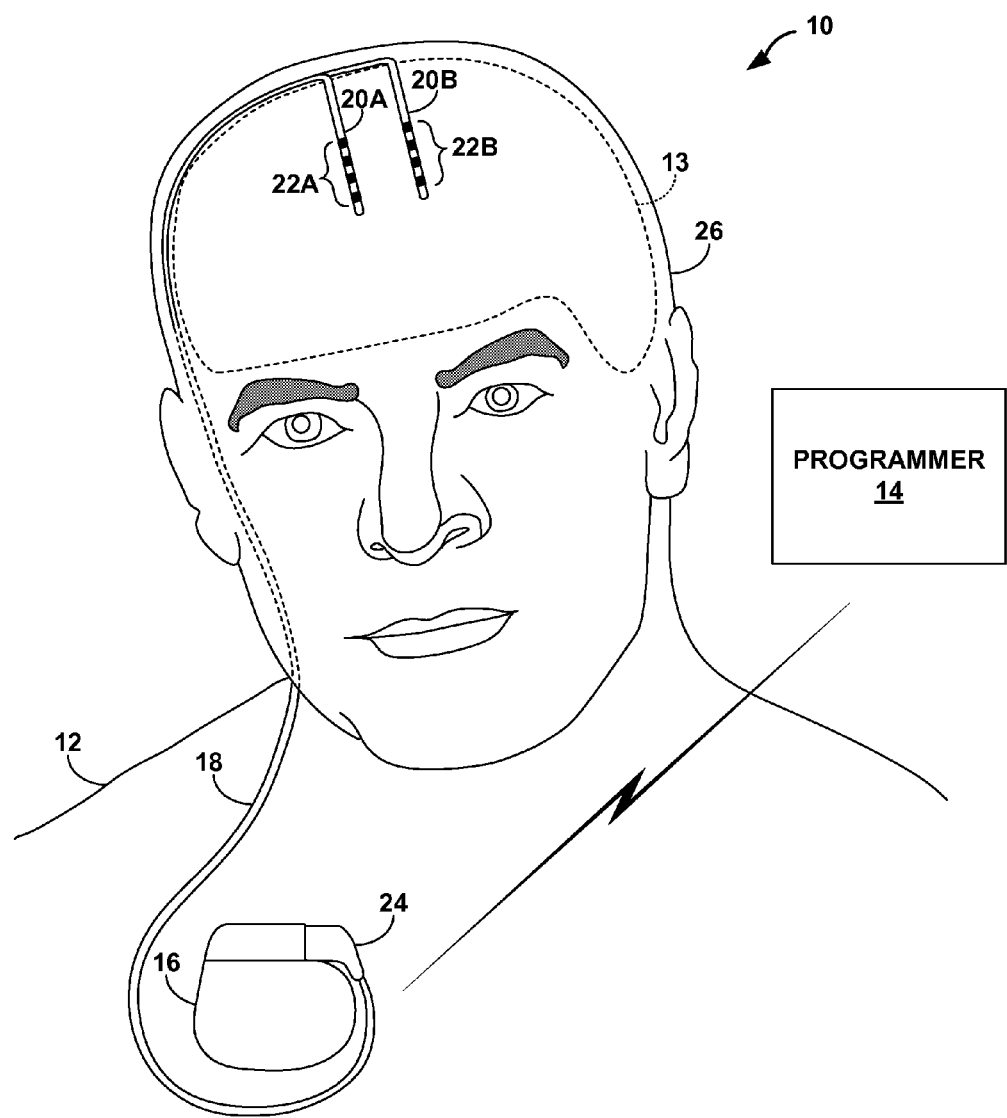
FIG. 1 is a conceptual diagram illustrating an example deep brain stimulation (DBS) system.

FIG. 1 is a conceptual diagram illustrating an example deep brain stimulation (DBS) system 10 that manages a medical condition of patient 12, such as a neurological disorder. DBS system 10 includes medical device programmer 14, implantable medical device (IMD) 16, lead extension 18, and leads 20A and 20B with respective electrodes 22A, 22B. Patient 12 ordinarily will be a human patient. In some cases, however, DBS system 10 may be applied to other mammalian or non-mammalian non-human patients. Some patient conditions, such as Parkinson's disease and other neurological conditions, result in impaired sleep states. DBS system 10 may help minimize the severity or duration, and, in some cases, eliminate symptoms associated with the patient condition, including impaired sleep states.

In the example shown in FIG. 1, DBS system 10 includes a processor that determines whether patient 12 is in a sleep state, and controls therapy to patient 12 upon determining patient 12 is in the sleep state. The sleep state may refer to a state in which patient 12 is intending on sleeping (e.g., initiating thoughts of sleep), is attempting to sleep or has initiated sleep and is currently sleeping. In addition, the processor may determine a sleep stage of the sleep state based on a biosignal detected within brain 13 of patient 12, and control therapy delivery to patient 12 based on a determined sleep stage. Example biosignals are described below.

Within a sleep state, patient 12 may be within one of a plurality of sleep stages. Example sleep stages include, for example, Stage 1 (also referred to as Stage N1 or S1), Stage 2 (also referred to as Stage N2 or S2), Deep Sleep (also referred to as slow wave sleep), and rapid eye movement (REM). The Deep Sleep stage may include multiple sleep stages, such as Stage N3 (also referred to as Stage S3) and Stage N4 (also referred to as Stage S4). In some cases, patient 12 may cycle through the Stage 1, Stage 2, Deep Sleep, REM sleep stages more than once during a sleep state. The Stage 1, Stage 2, and Deep Sleep stages may be considered non-REM (NREM) sleep stages.

During the Stage 1 sleep stage, patient 12 may be in the beginning stages of sleep, and may begin to lose conscious awareness of the external environment. During the Stage 2 and Deep Sleep stages, muscular activity of patient 12 may decrease, and conscious awareness of the external environment may disappear. During the REM sleep stage, patient 12 may exhibit relatively increased heart rate and respiration compared to Sleep Stages 1 and 2 and the Deep Sleep stage. In some cases, the Stage 1, Stage 2, and deep sleep stages may each last about five minutes to about fifteen minutes, although the actual time ranges may vary between patients. In some cases, REM sleep may begin about ninety minutes after the onset of sleep, and may have a duration of about five minutes to about fifteen minutes or more, although the actual time ranges may vary between patients.

In some examples, DBS system 10 stores a plurality of therapy programs (e.g., a set of therapy parameter values), and at least one stored therapy program is associated with at least one sleep stage. A processor of IMD 16 or programmer 14 may select a stored therapy program that defines therapy parameter values for therapy delivery to patient 12 based on a determined sleep stage. In this way, the processor may control therapy delivery to patient 12 based on the determined sleep stage. In some examples, at least one of the stored therapy programs is associated with a respective one of at least two different sleep stages. In addition, in some examples, at least one of the stored therapy programs is associated with at least two different sleep stages.

DBS system 10 is useful for managing a patient condition that results an impaired sleep state, which may be presented impaired sleep quality in or more sleep stages. Different therapy parameter values may provide efficacious therapy (e.g., improved sleep quality) for different sleep stages of patient 12. Rather than delivering therapy according to one or more therapy programs regardless of the patient's current sleep stage, DBS system 10 selectively delivers a therapy program that helps provide efficacious therapy during a detected sleep stage of patient 12. Further, in some examples, therapy delivery to patient 12 may be decreased or even deactivated upon detecting a particular sleep stage, thereby conserving power of IMD 16, which may have a limited amount of stored power.

In other examples, DBS system 10 may modify at least one therapy parameter value of a stored program based on a determined sleep stage. The modifications to the therapy program may be made based on instructions that are associated with the determined sleep stage. In this way, DBS system 10 is configured to adapt therapy parameter values to a current sleep stage and deliver responsive therapy during the sleep stage. The current sleep stage may be the sleep stage of patient 12 at approximately the same time at which the sleep stage is detected and, in some cases, approximately the same time at which a therapy program is selected.

As previously discussed, a sleep stage may refer to a particular phase of sleep during a sleep state of patient 12, whereas the sleep state refers to a situation in which patient 12 is intending on sleeping (e.g., initiating thoughts of sleep), is attempting to sleep or has initiated sleep and is currently sleeping. When patient 12 attempts to sleep, patient 12 may successfully initiate sleep, but may not be able to maintain a certain sleep stage (e.g., a Deep Sleep stage). As another example, when patient 12 attempts to sleep, patient 12 may not be able to initiate sleep or may not be able to initiate a certain sleep stage. In some cases, a patient condition, such as Parkinson's disease, may affect the quality of a patient's sleep. For example, patients that are afflicted with neurological disorders may suffer from sleep disturbances, such as, insomnia, disturbances in REM sleep (e.g., REM sleep behavior disorders), disrupted sleep architecture, periodic limb movements or sleep respiratory disorders or daytime somnolence. Daytime somnolence may include excessive sleepiness caused by a decreased quality of sleep during the night. Accordingly, neurological disorders may cause patient 12 to have difficulty falling asleep and/or may disturb the patient's sleep, e.g., cause patient 12 to wake periodically. Further, neurological disorders may cause patient 12 to have difficulty achieving deeper sleep stages, such as one or more of the NREM sleep stages. The sleep disorder symptoms may be related to nocturnal rigidity, hypokinesia, pain, effects of antiparkisonian drugs, anxiety and depression (which may coexist with the movement disorder), and dysfunctions of one or more brain structures involved in sleep regulation.

Epilepsy is an example of a neurological disorder that may affect sleep quality. Other neurological disorders that may negatively affect patient sleep quality include movement disorders, such as tremor, Parkinson's disease, multiple sclerosis, or spasticity. Movement disorders may include symptoms such as rigidity, bradykinesia (i.e., slow physical movement), rhythmic hyperkinesia (e.g., tremor), nonrhythmic hyperkinsesia (e.g., tics) or akinesia (i.e., a loss of physical movement). Uncontrolled movements associated with some movement disorders or difficulty moving may cause a patient to have difficulty falling asleep, disturb the patient's sleep, or cause the patient to have difficulty achieving deeper sleep. Further, in some cases, poor sleep quality may increase the frequency or intensity of symptoms experienced by patient 12 due to a neurological disorder. For example, poor sleep quality has been linked to increased movement disorder symptoms in movement disorder patients.

In some examples, DBS system 10 or other types of therapy systems may help manage sleep disorder symptoms of patients with conditions other than neurological conditions, such as psychiatric (or psychological) disorders. Examples of psychiatric disorders that may result in one or more impaired sleep stages includes major depressive disorder, anxiety, hypomania or bipolar disorder.

In some examples, delivery of stimulation to one or more regions of brain 13, such as the subthalamic nucleus, may be an effective treatment for movement disorders, such as Parkinson's disease, and the treatment for the movement disorder may also improve sleep quality in certain aspects, such as decreasing sleep fragmentation. However, other aspects of the patient's sleep may remain unimproved by the DBS to treat movement disorders. Accordingly, DBS system 10 provides therapy delivery to patient 12 during particular sleep stages, where the therapy delivery may be specifically configured to address sleep disorder symptoms associated with the particular sleep stages, in order to help alleviate at least some sleep disturbances. Dynamically changing the therapy parameter values based on the patient's sleep stage may be useful for addressing the patient's sleep disorder symptoms.

Patients with Parkinson's disease or other movement disorders associated with a difficulty moving (e g, akinesia, bradykinesia or rigidity) may have a poor quality of sleep during the Stage 1 sleep stage, when patient 12 is attempting to fall asleep. For example, an inability to move during the Stage 1 sleep stage may be discomforting to patient 12, which may affect the ability to fall asleep. Accordingly, during a sleep stage associated with the Stage 1 sleep stage, a processor of IMD 16 or programmer 14 may select a therapy program that helps improve the motor skills of patient 12, such that patient 12 may initiate movement or maintain movement, e.g., to adjust a sleeping position.

In addition, patients with movement disorders associated with a difficulty moving may find it difficult to get out of bed after waking up. Accordingly, upon determining that a patient 12 is no longer in a sleep state (e.g., no longer asleep or attempting to sleep) based on biosignals within brain 13, DBS system 10 may control delivery of a therapy to help patient 12 get out of bed or otherwise initiate movement. In contrast, therapy systems that only rely on motion detectors (e.g., accelerometers) to control therapy systems may be ineffective for patients with Parkinson's disease or other difficulty initiating movement, because the patient may be awake, yet unable to move. In other words, a therapy system that would rely primarily on an accelerometer or other motion sensors may be unable to determine when a Parkinson's patient has woken up because the patient may be unable to move. In contrast, DBS system 10 may select a therapy program that helps improve the motor skills of patient 12 upon detecting the patient's awake state (i.e., when patient 12 is not sleeping), such that patient 12 may initiate movement or maintain movement, e.g., to help patient 12 get out of bed.

In some patients with movement disorders, the patient may become more physically active during the REM sleep stage. For example, patient 12 may involuntarily move his legs during the REM sleep stage or have other periodic limb movements. The physical activity of patient 12 may be disruptive to the patient's sleep, as well as to others around patient 12 when patient 12 is in the REM sleep stage. Accordingly, upon detecting a sleep stage associated with the REM sleep stage, DBS system 10 may select a therapy program that helps minimize the patient's movement.

In some examples, DBS system 10 may deliver stimulation to certain regions of brain 13, such as the locus coeruleus, dorsal raphe nucleus, posterior hypothalamus, reticularis pontis oralis nucleus, nucleus reticularis pontis caudalis, or the basal forebrain, during a sleep stage in order to help patient 12 fall asleep, maintain the sleep stage or maintain deeper sleep stages (e.g., REM sleep). The therapy delivery sites for therapy delivery during one or more sleep stages of patient 12 may be the same as or different from the therapy delivery sites used to deliver therapy to patient 12 to manage the patient's other condition (e.g., a neurological disorder). In addition to or instead of electrical stimulation therapy, a suitable pharmaceutical agent, such as acetylcholine, dopamine, epinephrine, norepinephrine, serotonine, inhibitors of noradrenaline or any agent for affecting a sleep disorder or combinations thereof may be delivered to brain 13 of patient 12. By alleviating the patient's sleep disturbances and improving the quality of the patient's sleep, patient 12 may feel more rested, and, as a result, DBS system 10 may help improve the quality of the patient's life.

IMD 16 includes a therapy module that includes a stimulation generator that delivers electrical stimulation therapy to patient 12 via electrodes 22A, 22B of leads 20A and 20B, respectively, as well as a processor that selects therapy parameter values (e.g., via selecting a therapy program or modifying a therapy program) based on a detected sleep stage of patient 12. In some examples, as described in further detail below, a processor of IMD 16 may determine the sleep stage patient 12 is in based on a frequency characteristic of one or more biosignals detected within brain 13 of patient 12 via electrodes 22A, 22B of leads 20A and 20B, respectively, or a separate electrode array that is electrically coupled to IMD 16 or a separate sensing device. In addition, in some examples, the biosignal may be detected from external electrodes that are placed on the patient's scalp to sense brain signals.

Examples of biosignals include, but are not limited to, electrical signals generated from local field potentials within one or more regions of brain 13, such as, but not limited to, an electroencephalogram (EEG) signal or an electrocorticogram (ECoG) signal. In some examples, the electrical signals within brain 13 may reflect changes in electrical current produced by the sum of electrical potential differences across brain tissue.

The biosignals that are detected may be detected within the same tissue site of brain 13 as the target tissue site for delivery of electrical stimulation. In other examples, the biosignals may be detected within another tissue site. For example, electrical stimulation may be delivered to the pedunculopontine nucleus (PPN), while biosignals may be detected within the primary visual cortex (e.g., Brodmann area 17) of brain 13. The PPN is located in the brainstem of brain 13, caudal to the substantia nigra and adjacent to the superior cerebellar peduncle. The PPN is a major brain stem motor area and may control gait and balance of movement, as well as muscle tone, rigidity, and posture of patient 12. The target therapy delivery site may depend upon the patient disorder that is being treated. In other examples, a biosignal may be detected within the thalamus, subthalamic nucleus, internal globus pallidus, or PPN of brain 13. In addition to or instead of deep brain sites, the biosignal may be detected on a surface of brain 13, such as between the patient's cranium and the dura mater of brain 13.

Electrical stimulation generated by IMD 16 may be configured to manage a variety of disorders and conditions. The therapy module within IMD 16 may produce the electrical stimulation in the manner defined by a therapy program that is selected based on the determined patient sleep stage. In some examples, the stimulation generator of IMD 16 is configured to generate and deliver electrical pulses to patient 12. However, in other examples, the stimulation generator of IMD 16 may be configured to generate a continuous wave signal, e.g., a sine wave or triangle wave. In either case, IMD 16 generates the electrical stimulation therapy for DBS according to a therapy program that is selected at that given time in therapy. In examples in which IMD 16 delivers electrical stimulation in the form of stimulation pulses, a therapy program may include a set of therapy parameter values, such as an electrode combination for delivering stimulation to patient 12, pulse frequency, pulse width, and a current or voltage amplitude of the pulses. The electrode combination may indicate the specific electrodes 22A, 22B that are selected to deliver stimulation signals to tissue of patient 12 and the respective polarity of the selected electrodes.

While the description of DBS system 10 is primarily directed to examples in which IMD 16 determines a sleep stage of patient 12 and selects a therapy program based on the determined stage, in other examples, a device separate from IMD 16, such as programmer 14, a sensing module that is separate from IMD 16 or another computing device, may determine the sleep stage of patient 12 and provide the indication to IMD 16. Furthermore, although IMD 16 may select a therapy program based on the determined sleep stage, in other examples, another device may select a therapy program based on the determined patient sleep stage, whether the patient sleep stage is determined by IMD 16 or a separate device, and input the therapy parameter values of the therapy program to IMD 16. Moreover, in some examples, IMD 16 or another device may select a therapy program group based on a detected sleep stage, where the therapy program group includes two or more therapy programs. The stimulation therapy according to the therapy programs of the group may be delivered simultaneously or on a time-interleaved basis, either in an overlapping or non-overlapping manner.

IMD 16 may be implanted within a subcutaneous pocket above the clavicle, or, alternatively, the abdomen, back or buttocks of patient 12. Implanted lead extension 18 is coupled to IMD 16 via connector 24. In the example of FIG. 1, lead extension 18 traverses from the implant site of IMD 16 and along the neck of patient 12 to cranium 26 of patient 12 to access brain 13. In the example shown in FIG. 1, leads 20A and 20B (collectively "leads 20") are implanted within the right and left hemispheres, respectively, of patient 12 in order deliver electrical stimulation to one or more regions of brain 13, which may be selected based on the patient condition or disorder controlled by DBS system 10. Other lead 20 and IMD 16 implant sites are contemplated. For example, IMD 16 may be implanted on or within cranium 26, in some examples. Or leads 20A, 20B may be implanted on the same hemisphere or IMD 16 may be coupled to a single lead. External programmer 14 wirelessly communicates with IMD 16 as needed to provide or retrieve therapy information.

Although leads 20 are shown in FIG. 1 as being coupled to a common lead extension 18, in other examples, leads 20 may be coupled to IMD 16 via separate lead extensions or directly to connector 24. Leads 20 may be positioned to deliver electrical stimulation to one or more target tissue sites within brain 13 to manage patient symptoms associated with the sleep impairment of patient 12, and, in some cases, a neurological disorder of patient 12, such as a movement disorder. In the example shown in FIG. 1, leads 20 are positioned to provide therapy to patient 12 to manage movement disorders and sleep impairment. Example locations for leads 20 within brain 13 may include the PPN, thalamus, basal ganglia structures (e.g., the globus pallidus, substantia nigra or subthalamic nucleus), zona inserta, fiber tracts, lenticular fasciculus (and branches thereof), ansa lenticularis, and/or the Field of Forel (thalamic fasciculus). Leads 20 may be implanted to position electrodes 22A, 22B (collectively "electrodes 22") at desired location of brain 13 through respective holes in cranium 26. Leads 20 may be placed at any location within brain 13 such that electrodes 22 are capable of providing electrical stimulation to target tissue sites within brain 13 during treatment. For example, in examples, electrodes 22 may be surgically implanted under the dura mater of brain 13 or within the cerebral cortex of brain 13 via a burr hole in cranium 26 of patient 12, and electrically coupled to IMD 16 via one or more leads 20.

Example techniques for delivering therapy to manage a movement disorder are described in U.S. Pat. No. 8,121,694 to Molnar et al., entitled, "THERAPY CONTROL BASED ON A PATIENT MOVEMENT STATE," which was filed on the same date as the present disclosure and issued on Feb. 21, 2012, U.S. Provisional No. 60/999,096 by Molnar et al., entitled, "DEVICE CONTROL BASED ON PROSPECTIVE MOVEMENT" and filed on Oct. 16, 2007, and U.S. Provisional No. 60/999,097 by Denison et al., entitled, "RESPONSIVE THERAPY SYSTEM" and filed on Oct. 16, 2007. The entire contents of above-identified U.S. Pat. No. 8,121,694 to Molnar et al., and U.S. Provisional Application Nos. 60/999,096 and 60/999,097 are incorporated herein by reference. In some examples described by U.S. Pat. No. 8,121,694 to Molnar et al. and U.S. Provisional Patent Application Ser. No. 60/999,096 by Molnar et al., brain signals are detected within a dorsal-lateral prefrontal (DLPF) cortex of a patient that are indicative of prospective movement of the patient. The signals within the DLPF cortex that are indicative of prospective patient movement may be used to control the delivery of movement disorder therapy, such as delivery of electrical stimulation, fluid delivery or a sensory cue (e.g., visual, somatosensory or auditory cue).

In some examples described by U.S. Pat. No. 8,121,694 to Molnar et al. and U.S. Provisional Patent Application Ser. No. 60/999,097 by Denison et al., a brain signal, such an EEG or ECoG signal, may be used to determine whether a patient is in a movement state or a rest state. The movement state includes the state in which the patient is generating thoughts of movement (i.e., is intending to move), attempting to initiate movement or is actually undergoing movement. The movement state or rest state determination may then be used to control therapy delivery. For example, upon detecting a movement state of the patient, therapy delivery may be activated in order to help the patient initiate movement or maintain movement, and upon detecting a rest state of the patient, therapy delivery may be deactivated or otherwise modified.

In the example shown in FIG. 1, electrodes 22 of leads 20 are shown as ring electrodes. Ring electrodes may be used in DBS applications because they are relatively simple to program and are capable of delivering an electrical field to any tissue adjacent to electrodes 22. In other examples, electrodes 22 may have different configurations. For examples, in some examples, electrodes 22 of leads 20 may have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed to a specific direction from leads 20 to enhance therapy efficacy and reduce possible adverse side effects from stimulating a large volume of tissue. In some examples, a housing of IMD 16 may include one or more stimulation and/or sensing electrodes. In alternative examples, leads 20 may be have shapes other than elongated cylinders as shown in FIG. 1. For example, leads 20 may be paddle leads, spherical leads, bendable leads, or any other type of shape effective in treating patient 12.

In the example shown in FIG. 1, IMD 16 includes a memory to store a plurality of therapy programs that each define a set of therapy parameter values. Upon determining a current sleep stage of patient 12, such as by determining the current sleep stage based on biosignals monitored within brain 13, IMD 16 may select a therapy program from the memory, where the therapy program is associated with the current sleep stage, and generate the electrical stimulation to manage the patient symptoms associated with the determined sleep stage. If DBS system 10 is configured to provide therapy during a plurality of patient sleep stages, each sleep stage may be associated with a different therapy program because different therapy programs may provide more effective therapy for a certain sleep stages compared to other therapy programs. Alternatively, two or more sleep stages may be associated with a common therapy program. Accordingly, IMD 16 may store a plurality of programs or programmer 14 may store a plurality of programs that are provided to IMD 16 via wireless telemetry.

During a trial stage in which IMD 16 is evaluated to determine whether IMD 16 provides efficacious therapy to patient 12, a plurality of therapy programs may be tested and evaluated for efficacy relative to one or more sleep stages. Therapy programs may be selected for storage within IMD 16 based on the results of the trial stage. During chronic therapy in which IMD 16 is implanted within patient 12 for delivery of therapy on a non-temporary basis, different therapy programs may be delivered to patient 12 based on a determined sleep stage of patient 12. As previously described, in some examples, IMD 16 may automatically determine the current sleep stage of patient 12 based on one or more biosignals, or may receive input from another device that automatically determines the sleep stage of patient 12. In addition, patient 12 may modify the value of one or more therapy parameter values within a single given program or switch between programs in order to alter the efficacy of the therapy as perceived by patient 12 with the aid of programmer 14. The memory of IMD 16 may store instructions defining the extent to which patient 12 may adjust therapy parameters, switch between programs, or undertake other therapy adjustments. Patient 12 may generate additional programs for use by IMD 16 via external programmer 14 at any time during therapy or as designated by the clinician.

Generally, IMD 16 is constructed of a biocompatible material that resists corrosion and degradation from bodily fluids. IMD 16 may comprise a hermetic housing to substantially enclose components, such as a processor, therapy module, and memory. IMD 16 may be implanted within a subcutaneous pocket close to the stimulation site. As previously described, although IMD 16 is implanted within a subcutaneous pocket above the clavicle of patient 12 in the example shown in FIG. 1, in other examples, IMD 16 may be implanted on or within cranium 26, within the patient's back, abdomen or any other suitable place within patient 12.

Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that provides information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device may run an application that enables the computing device to operate as medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20 and the electrode arrangement, the position of leads 20 within brain 13, the configuration of electrode array 22, initial programs defining therapy parameter values, and any other information the clinician desires to program into IMD 16. Programmer 14 may also be capable of completing functional tests (e.g., measuring the impedance of electrodes 22 of leads 20).

The clinician also may also store therapy programs within IMD 16 with the aid of programmer 14. During a programming session, the clinician may determine one or more therapy programs that may provide efficacious therapy to patient 12 to address symptoms associated with one or more different patient sleep stages. Patient 12 may provide feedback to the clinician as to the efficacy of the specific program being evaluated. Once the clinician has identified one or more therapy programs that may be efficacious in managing one or more sleep stages of patient 12, patient 12 may continue the evaluation process and identify, for each of the patient sleep stages, the one or more programs that best mitigate symptoms associated with the sleep stage. The evaluation of therapy programs may be completed after patient 12 wakes up. In some cases, the same therapy program may be applicable to two or more sleep stages. Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 need to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

DBS system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

Figure 2:
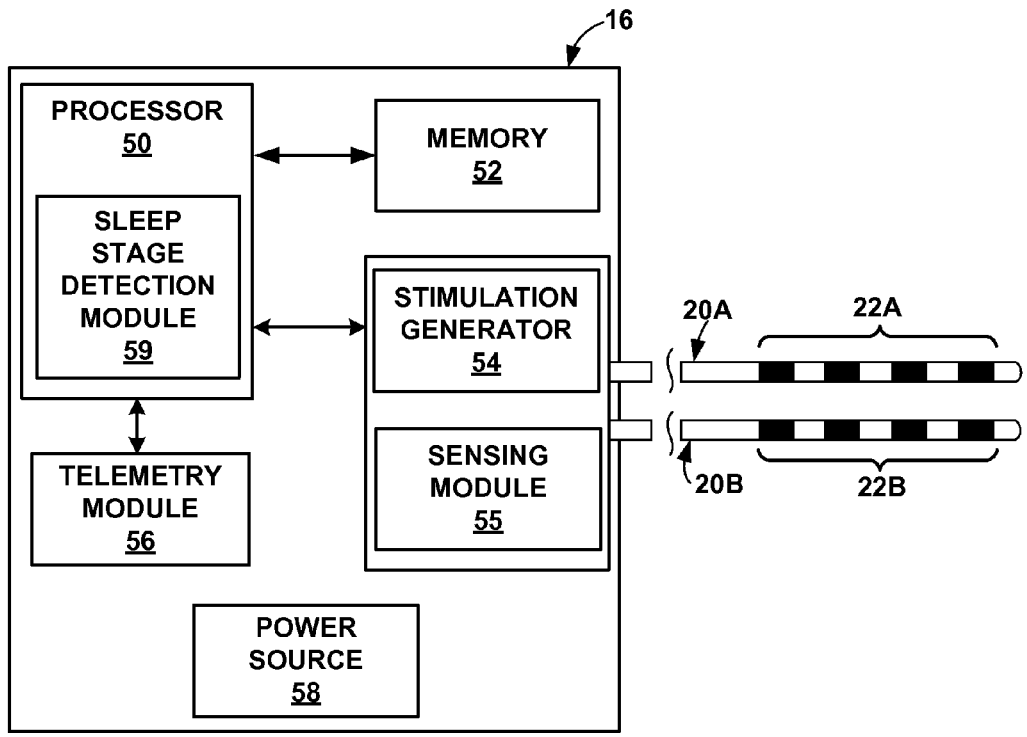
FIG. 2 is functional block diagram illustrating components of an example medical device.

FIG. 2 is a functional block diagram illustrating components of an example IMD 16. In the example shown in FIG. 2, IMD 16 generates and delivers electrical stimulation therapy to patient 12. IMD 16 includes processor 50, memory 52, stimulation generator 54, sensing module 55, telemetry module 56, power source 58, and sleep stage detection module 59. Although sleep stage detection module 59 is shown to be a part of processor 50 in FIG. 2, in other examples, sleep stage detection module 59 and processor 50 may be separate components and may be electrically coupled, e.g., via a wired or wireless connection.

Memory 52 may include any volatile or non-volatile media, such as a random access memory (RAM), read only memory (ROM), non-volatile RAM (NVRAM), electrically erasable programmable ROM (EEPROM), flash memory, and the like. Memory 52 may store instructions for execution by processor 50 and information defining therapy delivery for patient 12, such as, but not limited to, therapy programs or therapy program groups, information associating therapy programs with one or more sleep stages, thresholds or other information used to detect sleep stages based on biosignals, and any other information regarding therapy of patient 12. Therapy information may be recorded in memory 52 for long-term storage and retrieval by a user. As described in further detail with reference to FIG. 3, memory 52 may include separate memories for storing information, such as separate memories for therapy programs, sleep stage information, diagnostic information, and patient information. In some examples, memory 52 stores program instructions that, when executed by processor 50, cause IMD 16 and processor 50 to perform the functions attributed to them herein.

Processor 50 controls stimulation generator 54 to deliver electrical stimulation therapy via one or more leads 20. An example range of electrical stimulation parameters believed to be effective in DBS to manage a movement disorder of patient include:

1. Frequency: between approximately 100 Hz and approximately 500 Hz, such as approximately 130 Hz.
2. Voltage Amplitude: between approximately 0.1 volts and approximately 50 volts, such as between approximately 0.5 volts and approximately 20 volts, or approximately 5 volts. In other examples, a current amplitude may be defined as the biological load in the voltage is delivered.

3. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms.

4. Pulse Width: between approximately 10 microseconds and approximately 5000 microseconds, such as between approximately 100 microseconds and approximately 1000 microseconds, or between approximately 180 microseconds and approximately 450 microseconds.

Other ranges of therapy parameter values may also be useful, and may depend on the target stimulation site within patient 12, which may or may not be within brain 13. While stimulation pulses are described, stimulation signals may be of any form, such as continuous-time signals (e.g., sine waves) or the like. The therapy parameter values provided above may be useful for managing movement disorder symptoms of patient 12 when patient is not sleeping.

An example range of electrical stimulation parameters believed to be effective in DBS to manage symptoms present during a sleep state include:

1. Frequency: between approximately 0.1 Hz and approximately 500 Hz, such as between approximately 0.5 Hz and 200 Hz. In some cases, the frequency of stimulation may change during delivery of stimulation, and may be modified, for example, based on the sensed sleep stage or a pattern of sensed biosignals during the sleep state. For example, the frequency of stimulation may have a pattern within a given range, such as a random or pseudo-random pattern within a frequency range of approximately 5 Hz to approximately 150 Hz around a central frequency. In some examples, the waveform may also be shaped based on a sensed signal to either be constructive or destructive in a complete or partial manner, or phased shifted from about 0 degrees to about 180 degrees out of phase.

2. Amplitude: between approximately 0.1 volts and approximately 50 volts. In other examples, rather than a voltage controlled system, the stimulation system may control the current.

3. Pulse Width: between approximately 10 microseconds and approximately 5000 microseconds, such as between approximately 100 microseconds and approximately 1000 microseconds, or between approximately 180 microseconds and approximately 450 microseconds.

The electrical stimulation parameter values provided above, however, may differ from the given ranges depending upon the particular patient and the particular sleep stage (e.g., an awake state, Stage 1, Stage 2, Deep Sleep, or REM) occurring during the sleep state. For example, with respect to the sleep stage, the stimulation parameter values may be modified based on the sleep stage during which electrical stimulation is provided (e.g., an awake state, Stage 1, Stage 2, Deep Sleep or REM). As described in further detail below, in some examples, it may be desirable for stimulation generator 54 to deliver stimulation to patient 12 during the some sleep stages, and deliver minimal or no stimulation during other sleep stages.

In each of the examples described herein, if stimulation generator 54 shifts the delivery of stimulation energy between two therapy programs, processor 50 of IMD 16 may provide instructions that cause stimulation generator 54 to time-interleave stimulation energy between the electrode combinations of the two therapy programs, as described in commonly-assigned U.S. Pat. No. 7,519,431 to Steven Goetz et al., entitled, "SHIFTING BETWEEN ELECTRODE COMBINATIONS IN ELECTRICAL STIMULATION DEVICE," which was filed on Apr. 10, 2006 and issued on Apr. 14, 2009, the entire content of which is incorporated herein by reference. In the time-interleave shifting example, the amplitudes of the electrode combinations of the first and second therapy program are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off. Other techniques for shifting the delivery of stimulation signals between two therapy programs may be used in other examples.

Processor 50 may include any one or more of a microprocessor, a controller, a digital signal processor (DSP), an application specific integrated circuit (ASIC), a field-programmable gate array (FPGA), discrete logic circuitry, and the functions attributed to processor 50 herein may be embodied as firmware, hardware, software or any combination thereof. Sleep detection stage module 59 may determine a current sleep stage of patient 12. As described in further detail below, in some examples, sleep stage detection module 59 may be coupled to sensing module 55 that generates a signal indicative of electrical activity within brain 13 of patient 12, as shown in FIG. 2. In this way, sensing module 55 may detect or sense a biosignal within brain 13 of patient 12. Although sensing module 55 is incorporated into a common housing with stimulation generator 54 and processor 50 in FIG. 2, in other examples, sensing module 55 may be in a separate housing from IMD 16 and may communicate with processor 50 via wired or wireless communication techniques.

Example electrical signals include, but are not limited to, a signal generated from local field potentials within one or more regions of brain 13. EEG and ECoG signals are examples of local field potentials that may be measured within brain 13. However, local field potentials may include a broader genus of electrical signals within brain 13 of patient 12. Processor 50 may analyze the biosignal, e.g., a frequency characteristic of the biosignal, to determine the current patient sleep stage. A frequency characteristic of the biosignal may include, for example, a power level (or energy) within one or more frequency bands of the biosignal, a ratio of the power level in two or more frequency bands, a correlation in change of power between two or more frequency bands, a pattern in the power level of one or more frequency bands over time, and the like.

In examples, sleep stage detection module 59 (or, more generally, processor 50) may analyze the biosignal in the frequency domain to compare selected frequency components of an amplitude waveform of the biosignal to corresponding frequency components of a template signal or a threshold value. For example, one or more specific frequency bands may be more revealing of a particular sleep stage than others, and sleep stage detection module 59 may perform a spectral analysis of the biosignal in the revealing frequency bands. The spectral analysis of a biosignal may indicate the power level of each within each given frequency band over a range of frequencies.

In some examples, sleep stage detection module 59 may receive a signal from sensing module 55, which monitors a biosignal within brain 13 of patient 12 via at least some of the electrodes 22 or other electrodes. In one example, electrodes 22 (or other electrodes) may generate the signal indicative of brain activity, and sleep stage detection module 59 may receive the signal and analyze the signal to determine which, if any, sleep stage patient 12 is in. In addition to or instead of monitoring biosignals of patient 12 via electrodes coupled to at least one of leads 20, sleep stage detection module 59 may receive biosignals from electrodes coupled to another lead that is electrically coupled to sensing module 55, biosignals from electrodes coupled to an outer housing of IMD 16 and electrically coupled to sensing module 55, and/or biosignals from a sensing module that is separate from IMD 16.

Upon determining the patient's current sleep stage, sleep stage detection module 59 may generate a sleep stage indication. The sleep stage indication may be a value, flag, or signal that is stored or transmitted to indicate the current sleep stage of patient 12. In some examples, sleep stage detection module 59 may transmit the sleep stage indication another device, such as programmer 14, via telemetry module 56. In the example shown in FIG. 2, processor 50 may select a therapy program or modify a therapy program based on the sleep stage indication generated by sleep stage detection module 59 and control the delivery of therapy accordingly. Alternatively, processor 50 may select a therapy program from memory 52 (e.g., by selecting a stored therapy program or selecting instructions reflecting modifications to a stored therapy program) and transmit the selected therapy program to processor 50, which may then control stimulation generator 54 to deliver therapy according to the selected therapy program.

The "selected" therapy program may include, for example, the stored program selected from memory 52 based on the determined sleep stage, a stored therapy program and instructions indicating modifications to be made to a stored therapy program based on the determined sleep stage, a stored therapy program that has already been modified, or indicators associated with any of the aforementioned therapy programs (e.g., alphanumeric indicators associated with the therapy program). In some examples, processor 50 may record information relating to the sleep stage indication, e.g., the date and time of the particular patient state, in memory 52 for later retrieval and analysis by a clinician.

Processor 50 controls telemetry module 56 to send and receive information. Telemetry module 56 in IMD 16, as well as telemetry modules in other devices and systems described herein, such as programmer 14, may accomplish communication by RF communication techniques. In addition, telemetry module 56 may communicate with external medical device programmer 14 via proximal inductive interaction of IMD 16 with programmer 14. Accordingly, telemetry module 56 may send information to external programmer 14 on a continuous basis, at periodic intervals, or upon request from IMD 16 or programmer 14.

Power source 58 delivers operating power to various components of IMD 16. Power source 58 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
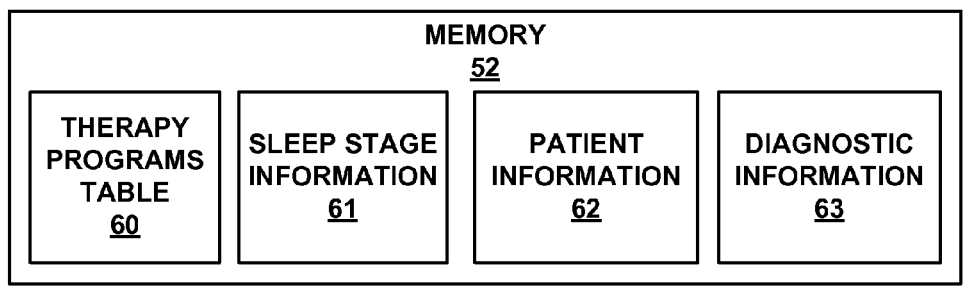
FIG. 3 is a block diagram illustrating an example configuration of a memory of a medical device.

FIG. 3 is a block diagram illustrating an example configuration of memory 52 of IMD 16. In the example of FIG. 3, memory 52 stores therapy programs table 60, sleep stage information 61, patient information 62, and diagnostic information 63. Therapy programs table 60 may store the therapy programs as a plurality of records that are stored in a table or other data structure that associates therapy programs with one or more sleep stages (e.g., Stage 1, Stage 2, Deep Sleep or REM) and/or frequency characteristics (e.g., threshold values or templates). While the remainder of the disclosure refers primarily to tables, the present disclosure also applies to other types of data structures that store therapy programs and associated physiological parameters.

In the case of electrical stimulation therapy, each of the programs in therapy programs table 60 may includes respective values for a plurality of therapy parameters, such as voltage or current amplitude, signal duration, frequency, and electrode configuration. Processor 50 of IMD 16 may select one or more programs from programs table 60 based on a sleep stage determined at least in part based on a biosignal sensed within brain 13 of patient 12. The therapy programs stored in the programs table 60 may be generated using programmer 14, e.g., during an initial or follow-up programming session, and received by processor 50 from programmer 14 via telemetry module 56. In other examples, programmer 14 may store programs 60, and processor 50 of IMD 16 may receive selected programs from programmer 14 via telemetry circuit 56.

Sleep stage information 61 may store information associating various sleep stage indicators, e.g., biosignals and, in some cases, a physiological signal indicative of a physiological parameter of patient 12 other than brain activity, with the respective sleep stage. For example, sleep stage information 61 may store a plurality of threshold values or templates, where each threshold value or template may correspond to at least one type of sleep stage. The threshold values may be, for example, threshold power levels within selected frequency bands that indicate a particular sleep stage, or values that are generated based on ratios of power between two or more frequency bands. The thresholds may be patient specific. The template may be, for example, a waveform template or a pattern in power levels of the biosignal within a selected frequency band over time. Sleep stage detection module 59 may reference sleep stage information 61 to determine, based on the threshold values or templates, whether a received biosignal is indicative of a particular sleep stage.

As described in further detail below, the threshold values may be threshold energy values for a particular patient sleep stage. If, for example, an energy level of a biosignal within a specific frequency band (e.g., about 10 Hz to about 30 Hz) is lower than the threshold value, sleep stage detection module 59 (or, more generally, processor 50) may determine that the biosignal indicates patient 12 is in the Stage 1 or Stage 2 sleep stages. As another example, if an energy level of a electrical signal within a specific frequency band (e.g., about 10 Hz to about 30 Hz), is greater than the threshold value, sleep stage detection module 59 may determine that the biosignal indicates patient 12 is in the Stage 1 or REM sleep stages.

In some examples, sleep stage detection module 59 (or, more generally, processor 50) may compare a frequency band component of a waveform template to the frequency band component of a biosignal from within brain 13 to determine whether the biosignal is indicative of a particular sleep stage. If, for example, an energy level of the waveform template within a specific frequency band (e.g., about 10 Hz to about 40 Hz) is substantially equal to or within a particular range (e.g., 1% to about 25%) of the energy level of the waveform template within the same frequency band, sleep stage detection module 59 may determine that the biosignal indicates patient 12 is in the sleep stage associated with the waveform template, i.e., that the biosignal is indicative of the particular sleep stage.

Patient information portion 62 of memory 52 may store data relating to patient 12, such as the patient's name and age, the type of IMD 16 or leads 20 implanted within patient 12, medication prescribed to patient 12, and the like. Processor 50 of IMD 16 may also collect diagnostic information 63 and store diagnostic information 63 within memory 52 for future retrieval by a clinician. Diagnostic information 63 may, for example, include selected recordings of the output of sensing module 55 or sleep stage indications generated by sleep stage module 59. In some examples, diagnostic information 63 may include information identifying the time at which the different sleep stages occurred. A clinician may later retrieve the information from diagnostic information 63 and determine a length of one or more of the patient's sleep stages based on this information.

Diagnostic information 63 may include other information or activities indicated by patient 12 using programmer 14, such as changes in symptoms, medication ingestion or other activities undertaken by patient 12. A clinician may review diagnostic information 63 in a variety of forms, such as timing diagrams or a graph resulting from statistical analysis of diagnostic information 63, e.g., a bar graph. The clinician may, for example, download diagnostic information 63 from IMD 16 via a programmer 14 or another computing device. Diagnostic information 63 may also include calibration routines for electrodes 20 (FIG. 1) and malfunction algorithms to identify stimulation dysfunctions.

Figures 4, 5:
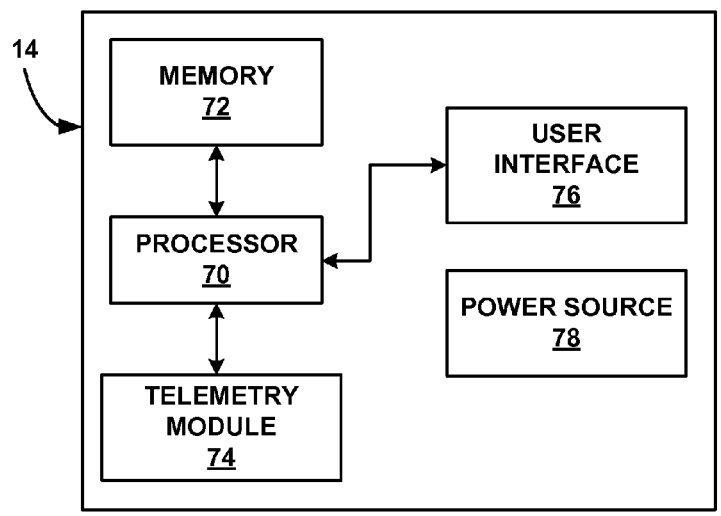
FIG. 4 illustrates an example therapy programs table that may be stored within a memory of a medical device.
FIG. 5 is a functional block diagram illustrating components of an example medical device programmer.

FIG. 4 illustrates an example therapy programs table 60 that may be stored within memory 52. Processor 50 may search table 60 to select a therapy program based on whether patient 12 is determined to be awake or asleep, and if patient 12 is determined to be asleep, the current sleep stage of patient 12 detected by sleep stage detection module 59. In particular, processor 50 may match a therapy program to the determined patient state and/or sleep stage and control stimulation generator 54 to deliver therapy according to the selected therapy program. The selected therapy program may be predetermined to provide therapeutic benefits to patient 12 when patient 12 is in the determined patient state and/or sleep stage associated with the selected therapy program.

As shown in FIG. 4, table 60 includes a plurality of records. Each record contains an indication of an awake state and various phases of the sleep state, i.e., a sleep stage. In particular, table 60 includes a plurality of records for the Stage 1, Stage 2, Deep Sleep, and REM sleep stages, as well as associated therapy programs. The indication of the awake state and sleep stages may be stored as, for example, a stored value, flag or other indication that is unique to the particular sleep stage. Thus, although table 60 shown in FIG. 4 shows the awake and sleep stages as "AWAKE," "STAGE 1," "STAGE 2," "DEEP SLEEP," or "REM," within memory 52, the therapy programs may be stored in another computer-readable format.

In examples in which sleep stage detection module 59 determines a current sleep stage of patient 12 based on an energy level within one or more frequency bands or a ratio of energy levels within two or more frequency bands of a monitored biosignal from brain 13 (FIG. 1), sleep stage indicators stored within table 60 may be threshold energy values, rather than the "AWAKE," "STAGE 1," "STAGE 2," "DEEP SLEEP," or "REM" indicators. Processor 50 may analyze the frequency component of the received biosignal and periodically compare the energy level or ratio of energy levels in two or more frequency bands to a value in table 60. Upon detecting a substantial match in the energy levels, processor 50 may select a therapy program that corresponds to the energy level. In some examples, an energy level that substantially matches the value stored in table 60 may be within, for example, within about 25% or less (e.g., about 10% or less) of the value stored in table 60. However, other sensitivity ranges for determining a substantial match between an energy level of a detected biosignal sensed within brain 13 and a value stored in table 60 are contemplated.

In examples in which sleep stage detection module 59 determines a current sleep stage based on a pattern in energy within one or more frequency bands over time, sleep stage indicators stored within table 60 may be stored waveform templates, rather than the "AWAKE," "STAGE 1," "STAGE 2," "DEEP SLEEP," or "REM" indicators. Processor 50 may analyze the frequency component of the received biosignal and periodically compare the energy levels in one or more frequency bands of the biosignal to the respective frequency components of the template waveform that is stored in table 60. Upon detecting a substantial match in energy pattern, processor 50 may select a therapy program that corresponds to the waveform template. An exact match between the energy pattern of the biosignal and template may not be necessary in some examples in order to detect the sleep stage associated with the template. In some examples, a biosignal that is determined to substantially match the template stored in table 60 may comprise an energy pattern that matches 75% or more of the energy pattern of the template stored in table 60. However, other sensitivity ranges for determining a substantial match between a template stored in table 60 and a detected biosignal are contemplated.

In the example of therapy programs table 60 shown in FIG. 4, the therapy parameter values of each therapy program are shown in table 60, and include values for a voltage amplitude, a pulse width, a pulse frequency, and an electrode configuration of an electrical stimulation signal. The amplitude is shown in volts, the pulse width is shown in microseconds (μs), the pulse frequency is shown in Hertz (Hz), and the electrode configuration determines the electrodes and polarity used for delivery of stimulation according to the record. The amplitude of program table 60 is the voltage amplitude, in Volts (V), but other examples of table 60 may store a current amplitude. In the illustrated example, each record includes a set of therapy parameter values, e.g., a therapy program, as therapy information. In other examples, each record may include one or more individual parameter values, or information characterizing an adjustment to one or more parameter values.

Different therapy programs may be more useful for providing effective therapy to patient 12 during a particular sleep stage when compared to other therapy programs. For example, different sets of electrodes may be activated to target different tissue sites depending on the sleep stage. Stimulation of a particular target tissue site within brain 13 may be more effective in managing symptoms of a sleep condition of patient 12 than another target tissue site. Thus, different electrode combinations may be selected to target different therapy delivery sites.

Processor 50 of IMD 16 or another device may dynamically control therapy delivery to patient 12 according to a determined sleep stage or a detection of the awake state. As an example, a first therapy program may be selected based on detection of a first sleep stage to help improve the performance of motor tasks by patient 12 that may otherwise be difficult. These tasks may include at least one of initiating movement or maintaining movement (e.g., to turn over in bed), which may be important during some sleep stages, such as the sleep stage associated with Stage 1 sleep. If patient 12 has a movement disorder, immobility or difficulty moving may cause patient 12 to wake up or have difficulty falling asleep.

As another example, a second therapy program may be selected based on detection of a second sleep stage to help limit movement of patient 12. As previously discussed, in some patients with movement disorders, the patient may become more physically active during the REM sleep stage, which may be disruptive, and, in some cases, dangerous to the patient's sleep or to others around patient 12. Accordingly, upon detecting the second sleep stage associated with the REM sleep stage, processor 50 may select a therapy program that helps minimize the patient's movement. In some examples, processor 50 of IMD 16 may select more than one therapy program to address a detected sleep stage. The stimulation therapy according to the multiple selected programs may be delivered simultaneously or on a time-interleaved basis, either in an overlapping or non-overlapping manner.

In other examples, rather than storing a plurality of parameter values for each therapy program, table 60 may store modifications to the values of different therapy parameters from a baseline or another stored therapy program. For example, if IMD 16 delivers stimulation to patient 12 at an amplitude of about 2 V, a pulse width of about 200 μs, a frequency of about 10 Hz, table 60 may indicate that upon detecting a Stage 1 sleep stage, processor 50 should control stimulation generator 54 to deliver therapy with a frequency of about 130 Hz, but maintain the values of the other stimulation parameters. The modification may be achieved by switching between stored programs or by adjusting a therapy parameter for an existing, stored program.

The modifications to parameter values may be stored in absolute or percentage adjustments for one or more therapy parameters or a complete therapy program. For example, in table 60 shown in FIG. 4, rather than providing an absolute amplitude value, "2.0V" in Record 1, the therapy programs table may indicate "+0.5 V" to indicate that if the Stage 1 sleep stage is detected, the amplitude of a baseline therapy program should be increased by 0.5 V or "−0.25 V" to indicate that if the REM sleep stage is detected, the amplitude should be decreased by 0.25 V. Instructions for modifying the other therapy parameters, such as pulse width, frequency, and electrode configuration, may also be stored in a table or another data structure that is stored within memory 52 of IMD 16 or another device, such as programmer 14.

In some examples, therapy delivery to patient 12 is stopped or reduced to a minimal intensity during one or more of the sleep stages, such as the Stage 2 and Deep Sleep stages. Intensity of stimulation may be a function of, for example, any one or more of the voltage or current amplitude value of the stimulation signal, frequency of stimulation signals, signal duration (e.g., pulse width in the case of stimulation pulses), signal burst pattern, and the like. The intensity of stimulation may, for example, affect the volume of tissue that is activated by the electrical stimulation. During the sleep stages in which therapy delivery is stopped or reduced in intensity, patient 12 may not consciously move as much as in other sleep stages and may not experience involuntary movements or at least experience minimal involuntary movements. Accordingly, therapy delivery during these sleep stages may not provide any added benefit if patient 12 has a movement disorder.

Deactivating therapy or decreasing the intensity of stimulation during these one or more sleep stages may help conserve power source 58 of IMD 16, which may help extend the useful life of IMD 16. Dynamically controlling therapy delivery to patient 12 based on a sleep stage may also help prevent patient 12 from adapting to therapy delivery by IMD 16. It has also been found that patient 12 may adapt to DBS provided by IMD 16 over time. That is, a certain level of electrical stimulation provided to brain 13 may be less effective over time. This phenomenon may be referred to as "adaptation." As a result, any beneficial effects to patient 12 from the DBS may decrease over time. While the electrical stimulation levels (e.g., amplitude of the electrical stimulation signal) may be increased to overcome such adaptation, the increase in stimulation levels may consume more power, and may eventually reach undesirable or harmful levels of stimulation. Delivering therapy to patient 12 according to different therapy programs during different sleep stages or even deactivating therapy delivery during some sleep stages may help decrease the rate at which patient 12 adapts to the therapy.

In therapy programs table 60 shown in FIG. 4, the therapy parameter values associated with the Stage 2 sleep stage indicate a relatively minimal stimulation intensity, while the therapy parameter values associated with the Deep Sleep stage indicate therapy is deactivated. The therapy parameter values shown in FIG. 4 are merely examples and are not intended to be representative of suitable therapy parameter values for each sleep stage. Suitable therapy parameter values for the different sleep stages may differ between patients 12, and, therefore, may trialing of different therapy programs prior to implementation of DBS system 10 on a chronic basis.

Although therapy programs table 60 is described with reference to memory 52 of IMD 16, in other examples, programmer 14 or another device may store different therapy programs and indications of the associated movement, sleep or patient state. The therapy programs and respective patient states may be stored in a tabular form, as with therapy programs table 60 in FIG. 4, or in another data structure.

FIG. 5 is a conceptual block diagram of an example external medical device programmer 14, which includes processor 70, memory 72, telemetry module 74, user interface 76, and power source 78. Processor 70 controls user interface 76 and telemetry module 74, and stores and retrieves information and instructions to and from memory 72. Programmer 14 may be configured for use as a clinician programmer or a patient programmer. Processor 70 may comprise any combination of one or more processors including one or more microprocessors, DSPs, ASICs, FPGAs, or other equivalent integrated or discrete logic circuitry. Accordingly, processor 70 may include any suitable structure, whether in hardware, software, firmware, or any combination thereof, to perform the functions ascribed herein to processor 70.

Processor 70 monitors activity from the input controls and controls the display of user interface 76. The user, such as a clinician or patient 12, may interact with programmer 14 through user interface 76. User interface 76 includes a display (not shown), such as an LCD or other type of screen, to show information related to the therapy and input controls (not shown) to provide input to programmer 14. Input controls may include buttons, a keypad (e.g., an alphanumeric keypad), a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display. In other examples, user interface 76 also includes audio circuitry for providing audible instructions or sounds to patient 12 and/or receiving voice commands from patient 12, which may be useful if patient 12 has limited motor functions.

In some examples, at least some of the control of therapy delivery by IMD 16 may be implemented by processor 70 of programmer 14. For example, in some examples, processor 70 may receive a biosignal from IMD 16 or from a sensing module that is separate from IMD 16, where the biosignal is sensed within brain 13 by IMD 16 or the sensing module that is separate from IMD 16. The separate sensing module may, but need not be, implanted within patient 12. In some examples, processor 70 may determine the current sleep stage of patient 12 based on the detected biosignal and may transmit a signal to IMD 16 via telemetry module 74, to indicate the determined sleep stage. For example, processor 70 may include a sleep stage detection module similar to sleep stage detection module 59 (FIG. 2) of IMD 16. Processor 50 of IMD 16 may receive the signal from programmer 14 via its respective telemetry module 56 (FIG. 3). Processor 50 of IMD 16 may select a stored therapy program from memory 52 based on the current sleep stage. Alternatively, processor 70 of programmer 14 may select a therapy program and transmit a signal to IMD 16, where the signal indicates the therapy parameter values to be implemented by IMD 16 during therapy delivery to help improve the patient's sleep quality, or may provide an indication of the selected therapy program that is stored within memory 52 of IMD 16. The indication may be, for example, an alphanumeric identifier or symbol that is associated with the therapy program in memory 52 of IMD 16.

Patient 12, a clinician or another user may also interact with programmer 14 to manually select therapy programs, generate new therapy programs, modify therapy programs through individual or global adjustments, and transmit the new programs to IMD 16. In a learning mode, programmer 14 may allow patient 12 and/or the clinician to determine which therapy programs are best suited for one or more specific sleep stages and for the awake patient state.

Memory 72 may include instructions for operating user interface 76, telemetry module 74 and managing power source 78. Memory 72 may also store any therapy data retrieved from IMD 16 during the course of therapy. The clinician may use this therapy data to determine the progression of the patient condition in order to predict future treatment. Memory 72 may include any volatile or nonvolatile memory, such as RAM, ROM, EEPROM or flash memory. Memory 72 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 74. Accordingly, telemetry module 74 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 78 delivers operating power to the components of programmer 14. Power source 78 may include a battery and a power generation circuit to produce the operating power. In some examples, the battery may be rechargeable to allow extended operation. Recharging may be accomplished electrically coupling power source 78 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 78 may include circuitry to monitor power remaining within a battery. In this manner, user interface 76 may provide a current battery level indicator or low battery level indicator when the battery needs to be replaced or recharged. In some cases, power source 78 may be capable of estimating the remaining time of operation using the current battery.

In some examples, processor 70 of programmer 14 or processor 50 of IMD 16 may monitor another physiological parameter of patient 12 in addition to the bioelectrical brain signal to confirm that patient 12 is in a sleep state or in a determined sleep stage. Examples of physiological parameters that may indicate a sleep state or sleep stage include, for example, activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response.

In some examples, processor 50 of IMD 16 or another device may confirm that patient 12 is asleep based on a physiological parameter of patient 12 other than bioelectrical brain signals or the biosignal (i.e., the bioelectrical brain signal) prior to initiating therapy delivery to patient 12 to help improve the patient's sleep quality. In one example, processor 50 of IMD 16 may determine values of one or more sleep metrics that indicate a probability of a patient being asleep based on the current value of one or more physiological parameters of the patient, as described in commonly-assigned U.S. Patent Application Publication No. 2005/0209512 by Heruth et al., which is entitled, "DETECTING SLEEP" and was filed on Apr. 15, 2004 and published on Sep. 22, 2005. U.S. Patent Application Publication No. 2005/0209512 by Heruth et al. is incorporated herein by reference in its entirety.

As described in U.S. Patent Application Publication No. 2005/0209512 by Heruth et al., a sensor that is incorporated with IMD 16 or a separate sensor may generate a signal as a function of at least one physiological parameter of a patient that may discernibly change when the patient is asleep. Examples of physiological parameters that may indicate a sleep stage include, for example, activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response. In some examples, processor 50 of IMD 16 may determine a value of a sleep metric that indicates a probability of the patient being asleep based on a physiological parameter. In particular, processor 50 may apply a function or look-up table to the current value and/or variability of the physiological parameter to determine the sleep metric value. Processor 50 may compare the sleep metric value to a threshold value to determine whether the patient is asleep. In some examples, the probability may be more than just an indication of "sleep state" or "awake state" but may include an indication of the chance, e.g., between 1% to about 100%, that patient 12 is in a sleep state.

Figure 6:
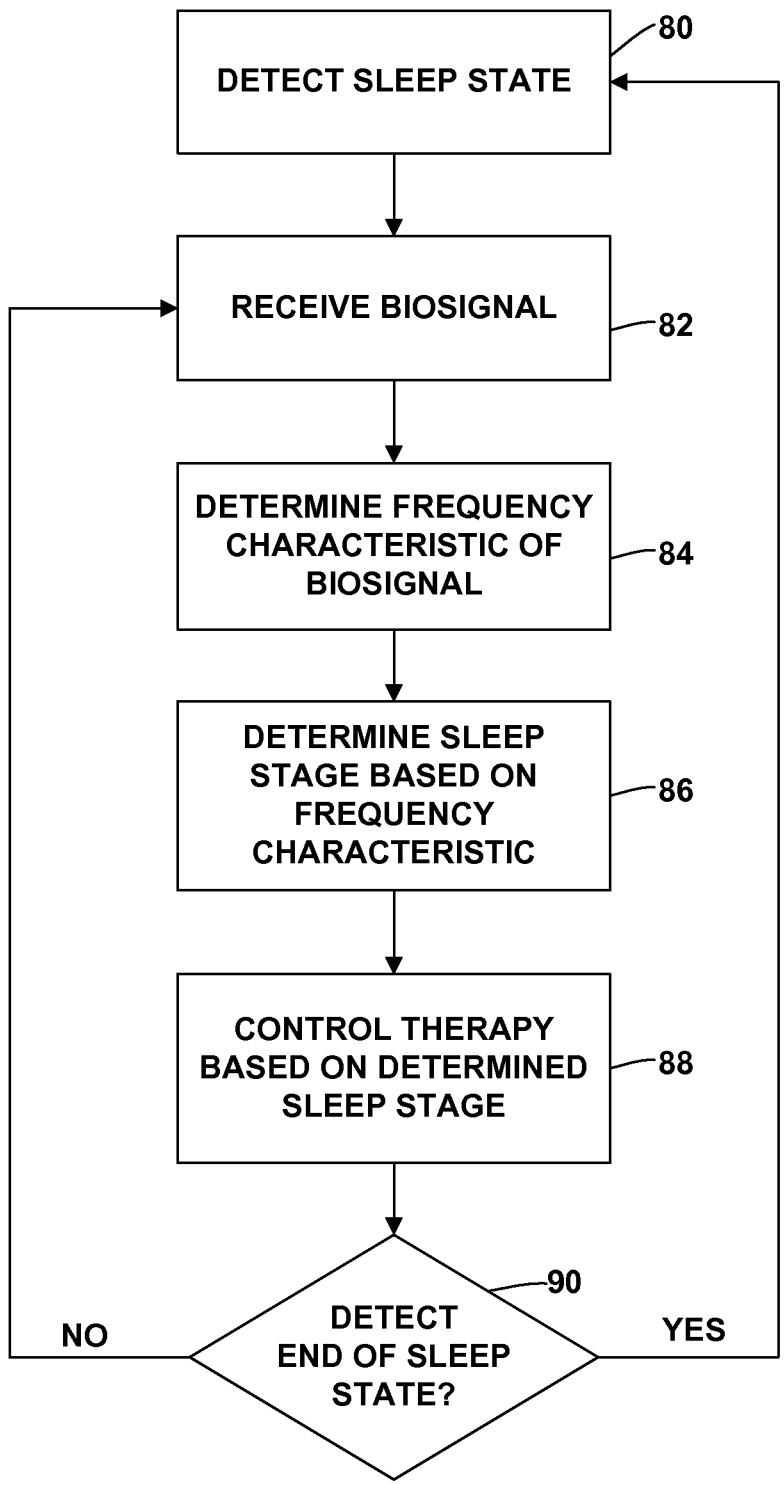
FIGS. 6 and 7 are flow diagrams illustrating example techniques for controlling therapy delivery to a patient based on a determined patient sleep stage.

FIG. 6 is a flow diagram illustrating an example technique for controlling therapy delivery by IMD 16 based on a determination of a sleep stage of patient 12. While FIG. 6, as well as other figures, such as FIGS. 7-18, 20, and 21, are described with reference to processor 50 of IMD 16, in other examples, a processor of another device, such as processor 70 of programmer 14 or a processor of a sleep stage detection module that is separate from IMD 16, may control therapy delivery by IMD 16 in accordance with the techniques described herein.

Processor 50 may determine whether patient 12 is in a sleep state (80) using any suitable technique. For example, patient 12 may provide input to programmer 14 via user interface 76 (FIG. 5) indicating patient 12 is commencing a sleep state (e.g., attempting to sleep). Patient 12 may also provide volitional cues indicating a beginning of a sleep state by providing input via a motion sensor, which then transmits a signal to processor 50. For example, patient 12 may tap a motion sensor in a different pattern to indicate patient 12 is in a sleep state. Examples of motion sensors are described below with reference to FIG. 21.

As other examples, processor 50 may determine patient 12 is in a sleep state by detecting a brain signal within brain 13 that is associated with a volitional patient input, where the brain signal is unrelated to the patient's symptoms or incidentally generated as a result of the patient's condition. Examples of volitional patient inputs are described in commonly-assigned U.S. Pat. No. 8,380,314 to Panken et al., entitled, "PATIENT DIRECTED THERAPY CONTROL," which was filed on Oct. 16, 2007 and issued on Feb. 19, 2013, and which is incorporated herein by reference in its entirety.

In another example, processor 50 may detect the sleep state based on values of one or more physiological parameters. For example, processor 50 may detect when patient 12 is in sitting or lying down based on a motion sensor or an accelerometer that indicates patient posture and determine patient 12 is in a sleep state upon detecting a relatively low activity level. In another example, processor 50 may detect the sleep state based on values of one or more sleep metrics that indicate a probability of patient 12 being asleep, such as using the techniques described in U.S. Patent Application Publication No. 2005/0209512 by Heruth et al. or commonly-assigned U.S. Pat. No. 7,491,181 to Heruth et al., entitled, "COLLECTING ACTIVITY AND SLEEP QUALITY INFORMATION VIA A MEDICAL DEVICE," which was filed on Apr. 15, 2004 and issued on Feb. 17, 2009, and is incorporated herein by reference in its entirety. The sleep metrics may be based on physiological parameters of patient 12, such as activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response.

As described in U.S. Patent Application Publication No. 2005/0209512, processor 50 may apply a function or look-up table to the current value and/or variability of the physiological parameter to determine the sleep metric value and compare the sleep metric value to a threshold value to determine whether patient 12 is asleep. In some examples, as described with reference to FIG. 20, processor 50 may compare the sleep metric value to each of a plurality of thresholds to determine the current sleep stage of patient 12, which may then be used to control therapy delivery in addition to the sleep stage determination based on the frequency band characteristic of the biosignal monitored within brain 13.

In addition to or instead of detecting a sleep state based on patient input or a physiological parameter of patient 12, processor 50 may detect the sleep state (80) based on a time schedule, which may be stored in memory 52 of IMD 16. The schedule may be selected by a clinician or IMD 16 may learn the schedule based on past patient inputs or other determinations. The schedule may set forth the times of a day in which patient 12 is typically in an awake state (e.g., not in a sleep state) and/or in a sleep state. For example, the schedule may be generated based on a circadian rhythm that is specific to patient 12. Processor 50 may track the time of day with a clock, which may be included as part of processor 50 or as a separate component within IMD 16. In some examples, processor 50 may automatically implement a clock based on a circadian rhythm of a typical patient, i.e., a generic circadian rhythm, rather than a circadian rhythm that is specific to patient 12.

In examples in which processor 50 detects a sleep state (80) based on a predetermined schedule, processor 50 may detect a sleep state at a first time (e.g., 10:00 p.m.) each night based on the schedule (or another time each night). Processor 50 may determine that the sleep state begins at the first time, at which time processor 50 may begin determining the patient sleep stage, as shown in FIG. 6, and ends at a second time (e.g., 8 a.m.), at which time processor 50 may revert to a different therapy control system or control stimulation generator 54 (FIG. 2) to deliver therapy to patient 12 according to a different therapy program (e.g., a therapy program that provides efficacious therapy to patient 12 in the awake state). The therapy control system that provides therapy when patient 12 is awake may, for example, provide substantially continuous therapy to patient 12 or provide therapy to patient 12 upon the detection of movement or an intent to move. Other techniques for detecting a sleep state are contemplated.

After detecting patient 12 is in a sleep state (80), processor 50 may receive biosignal (82), e.g., from sensing module 55 (FIG. 2) or a separate sensing module that senses the biosignal within brain 13 of patient 12. Sleep stage detection module 59, or, more generally, processor 50, may determine a frequency characteristic of the biosignal (84). In some examples, processor 50 may receive the biosignal prior to determining the sleep state, thus, the technique shown in FIG. 6 is not limited to receiving the biosignal after detecting the sleep state (80). In some examples, processor 50 may continuously receive the biosignal (82) from sensing module 55 (FIG. 2) or at periodic intervals, which may be set by a clinician. For example, processor 50 may periodically interrogate sensing module 55 to receive the biosignal (82). As another example, sensing module 55 may periodically transmit the biosignal to processor 50, such as at a frequency of about 0.1 Hz to about 100 Hz.

Sleep stage detection module 59 may determine a frequency characteristic of the biosignal (84) using any suitable technique. The frequency characteristic may include, for example, at least one of a power level (or energy) within one or more frequency bands of the biosignal, a ratio of the power level in two or more frequency bands, a correlation in change of power between two or more frequency bands, or a pattern in the power level of one or more frequency bands over time. In one example, sleep stage detection module 59 may comprise an amplifier that amplifies a received biosignal and a bandpass or a low pass filter that filters the monitored biosignal to extract one or more selected frequency bands of the biosignal. The extracted frequency bands may be selected based on the frequency band that is revealing of the one or more sleep stages that are being detected. Sleep stage detection module 59 may then determine the frequency characteristic based on the extracted frequency band component of the biosignal.

Different frequency bands are associated with different activity in brain 13. It is believed that some frequency band components of a biosignal from within brain 13 may be more revealing of particular sleep stages than other frequency components. One example of the frequency bands is shown in Table 1:

TABLE 1

Frequency bands

| Frequency (f) Band Hertz (Hz) | Frequency Information |
| --- | --- |
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

The frequency ranges for the frequency bands shown in Table 1 are merely examples. The frequency ranges may differ in other examples. For example, another example of frequency ranges for frequency bands are shown in Table 2:

TABLE 2

Frequency bands

| Frequency (f) Band Hertz (Hz) | Frequency Information |
| --- | --- |
| f < 5 Hz | δ (delta frequency band) |
| 5 Hz ≤ f ≤ 8 Hz | q (theta frequency band) |
| 8 Hz ≤ f ≤ 12 Hz | α (alpha frequency band) |
| 12 Hz ≤ f ≤ 16 Hz | s (sigma or low beta frequency band) |
| 16 Hz ≤ f ≤ 30 Hz | High β (high beta frequency band) |
| 50 Hz ≤ f ≤ 100 Hz | γ (gamma frequency band) |
| 100 Hz ≤ f ≤ 200 Hz | high γ (high gamma frequency band) |

Processor 50 may select a frequency band for determining the patient sleep stage using any suitable technique. In one example, the clinician may select the frequency band based on information specific to patient 12 or based on data gathered from more than one patient 12. The frequency bands that are useful for distinguishing between two or more different patient sleep stages or otherwise determining a patient sleep stage based on a biosignal from brain 13 may differ between patients. In some examples, a clinician may calibrate the frequency ranges to a specific patient based on, for example, a sleep study. During the sleep study, the clinician may monitor a biosignal and determine which, if any, frequency bands or ratio of frequency bands exhibit a characteristic that helps to detect a sleep stage and/or distinguish between different sleep stages.

Figure 7:
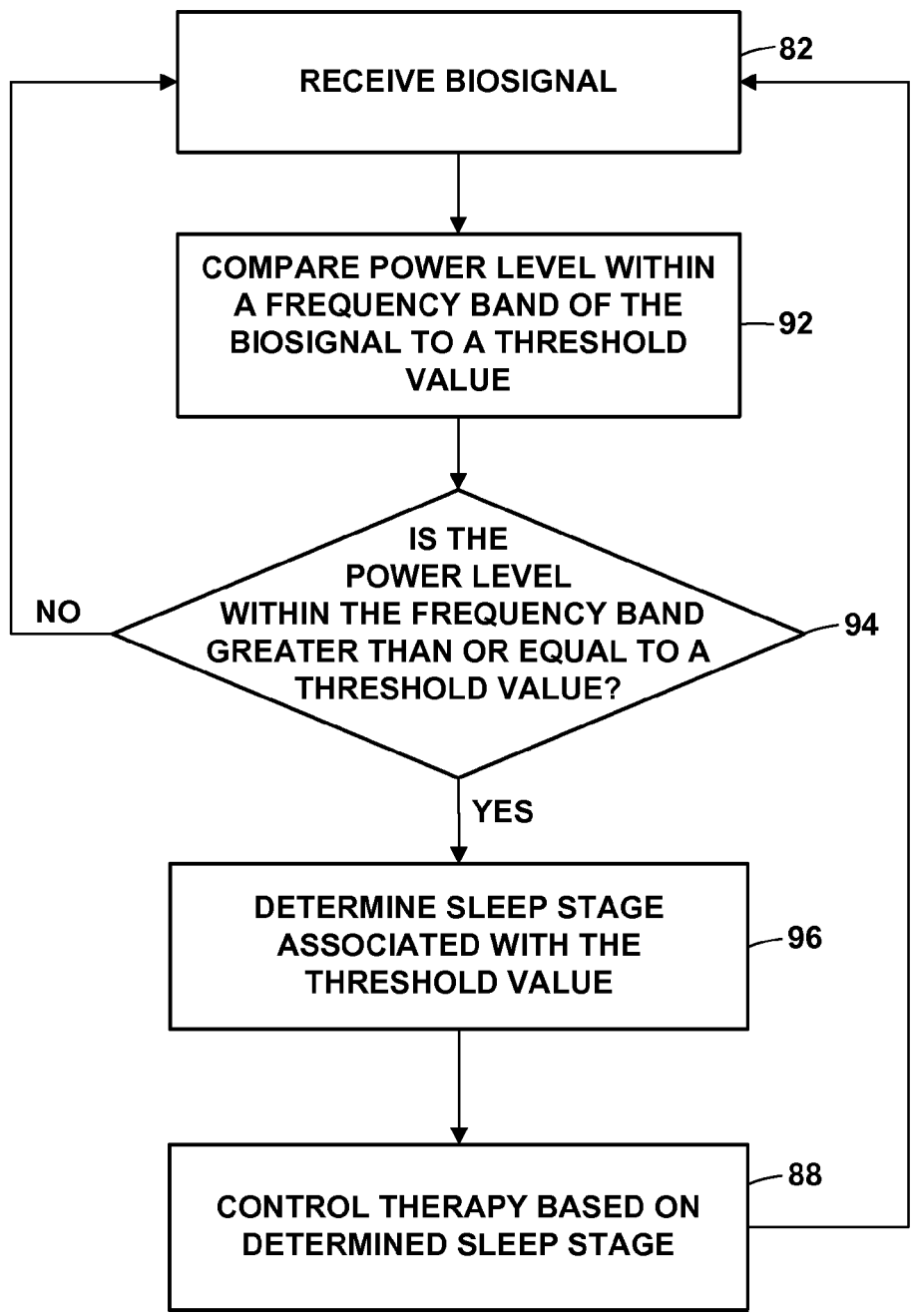
Figure 14:
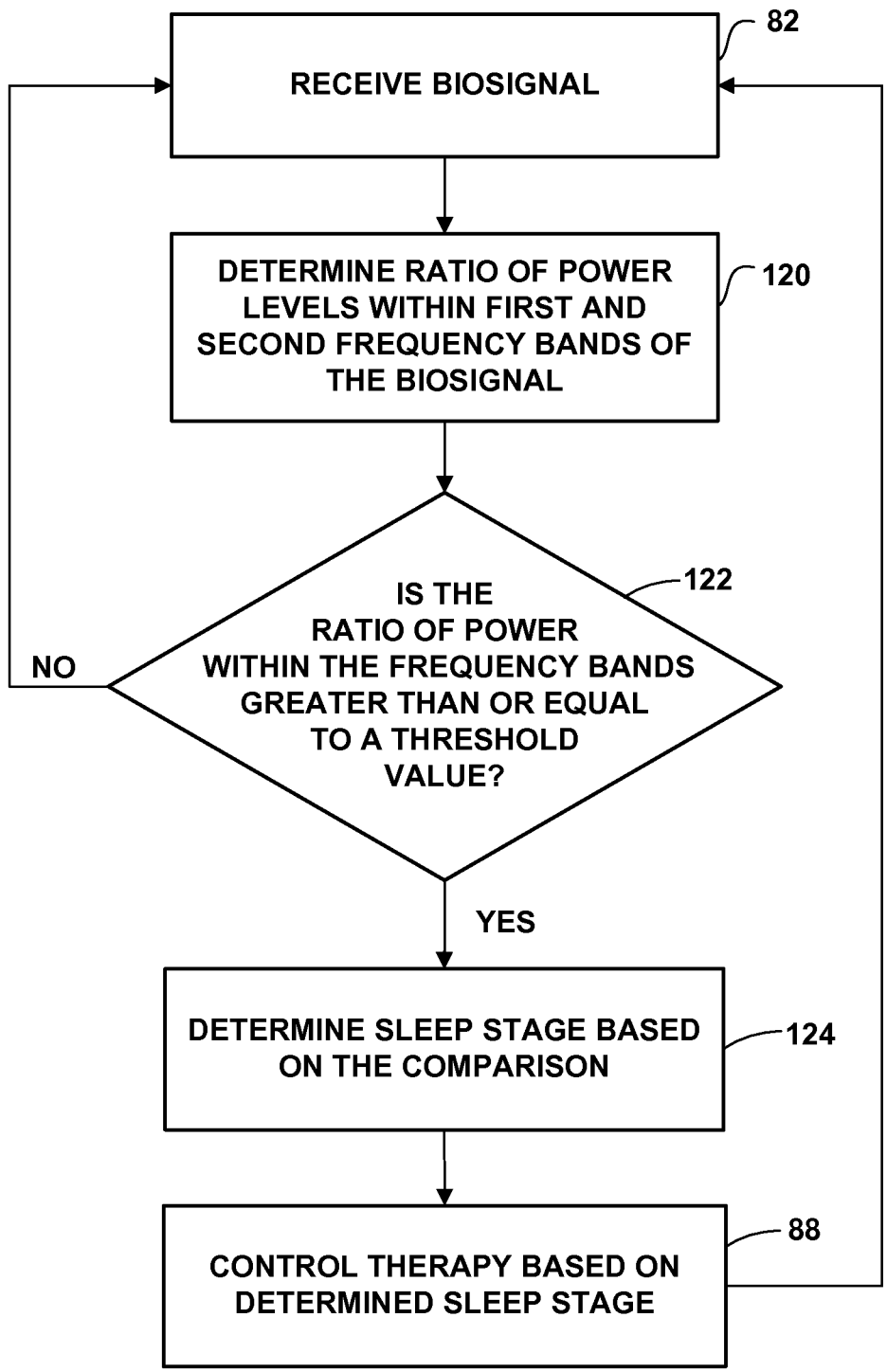
FIG. 14 is a flow diagram illustrating another example technique for controlling therapy delivery based on a determined patient sleep stage.

Sleep stage detection module 59 may determine a sleep stage based on the frequency characteristic of the biosignal (86). In some techniques, as shown in FIGS. 7 and 12, sleep stage detection module 59 may compare the frequency characteristic to one or more threshold values in order to determine the sleep stage or a sleep stage group that includes more than one sleep stage and is associated with a common therapy program. In other examples, as shown in FIG. 14, sleep stage detection module 59 may compare a trend in the power level within a frequency band of the biosignal over time to a template in order to determine the sleep stage.

After determining a sleep stage of patient 12 (86), processor 50 may control therapy delivery based on the determined sleep stage (88). For example, processor 50 may control stimulation generator 54 (FIG. 2) based on the determined sleep stage. In some examples, processor 50 may control therapy delivery by selecting a therapy program based on the determined sleep stage, e.g., using the therapy programs table 60 stored in memory 52 (FIGS. 3 and 4). In other examples, processor 50 may control therapy delivery by modifying a therapy program stored in memory 52 of IMD 16 (FIG. 2) based on the determined sleep stage. In addition, in some cases, processor 50 may deactivate therapy delivery, e.g., by stopping stimulation generator 54 from delivering stimulation signals to patient 12, in response to detecting a particular sleep stage. As described, for example, patient 12 that has a movement disorder may need minimal to no electrical stimulation therapy during some sleep stages (e.g., Stage 2 and Deep Sleep) of the sleep state.

Processor 50 may also determine whether the sleep state has ended (90) in order to, for example, revert to a different therapy program or revert to a different technique for controlling therapy delivery by IMD 16 when patient 12 is awake. In some examples, processor 50 may use techniques similar to those described above with respect to detecting the sleep state in order to determine whether the sleep state has ended. For example, a patient 12 may provide input to programmer 14 indicating the present patient state is an awake state and processor 70 of programmer 14 may transmit a signal to processor 50 to indicate that the sleep state has ended, e.g., because the awake state is the current patient state. In other examples, processor 50 may determine patient 12 is in an awake state or otherwise not in a sleep state based on the monitored biosignal and/or monitored physiological parameter values, such as a patient posture or activity level, as well as the other physiological parameters described above.

If the sleep state has ended (90), processor 50 may stop detecting the patient sleep stage until the sleep state is detected again (80). If the sleep state has not ended (90), processor 50 may continue monitoring the biosignal from brain 13 (82) and continue determining a sleep stage based on a frequency characteristic of the biosignal (84, 86) in order to control therapy (88).

FIG. 7 is a flow diagram illustrating another technique for controlling therapy delivery to patient 12 based on a determined sleep stage of patient 12. In accordance with the technique shown in FIG. 7, sleep stage detection module 59 may receive a biosignal (82) and compare a power level within a selected frequency band of the biosignal to a threshold value (92). The threshold value may be stored within memory 52 of IMD 16 or a memory of another device, such as programmer 14. The threshold value may indicate, for example, a power level that indicates patient 12 is in a particular sleep stage. Sleep stage detection module 59 may determine whether the power level within the frequency band is greater than or equal to the threshold value

(94) in order to determine whether patient 12 is in a particular sleep stage. In other examples (not shown in FIG. 4), sleep stage detection module 59 may determine whether the power level within the frequency band is less than or equal to the threshold value in order to determine whether patient 12 is in a particular sleep stage. The exact relationship between the power level of within the selected frequency band of the biosignal and the threshold value that indicates patient 12 is in a particular sleep stage may depend on the particular patient and the particular frequency band that is analyzed, among other factors.

In some examples, sleep stage detection module 59 may only be interested in detecting one sleep stage, and, accordingly, sleep stage detection module 59 may only compare power level within the frequency band of the biosignal to one threshold value. In other examples, sleep stage detection module 59 may detect two or more sleep stages, where each sleep stage may be associated with a different threshold value. Accordingly, in order to determine which sleep stage patient 12 is in, sleep stage detection module 59 may compare the power level within the frequency band of the biosignal to multiple threshold values. For example, sleep stage detection module 59 may first compare the power level within the selected frequency band of the biosignal to a first threshold value, which may correspond to a first sleep stage (e.g., Stage 1), followed by a comparison to a second threshold value, which may correspond to a second sleep stage that is different than the first sleep stage (e.g., Stage 2), and so forth for each relevant sleep stage. Sleep stage detection module 59 may cycle through the comparisons of the level within the frequency band of the biosignal at periodic intervals, such as at a frequency of about 0.1 Hz to about 100 Hz.

In other examples, sleep stage detection module 59 may detect two or more sleep stages, where at least two of the sleep stages are associated with a common threshold value. In accordance with one example, sleep stage detection module 59 may compare the power level within the selected frequency band of the biosignal to a threshold value and determine the sleep stage based on the comparison to the threshold and a clock. The clock may track the time that has passed since a previous sleep stage was detected. As previously discussed, each sleep stage has a typical duration, which may be used as a guide to determine which sleep stage is detected. Accordingly, if the power level of the biosignal within the selected frequency band is greater than or equal to (or, in some cases, less than or equal to) the threshold value, sleep stage detection module 59 may determine which sleep stage patient 12 is in based on the approximate time that has passed since the previous sleep stage was detected. If, for example, a first sleep stage that has a maximum duration of about 20 minutes is detected, and sleep stage detection module 59 subsequently determines that the power level of the biosignal within the selected frequency band is greater than or equal to a threshold value that is common to the first and second sleep stages, which occur sequentially, sleep stage detection module 59 may determine whether 20 minutes have passed since the first sleep stage was detected. If so, sleep stage detection module 59 may determine that patient 12 is in the second sleep stage of the sleep state. If the maximum duration of the first sleep stage has not passed sleep stage detection module 59 may determine that patient 12 is still in the first sleep stage.

In other examples, sleep stage detection module 59 may detect two or more sleep stages, where at least two of the sleep stages are associated with a common threshold value and a common therapy program. The two or more sleep stages may define a sleep stage group. Processor 50 may deliver therapy to patient 12 according to the same therapy program if patient 12 is in either of the two or more sleep stages. Accordingly, in some cases, processor 50 may not determine the specific sleep stage patient 12 is in, but may merely determine whether patient 12 is in the sleep stage group. After determining patient 12 is in the sleep stage group, processor 50 may control therapy delivery according to the therapy program associated with the sleep stage group.

If sleep stage detection module 59 determines that the power level within the selected frequency band is greater than or equal to the threshold value (94), sleep stage detection module 59 may determine that patient 12 is in the sleep stage associated with the threshold value (96). The threshold values may be associated with sleep stages in a look-up table or another data structure that is stored within memory 52. In some cases, as described above, sleep stage detection module 59 may merely determine that the biosignal indicates patient 12 is in a sleep stage group, and may not determine the specific sleep stage of patient 12. However, determination of a sleep stage group may generally be included within a sleep stage determination, as used herein. Processor 50 may control stimulation generator 54 or otherwise control therapy delivery to patient 12 based on the determined sleep stage (88). The determined sleep stage may be a specific sleep stage of patient 12 or may merely be one of a plurality of sleep stages that are associated with a common therapy program.

In some examples, different sleep stages may be distinguished from each other in different frequency bands. For example, a first frequency band may be more revealing of the difference between a first sleep stage and a second sleep stage, but may not be revealing of the difference between the second sleep stage and a third sleep stage. That is, in the first frequency band, the first and second sleep stages may be associated with different power levels, whereas the second and third sleep stages may be associated with the same power level. Accordingly, to distinguish between the second and third sleep stages, sleep stage detection module 59 may also analyze the biosignal in a second frequency band that is different than the first frequency band. In the second frequency band, the second and third sleep stages may have different power levels.

In these cases, in order to determine the sleep stage based on a biosignal, sleep stage detection module 59 may compare two or more frequency characteristics to respective threshold values. The two or more frequency characteristics may be, for example, power levels within respective frequency bands. The first frequency band and the first threshold value may be used to determine whether patient 12 is in the first sleep stage. If patient 12 is not in the first sleep stage, sleep stage detection module 59 may compare the second frequency characteristic in the second frequency band to the second threshold in order to determine whether patient 12 is in the second or third sleep stages. Sleep stage detection module 59 may compare the two or more frequency characteristics to respective thresholds substantially in parallel or sequentially.

FIG. 8 illustrates an example table that associates different patient states and sleep stages with threshold values and therapy programs. As previously indicated, in some cases, memory 52 may store data that associates two or more sleep stages with a common threshold value and a common therapy program, thereby defining a sleep stage group. The sleep stage group may represent a group of sleep stages for which therapy delivery according to the same therapy program provide efficacious therapy for sleep disorder symptoms associated with the sleep stages in the group. In FIG. 8, a patient awake state and two sleep stages (STAGE 1, and REM) are grouped together and associated with a first therapy program (PROGRAM A), and two sleep stages (STAGE 2 and DEEP SLEEP) are grouped together and associated with a second therapy program (PROGRAM B). Upon detecting a biosignal that has a power level within a selected frequency band that is greater than the threshold value, THRESHOLD A, processor 50 may control stimulation generator 54 to deliver therapy to patient 12 according to the parameter values defined by PROGRAM A. By selecting PROGRAM A based on the comparison of the power level of the biosignal within a selected frequency band, processor 50 may determine patient 12 is in at least one of the AWAKE state or the STAGE 1 or REM sleep stages.

On the other hand, upon detecting a biosignal that has a power level within a selected frequency band that is less than the threshold value, THRESHOLD A, processor 50 may control stimulation generator 54 to deliver therapy to patient 12 according to the parameter values defined by PROGRAM B. By selecting PROGRAM B based on the comparison of the power level of the biosignal within a selected frequency band, processor 50 may determine patient 12 is in at least one of the STAGE 2 or DEEP SLEEP stages.

In the example shown in FIG. 8, processor 50 may deliver therapy to patient 12 according to the same therapy program, regardless of whether patient 12 is an awake state (i.e., not in a sleep state) or in the Stage 1 or REM sleep stages. Accordingly, in some examples, in the technique shown in FIG. 7, processor 50 may not determine whether patient 12 is in a sleep state (80, FIG. 7) prior to receiving a biosignal and determining a frequency characteristic of a biosignal to determine a sleep stage of patient 12 to control therapy delivery. Further, in the technique shown in FIG. 7, in some examples, processor 50 may not detect the end of a sleep state (90, FIG. 7), but instead, may continually monitor the biosignal to determine whether what sleep stage patient 12 is in or whether patient 12 is in the awake state based on the frequency characteristic of the biosignal.

Activity within a beta band of the biosignal generated within brain tissue of patient 12 may be revealing of different sleep stages of patient 12. In particular, power levels within the beta band of the biosignal may be useful for determining a sleep stage of patient 12. As shown in FIG. 8, when patient is in an awake state, in Stage 1 or the REM sleep stage, the power level within the beta band of the biosignal may exceed a threshold (THRESHOLD A in FIG. 8). Thus, the beta band activity of the biosignal may be useful for distinguishing between the awake state of patient 12 and the Stage 2 and Deep Sleep stages of the sleep state, as well as between the Stage 1 and REM sleep stages and the Stage 2 and Deep Sleep stages. In some examples, the beta frequency band may include a frequency in a range of about 10 Hz to about 30 Hz, although other frequency ranges are contemplated. Furthermore, in some examples, the power levels that are compared to a threshold value may be within a subset of the beta frequency band, such as a frequency in a range of about 20 Hz to about 30 Hz. A "subset" may be, for example, a smaller range of frequencies within the particular frequency band.

As shown in FIG. 9, memory 52 of IMD 16 or a memory of another device may store data that associates different sleep stages with a threshold power level value in the alpha band frequency range, e.g., within therapy programs table 60 (FIG. 4). The alpha band may include, for example, a frequency in a range of about 8 Hz to about 14 Hz, although other frequency ranges are contemplated. For example, in other examples, the alpha band may include a frequency in a range of about 8 Hz to about 12 Hz or about 13 Hz. Further, in some examples, the power levels that are compared to a threshold value may be within a subset of the alpha frequency band, such as a frequency in a range of about 8 Hz to about 10 Hz.

As FIG. 9 illustrates, in some cases, the alpha band component of a biosignal useful for distinguishing between the awake state of patient 12 and the sleep state (e.g., Stage 1, Stage 2, Deep Sleep, and REM sleep stages). Upon detecting a biosignal that has a power level within the alpha band that is greater than the threshold value, THRESHOLD B, processor 50 may determine patient 12 is in a sleep state. The alpha band component of the biosignal may not be as useful for distinguishing between the different sleep stages as the beta band component. It may be useful to determine different threshold power values for two or more of the sleep stages in order to determine the sleep stage patient 12 is in based on the alpha band frequency component of the biosignal.

FIGS. 10A-10E are conceptual spectral power graphs, which illustrate the distribution of power (measured in microvolt (μV) squared) of a biosignal of a human subject during the awake state and various sleep stages. In the examples shown in FIGS. 10A-10E, the biosignal is a local field potential measured in the subthalamic nucleus of a human subject diagnosed with Parkinson's disease.

Figure 10A:
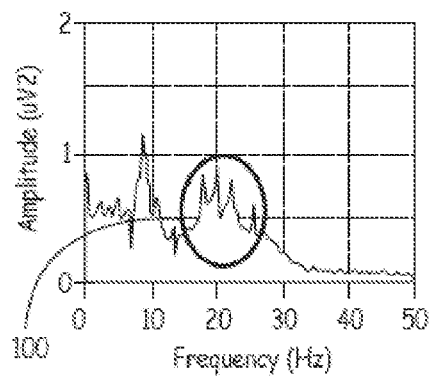
FIGS. 10A-10E are conceptual graphs illustrating power levels within different frequency bands for an awake state and different stages of a sleep state of a patient.
Figure 10B:
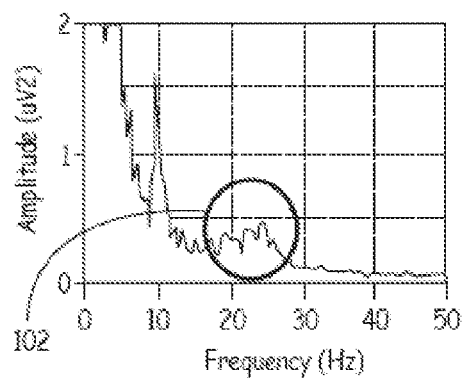
Figure 10C:
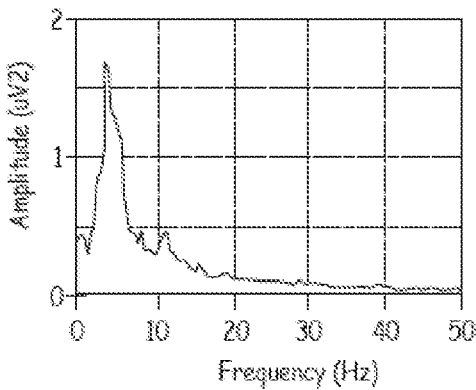
Figure 10D:
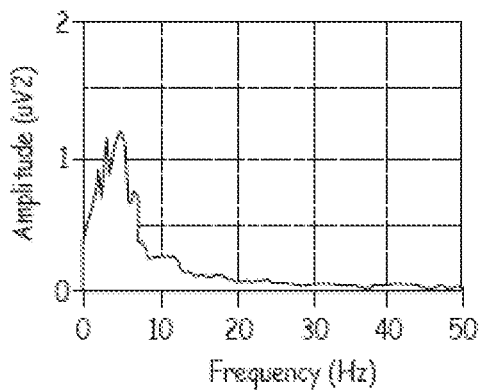
Figure 10E:
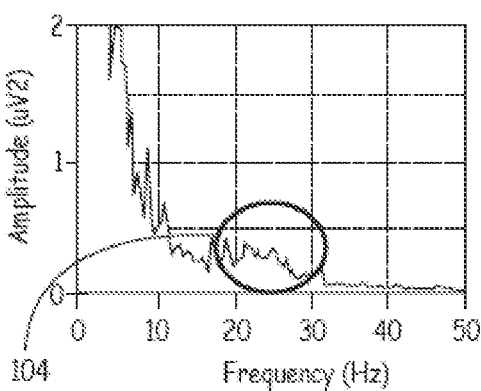

FIG. 10A is a spectral power graph of the biosignal during an awake state of the subject, i.e., when the subject was not asleep or attempting to sleep. FIG. 10B is a spectral power graph of the biosignal during Stage 1 of the sleep state. FIG. 10C is a spectral power graph of the biosignal during Stage 2 of the sleep state. FIG. 10D is a spectral power graph of the biosignal during a Deep Sleep stage of the sleep state. FIG. 10E is a spectral power graph of the biosignal during the REM stage of the sleep state.

As indicated by circle 100 in FIG. 10A, circle 102 in FIG. 10B, and circle 104 in FIG. 10E, spectral analysis of a biosignal of the Parkinson's subject indicates that oscillations in a frequency range of about 16 Hz to about 30 Hz during the awake stage, Stage 1, and REM sleep stages are relatively high, compared to the Stage 2 and Deep Sleep stages. That is, in the examples shown in FIGS. 10A-10E, the power level of the biosignal in a frequency band range of about 16 Hz to about 30 Hz was higher (as measured in microvolt (μV) squared) during the awake state (FIG. 10A), and Stage 1 (FIG. 10B) and REM sleep stages (FIG. 10E) compared to the Stage 2 (FIG. 10C) and Deep Sleep (FIG. 10D) sleep stages. Accordingly, it is believed that monitoring the beta band activity of a biosignal of a patient may be a useful for controlling therapy delivery during the awake stage, Stage 1, and REM sleep stages of a patient.

In some cases, the frequency range of about 16 Hz to about 30 Hz may be a part of the beta frequency band, although the frequency band designations may differ depending upon the standards used to categorize the frequency bands by different names.

As described above with respect to FIG. 7, processor 50 of IMD 16 may compare the power level within a beta band of a monitored biosignal to a threshold value, and if the power level exceeds the threshold value, processor 50 may control stimulation generator 54 (FIG. 2) to generate and deliver electrical stimulation signals to patient 12. Thus, processor 50 may control IMD 16 to deliver therapy to patient 12 when patient 12 is awake or in the sleep stage group comprising the Stage 1 or REM sleep stages by monitoring a power level within a beta band of a monitored biosignal. A frequency characteristic of a biosignal from within brain 13 of patient 12 that indicates activity within the about 16 Hz to about 30 Hz frequency range of the biosignal may be useful for delivering therapy during the awake state or Stage 1 and REM sleep stages according to a first therapy program, and deactivating or minimizing the intensity of therapy delivering during the Stage 2 or Deep Sleep stages of the sleep state.

Figure 11:
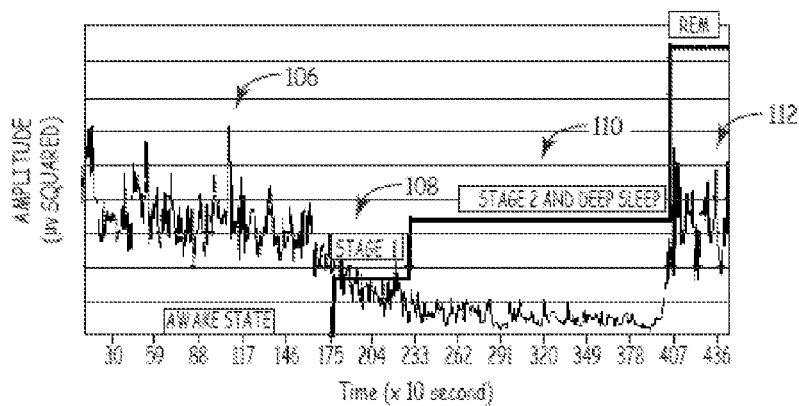
FIG. 11 is a conceptual graph illustrating a change in a power level of a biosignal within a particular frequency band over time.

FIG. 11 is a graph illustrating a change in a power level of a biosignal within the beta frequency band in a range of about 16 Hz to about 30 Hz over time. The biosignal used to generate the data shown in the graph of FIG. 11 may be a local field potential measured in the subthalamic nucleus of a human subject diagnosed with Parkinson's disease. As FIG. 11 illustrates, the energy (or power level) of the biosignal within the beta band is relatively high while patient is awake, as indicated by section 106 of the graph, and begins decreasing during Stage 1 of the sleep state, as indicated within section 108 of the graph. During Stage 2 and the Deep Sleep stages of the sleep state of the subject, the energy of the biosignal within the beta band is relatively low, as indicated by section 110 of the graph, and increases relatively quickly when patient 12 enters the REM sleep stage, as indicated by section 112 of the graph.

In examples in which processor 50 controls therapy delivery to patient 12 according to a different therapy program during the Stage 2 and Deep Sleep stages compared to the awake state and the Stage 1 and REM sleep stages, processor 50 may control stimulation generator 54 to switch therapy programs based on a half power point of the biosignal in the frequency band comprising a frequency range of about 16 Hz to about 30 Hz. A half power point may refer to the time at which the power level within a selected frequency band drops to half of a maximum power level. In FIG. 11, the maximum power level appears to occur during the awake state (106) or REM sleep stage (112). The biosignal in the graph of FIG. 11 decreases to the half power point or lower during the Stage 2 and Deep Sleep stages. Thus, the half power point may be a good indicator for when patient 12 switches from the Stage 1 sleep stage to the Stage 2 sleep stage, and from the Deep Sleep stage to the REM sleep stage.

FIGS. 12A-12D are conceptual graphs that illustrate waveforms of a biosignal sensed within a brain of a human subject over time during the awake state and various sleep stages. The amplitude of the biosignal is measured in microvolt (μV) in FIGS. 12A-12D. In the examples shown in FIGS. 12A-12D, the biosignal is a local field potential measured in the subthalamic nucleus of a human subject diagnosed with Parkinson's disease.

Figure 12A:
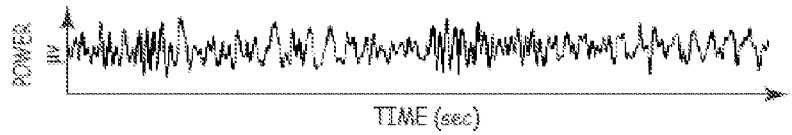
FIGS. 12A-12D are conceptual graphs that illustrate the distribution of power of a biosignal of a human subject over time during the awake state and various sleep stages.
Figure 12B:
Figure 12C:
Figure 12D:

FIG. 12A illustrates the waveform of the biosignal sensed within the brain of the subject during an awake stage of the subject. FIG. 12B illustrates waveform of the biosignal during Stage 1 sleep stage of the subject. FIG. 12C illustrates the waveform of the biosignal during Stage 2 and Deep Sleep stages of the subject. FIG. 12D illustrates the waveform of the biosignal during REM sleep stage of the subject.

FIGS. 12A-12D suggest that the biosignal had more activity within a frequency range of about 20 Hz to about 25 Hz of a beta frequency band during the awake state, Stage 1 sleep stage, and REM sleep stage compared to the Stage 2 and Deep Sleep stages of the subject. Again, this suggests that the beta band of a biosignal may be useful for determining when patient is in the awake state, Stage 1 sleep stage, and REM sleep stage in order to deliver therapy to patient during the awake state, Stage 1 sleep stage, and REM sleep stage or least detect the awake state, Stage 1 sleep stage, and REM sleep stage compared to the Stage 2 and Deep Sleep stages.

Figure 13:
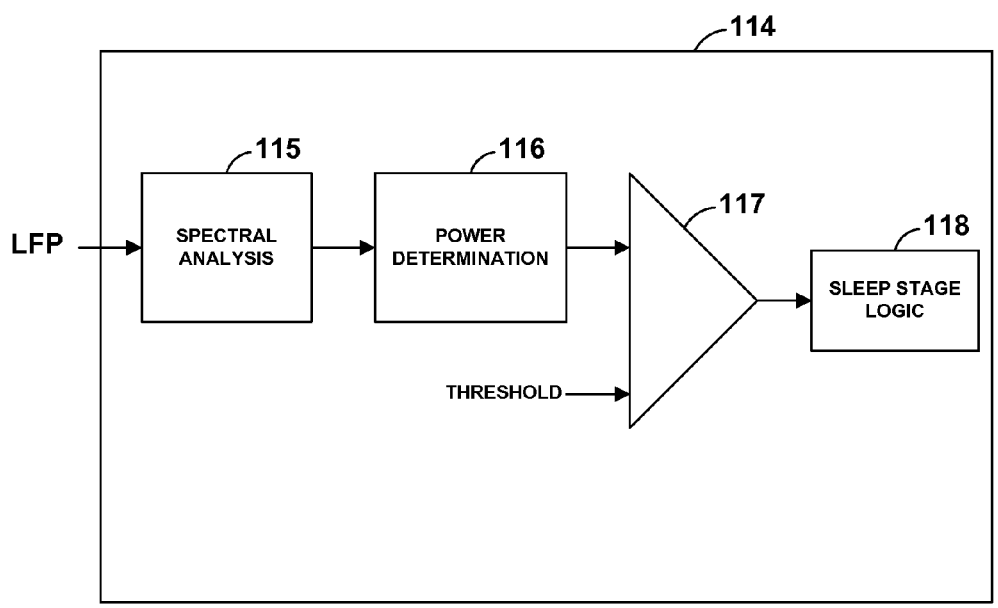
FIG. 13 is a logic diagram illustrating an example circuit that determines a sleep stage from a biosignal that is generated based on local field potentials (LFP) within a brain of a patient.

FIG. 13 is a logic diagram illustrating an example circuit that may be used to determine a sleep stage of patient 12 from a biosignal that is generated based on local field potentials (LFP) within brain 13 of patient 12. Module 114 may be integrated into sleep stage detection module 59 of IMD 16 (FIG. 2) or a processor of another device, such as processor 70 of programmer 14 (FIG. 5). A local field potential (LFP) detected by electrodes 22 of leads 20 or another set of electrodes may be transmitted into module 114 and provided to spectral analysis submodule 115, which extracts the frequency components of the local field potential signal, such as by implementing a fast Fourier transform algorithm. Although not shown in FIG. 13, in some examples, the local field potential signal may be provided to an amplifier prior to being sent to spectral analysis submodule 115. In other examples, a bandpass filter may be used to allow the frequencies of a selected frequency band.

After passing through spectral analysis submodule 115, the local field potential biosignal may pass through a power determination submodule 116, which may determine a power of the local field potential signal in a selected frequency band, which may be, for example a beta band (e.g., about 10 Hz to about 30 Hz). The extracted power level of the local field potential signal outputted by power determination submodule 116 may be sent to comparator 117, along with a threshold value, which may be provided by processor 50. As indicated above, the threshold value may be specific to a particular sleep stage or a group of sleep stages. Comparator 117 may compare the threshold value and the power determined by power determination submodule 116, e.g., to determine whether the power determined is greater than or equal to, or, in some cases, less than or equal to the threshold value.

The signal from comparator 117 may be indicative of a sleep stage or a group of sleep stages of patient 12. Sleep stage logic 118 may determine the patient sleep stage based on the signal from comparator 117 and generate a sleep stage indication indicating that patient 12 may be within the determined sleep stage. Processor 50 may then take an action associated with the sleep stage indication, such as by referencing a look-up table (e.g., table 60 in FIG. 4). The look-up table may specify actions such as selecting a therapy program, activating or deactivating therapy delivery to patient 12 or modifying a therapy program. Processor 50 may control stimulation generator 54 (FIG. 2) to deliver therapy to patient 12 in accordance with the selected or modified therapy program.

In some examples, sleep stage logic 118 may include duration logic that determines whether a power level of the biosignal within a selected frequency band or a ratio of power levels within two or more selected frequency bands is greater (or less and, in some cases equal to) than a stored threshold value for a predetermined amount of time. If sleep stage logic 118 determines that the power level or ratio of power levels is greater than or equal to the stored threshold value for the predetermined amount of time, sleep stage logic 118 may determine that patient 12 is in the sleep stage associated with the threshold value. In other examples, sleep stage logic 118 may include duration logic that determines whether a power level of the biosignal within a selected frequency band or a ratio of power levels within two or more selected frequency bands is less than or equal to a stored threshold value for a predetermined amount of time.

In some examples, different channels may be used to monitor power within different frequency bands and compare the power in the different frequency bands to respective threshold values. In examples in which a bandpass filter is used to extract the relevant frequency band components, each channel may have a respective bandpass filter, and, in some cases, a full-wave rectifier. The bandpass filter of each channel may allow frequencies in different ranges. Each channel may include a respective amplifier and bandpass filter or a common amplifier may amplify the LFP signal prior to spectral analysis submodule 115. After bandpass filtering of the local field potential signal (or other biosignal), the filtered signals may be similarly processed in parallel before being delivered to sleep stage logic module 118. Multiple channels may be useful when some sleep stages are easier to distinguish from another sleep stage in different frequency bands.

FIG. 14 is a flow diagram illustrating another example technique for controlling therapy delivery based on a frequency band characteristic of a biosignal from brain 13 of patient 12. Processor 50 of IMD 16 may receive a biosignal (82), e.g., from sensing module 55 (FIG. 2), which may be in the same or a different housing than IMD 16. Sleep stage detection module 59 may determine a ratio of power levels within at least a first and second frequency band (120). The ratio may be, for example, a value determined by dividing a first power level of the biosignal within the first frequency band by a second power level of the biosignal within the second frequency band. The frequency bands that are selected to determine the ratio may be, for example, frequency bands that have been determined, e.g., by a clinician or others, to be revealing of the different sleep stages of patient 12 or at least revealing of the differences between groups of sleep stages. In some examples, the groups of sleep stages may include a first group in which therapy delivery during the sleep stages of the first group is desirable, and a second group in which therapy delivery during the sleep stages of the second group is not desirable or is minimal.

In general, determining a sleep stage of patient 12 based on a ratio of power levels within two frequency bands of the biosignal may be useful because of the more robust nature of the ratio, which considers activity in two frequency bands. In some cases, a power level within a single frequency band may be relatively small (e.g., on the order of microvolts), which may be difficult to measure with relatively accuracy and precision. Determination of a frequency characteristic that includes a ratio of power levels may help generate a value that is more indicative of the activity within the frequency bands, irrespective of the relatively small power values. For example, determination of a frequency characteristic that includes a ratio of power levels may help correlate the change in power in one frequency band to a change in power in another frequency band, which may be more revealing of the sleep stage of patient 12. In addition, depending on the selected frequency bands, different power ratios may be useful for distinguishing between different subsets of sleep stages.

In the example shown in FIG. 14, sleep stage detection module 59 compares the ratio of powers within the selected frequency bands to a threshold value (122). If the ratio is less than the threshold value, processor 50 may continue monitoring the biosignal (82) without controlling therapy delivery. For example, stimulation generator 54 (FIG. 2) may not deliver any therapy to patient 12 if the ratio of the power levels within the first and second selected frequency bands is less than the threshold value.

If sleep stage detection module 59 determines that the ratio of the power levels within the first and second selected frequency bands is greater than or equal to the threshold value (122), sleep stage detection module 59 may determine that patient 12 may be in the sleep stage associated with the threshold value (124). Again, sleep stages or sleep stage groups may be associated with threshold values in a look-up table or data structured stored within memory 52 of IMD 16 or a memory of another device. In some examples, sleep stage detection module 59 may determine a group of sleep stages based on the comparison, particularly if the threshold value is associated with more than one sleep stage. Processor 50 may control stimulation generator 54 (FIG. 2) of IMD 16 based on the determined sleep stage (88), such as by selecting a therapy program that is associated with the sleep stage.

In other examples, processor 50 may not directly determine the sleep stage, but may indirectly determine the sleep stage by selecting a therapy program based on the comparison between the ratio of power levels and the threshold value, and controlling the therapy delivery based on the selected therapy program (88). As previously indicated, in some examples, processor 50 may not determine a specific sleep stage associated with the threshold value, but may merely determine a therapy program or therapy program modification based on the threshold value. In this way, processor 50 may effectively determine the sleep stage without determining the specific name of the sleep stage that has been detected.

In other examples of the technique shown in FIG. 14, sleep stage detection module 59 may determine whether the ratio of power levels within the first and second selected frequency bands is less than or equal to the threshold value in order to determine whether patient 12 is in a particular sleep stage. Thus, in some cases, stimulation generator 54 (FIG. 2) may not deliver any therapy to patient 12 if the ratio of the power levels within the first and second selected frequency bands is greater than the threshold value.

FIGS. 15A-15C are example tables that associates an awake state and different sleep stages of a sleep state with threshold values and therapy programs. The tables or the data within the tables shown in FIGS. 15A-15C may be stored within memory 52 of IMD 16 (e.g., within therapy programs table 60) or a memory of another device, such as programmer 14. As shown in FIGS. 15A-15C, in some cases, a common therapy program may be associated with one or more sleep stages and/or the awake state of patient 12. Processor 50 may receive a biosignal generated within brain 13 of patient 12 and determine a frequency characteristic of the biosignal in order to determine whether patient 12 is generally in a sleep stage group, rather than determining the specific sleep stage of patient 12. Upon determining patient 12 is in a sleep stage group, processor 50 may control IMD 16 to deliver therapy to patient 12 based on the determination that patient is generally in one of a plurality of sleep stages that are grouped together. For example, processor 50 may select the therapy program associated with the group and control IMD 16 to deliver therapy to patient 12 according to the selected therapy program.

FIG. 15A illustrates a table that may be used to compare a ratio of power between a sigma band and a beta band of a biosignal of patient 12 to a common threshold value (THRESHOLD C in FIG. 15A) in order to select a therapy program for controlling therapy delivery to patient 12 by IMD 16. As previously indicated, activity within a beta band of the biosignal generated within brain tissue of patient 12 may be revealing of different sleep stages of patient 12. The ratio of power levels within different subsets of the beta band may also be useful for determining a sleep stage of patient 12. For example, a ratio of power within the sigma band, which may refer to a relatively low beta band, and the high beta band may be useful for distinguishing between different sleep stages or groups of sleep stages. In some examples, the sigma band may be in a range of about 12 Hz to about 16 Hz, although other frequency ranges are contemplated for the sigma band. In some examples, the high beta band may be in a range of about 16 Hz to about 30 Hz, although other frequency ranges are contemplated for the high beta band.

Based on the data shown in the table of FIG. 15A, a patient awake state and two sleep stages (STAGE 1 and REM) are grouped together and associated with a first therapy program (PROGRAM C), and two sleep stages (STAGE 2 and DEEP SLEEP) are grouped together and associated with a second therapy program (PROGRAM C). Upon detecting a biosignal that has a ratio of power levels within the sigma band and high beta band that is greater than the threshold value, THRESHOLD C, processor 50 may control stimulation generator 54 to generate and deliver therapy to patient 12 according to the parameter values defined by PROGRAM C. By selecting PROGRAM C based on the comparison of the ratio of power levels within the selected frequency bands, processor 50 may determine patient 12 is in at least one of the AWAKE state or the STAGE 1 or REM sleep stages.

On the other hand, upon detecting a biosignal that has a ratio of power levels in the sigma band and beta band that is less than the threshold value, THRESHOLD C, processor 50 may control stimulation generator 54 to generate and deliver therapy to patient 12 according to the parameter values defined by PROGRAM D. By selecting PROGRAM D based on the comparison of the ratio of power levels within the selected frequency bands, processor 50 may determine patient 12 is in a sleep stage group including the STAGE 2 and DEEP SLEEP stages.

Just as in the example table shown in FIG. 8, when processor 50 references the table shown in FIG. 15A to determine a patient sleep stage, processor 50 may control stimulation generator 54 to generate and deliver therapy to patient 12 according to the same therapy program, regardless of whether patient 12 is an awake state (i.e., not in a sleep state) or in the Stage 1 or REM sleep stages. As FIG. 15A indicates, the presence of a relative low ratio of a sigma band power to a high beta band power, as indicated by a value less than THRESHOLD C, may be a marker for a transition from Stage 2 sleep to REM sleep.

FIG. 15B illustrates a table that may be used to compare a ratio of power in a beta band and an alpha band of a biosignal of patient 12 to two threshold values (THRESHOLD D and THRESHOLD E in FIG. 15B) in order to select a therapy program for controlling therapy delivery to patient 12 by IMD 16. In some examples, the alpha band may be in a range of about 5 Hz to about 10 Hz, although other frequency ranges are contemplated for the alpha band. In some examples, the beta band may be in a range of about 10 Hz to about 30 Hz, although other frequency ranges are contemplated for the beta band. In addition, the ratio of power between a beta band and an alpha band of the biosignal may include a ratio of power between a subset of the beta band and a subset of the alpha band.

As FIG. 15B illustrates, the ratio of power between the beta band and alpha band may be useful for distinguishing between the awake state of patient 12 and Stage 2, Deep Sleep, and REM sleep stages of patient 12. In addition, the beta band power and alpha band power ratio may be useful for distinguishing between the Stage 1 sleep stage of patient 12 and the Stage 2, Deep Sleep, and REM sleep stages of patient 12. Further, the beta band power and alpha band power ratio may be useful for distinguishing between the REM sleep stage of patient 12 and the awake state, Stage 1, and Deep Sleep stages of patient 12.

Based on the data shown in the table of FIG. 15B, a patient awake state and the STAGE 1 sleep stage are grouped together and associated with a first therapy program (PROGRAM E), two sleep stages (STAGE 2 and DEEP SLEEP) are grouped together and associated with a second therapy program (PROGRAM F), and another sleep stage (REM) is associated with a third therapy program (PROGRAM G). Upon detecting a biosignal that has a ratio of power levels within the beta and alpha bands that is greater than a first threshold value, THRESHOLD D, but less than a second threshold value, THRESHOLD E processor 50 may control stimulation generator 54 to deliver therapy to patient 12 according to the parameter values defined by PROGRAM E. By selecting PROGRAM E based on the comparison of the ratio of power levels to the first and second threshold values, processor 50 may determine patient 12 is in a sleep stage group including at least one of the AWAKE state or the STAGE 1 sleep stage.

If sleep stage detection module 59 determines that a biosignal has a ratio of power levels within the beta and alpha bands that is less than the first threshold, THRESHOLD D, such that the ratio is less than the threshold value associated with the AWAKE state and STAGE 1 sleep stage, processor 50 may control stimulation generator 54 to generate and deliver therapy to patient 12 according to the parameter values defined by PROGRAM F. By selecting PROGRAM F based on the comparison of the ratio of power levels within the selected frequency bands of the biosignal to the first threshold value, THRESHOLD D, processor 50 may determine patient 12 is in at least one of the STAGE 2 or DEEP SLEEP stages of a sleep state.

If sleep stage detection module 59 determines that a biosignal has a ratio of power levels within the beta and alpha bands that is greater than the second threshold, THRESHOLD E, such that the ratio is greater than the threshold value associated with the AWAKE state and STAGE 1 sleep stage, processor 50 may control stimulation generator 54 to deliver therapy to patient 12 according to the parameter values defined by PROGRAM G. By selecting PROGRAM G based on the comparison of the ratio of power levels within the selected frequency bands of the biosignal to the second threshold value, THRESHOLD E, processor 50 may determine patient 12 is within the REM sleep stage of a sleep state.

When sleep stage detection module 59 references the table shown in FIG. 15B to determine a patient sleep stage, processor 50 may control stimulation generator 54 to deliver therapy to patient 12 according to the same therapy program, regardless of whether patient 12 is an awake state or in the Stage 1. As FIG. 15B indicates, the presence of a relative high ratio of a beta band power to an alpha band power, as indicated by a value greater than THRESHOLD E, may be a marker for a transition from Stage 2 sleep to REM sleep. Further, sleep stage detection module 59 may use two threshold values, THRESHOLD D and THRESHOLD E, to distinguish between the awake state and Stage 1 sleep stage, and the REM stage. This may be useful if different therapy parameter values provide efficacious therapy to improve the quality of the patient's sleep during the Stage 1 stage versus the REM stage, or during the awake stage versus the REM stage.

FIG. 15C illustrates another example table, which sleep stage detection module 59 may reference in order to compare a ratio of power between a theta band and an alpha band of a biosignal of patient 12 to a common threshold value (THRESHOLD F in FIG. 15C) in order to select a therapy program for controlling therapy delivery to patient 12 by IMD 16. In some examples, the alpha band may be in a range of about 8 Hz to about 14 Hz, although other frequency ranges are contemplated for the alpha band. In some examples, the theta band may be in a range of about 4 Hz to about 8 Hz, while in other examples, the theta band may be in a range of about 5 Hz to about 10 Hz. Other frequency ranges are contemplated for the theta band. In addition, the ratio of power between a theta band and an alpha band of the biosignal may include a ratio of power between a subset of the theta band and a subset of the alpha band.

As FIG. 15C illustrates, the ratio of power between the theta band and alpha band may be useful for distinguishing between a first sleep stage group (GROUP A), which includes the awake state of patient 12 and the Stage 1 and REM sleep stages, and a second sleep stage group (GROUP B), which includes the Stage 2 and Deep Sleep stages of patient 12. Based on the data shown in the table of FIG. 15C, a patient awake state, the STAGE 1 sleep stage, and the REM sleep stage are grouped together and associated with a first therapy program (PROGRAM H), and two sleep stages (STAGE 2 and DEEP SLEEP) are grouped together and associated with a second therapy program (PROGRAM I). Upon detecting a biosignal that has a ratio of power levels within the theta and alpha bands that is less than a threshold value, THRESHOLD F, processor 50 may control stimulation generator 54 to generate and deliver electrical stimulation to patient 12 according to the parameter values defined by PROGRAM H. By selecting PROGRAM H based on the comparison of the ratio of power levels of the biosignal within the selected frequency bands to the threshold value, THRESHOLD F, processor 50 may determine patient 12 is in at least one of the AWAKE state or the STAGE 1 or REM sleep stages.

If processor 50 determines that a biosignal has a ratio of power levels within the theta and alpha bands that is greater than the threshold value, THRESHOLD F, processor 50 may control stimulation generator 54 to generate and deliver electrical stimulation to patient 12 according to the parameter values defined by PROGRAM I. By selecting PROGRAM I based on the comparison of the ratio of power levels of the biosignal within the selected frequency bands to the first threshold value, THRESHOLD F, processor 50 may determine patient 12 is in at least one of the STAGE 2 or DEEP SLEEP stages of a sleep state.

When processor 50 references the table shown in FIG. 15C to determine a patient sleep stage, processor 50 may deliver therapy to patient 12 according to the same therapy program, regardless of whether patient 12 is an awake state or in the Stage 1 or REM sleep stages. As FIG. 15C indicates, the presence of a relative low ratio of a theta band power to an alpha band power, as indicated by a value less than THRESHOLD F, may be a marker for a transition from the Stage 2 sleep stage to the REM sleep stage.

Figure 16:
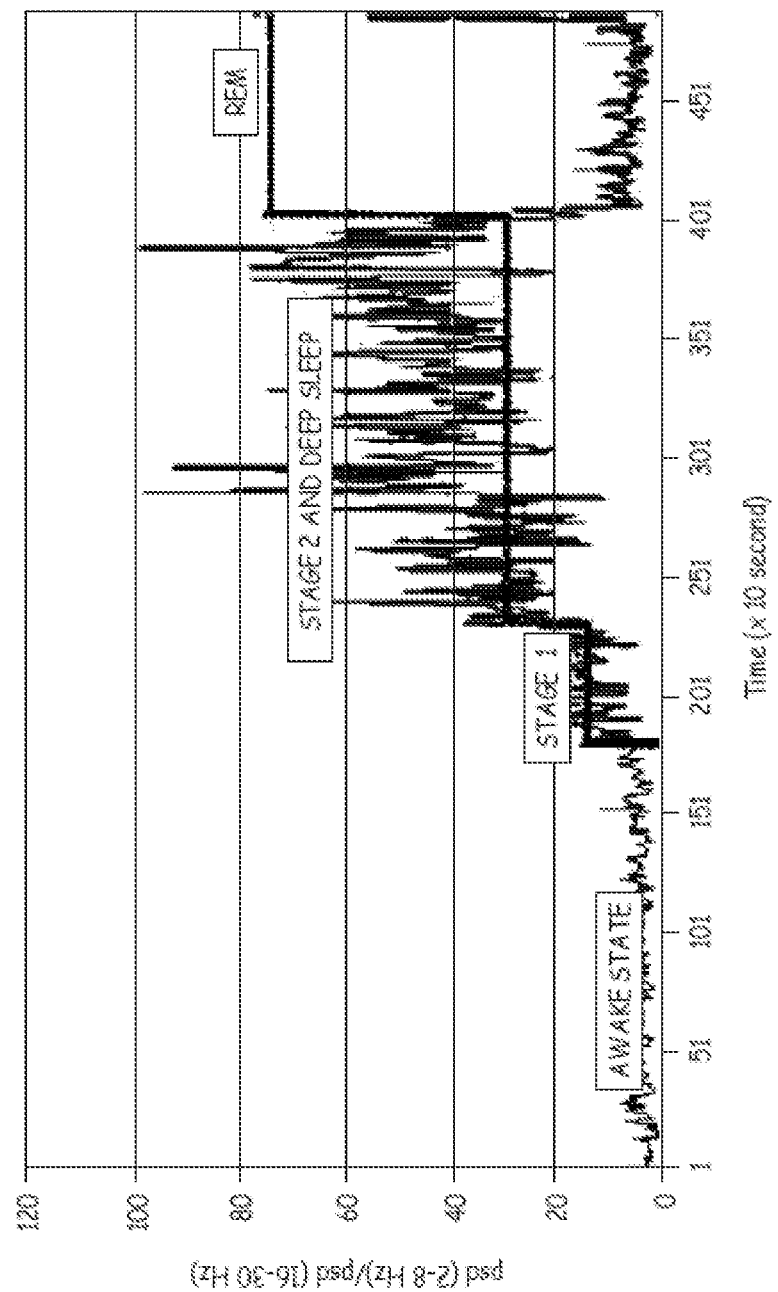
FIG. 16 is a conceptual graph illustrating a change in a ratio of powers of two frequency bands of a biosignal over time.

FIG. 16 is a graph illustrating a change in a ratio of power levels in a relatively low frequency band (e.g., a theta or alpha band) and a higher frequency band (e.g., a beta band) of a biosignal measured within a brain of a human subject over time. In the example shown in FIG. 16, the ratio is between the power level in a frequency band in a range of about 2 Hz to about 8 Hz and the power level in a frequency band in a range of about 16 Hz to about 30 Hz. The biosignal used to generate the data shown in the graph of FIG. 16 may be a local field potential measured in the subthalamic nucleus of a human subject diagnosed with Parkinson's disease.

As FIG. 16 illustrates, the ratio of energies within the relatively low frequency band and a higher frequency band is relatively low during both the awake state of patient 12 and the Stage 1 and REM sleep stages. The ratio increases during the Stage 2 and Deep Sleep stages of the sleep state. The graph shown in FIG. 16 suggests that the ratio of power levels in the frequency band in a range of about 2 Hz to about 8 Hz and the power level in a frequency band in a range of about 16 Hz to about 30 Hz may be useful for distinguishing between the awake state of patient and the Stage 2 and Deep Sleep stages, as well as distinguishing between the Stage 1 and REM sleep stages of the sleep state and the Stage 2 and Deep Sleep stages. A threshold value for determining whether patient 12 is generally in a first group of states, including the awake state and the Stage 1 and REM sleep stages, may be selected based on data similar to that shown in FIG. 16. For example, based on the graph shown in FIG. 16, the threshold value for comparing the ratio of power levels against may be about 30.

In examples in which processor 50 controls the delivery of therapy to patient 12 according to different therapy programs during the Stage 2 and Deep Sleep stages compared to the awake state and the Stage 1 and REM sleep stages, the threshold value may be selected based on a half power point of the value of the ratio of the relatively low frequency band (e.g., a theta or alpha band) and a higher frequency band (e.g., a beta band) of a biosignal. In FIG. 16, the maximum power level appears to occur during the Stage 2 and Deep Sleep stages. The biosignal in the graph of FIG. 16 decreases to the half power point or lower during the awake state and the Stage 1 and REM sleep stages. Thus, the half power point may be a relatively good indicator for when patient 12 switches from the Stage 1 sleep stage to the Stage 2 sleep stage, and from the Deep Sleep stage to the REM sleep stage.

Figure 17:
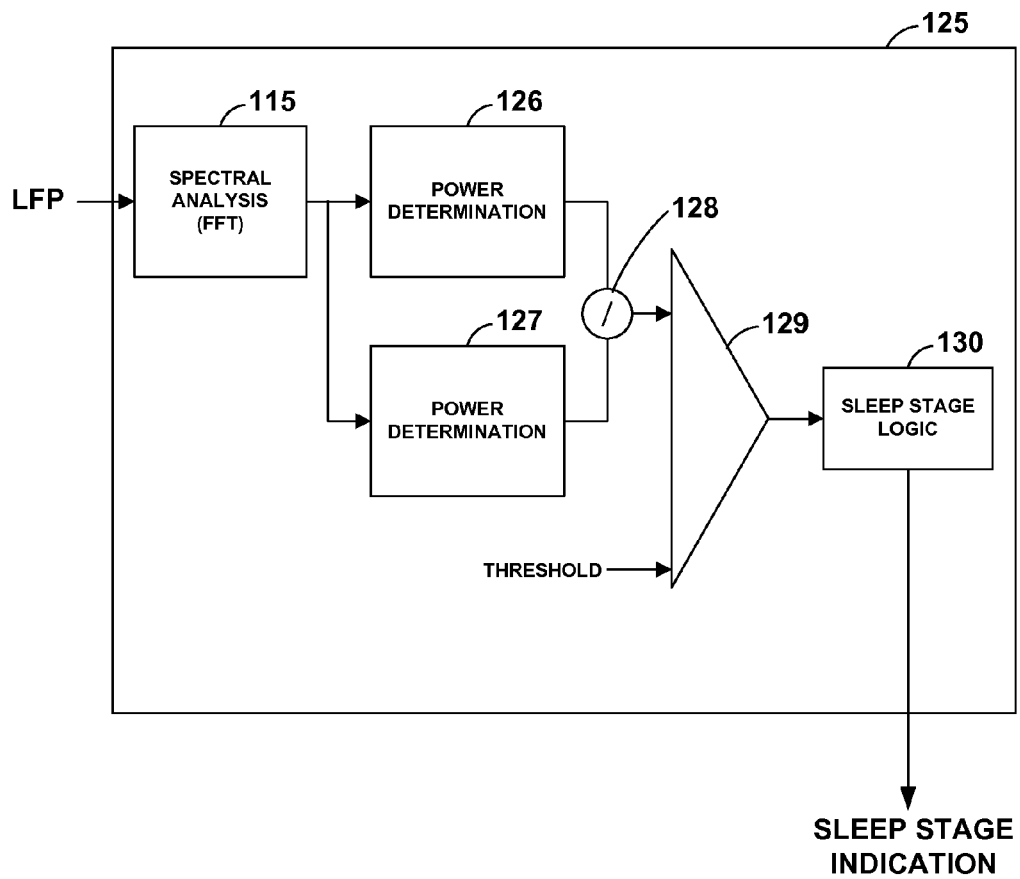
FIG. 17 is a logic diagram illustrating an example circuit that may be implemented to determine a sleep stage from a ratio of power levels within two frequency bands of a biosignal that is generated based on local field potentials (LFP) within a brain of a patient.

FIG. 17 is a logic diagram illustrating an example circuit module that determines a sleep stage of patient 12 from a biosignal that is generated based on local field potentials (LFP) within brain 13 of patient 12. Module 125 may be integrated into sleep stage detection module 59 of IMD 16 (FIG. 2) or of another device, such as programmer 14. A local field potential sensed by electrodes 22 of leads 20 or another set of electrodes may be transmitted into module 125 and provided to spectral analysis submodule 115, which extracts the frequency components of the local field potential signal, such as by implementing a fast Fourier transform algorithm. Although not shown in FIG. 17, in some examples, the local field potential signal may be provided to an amplifier prior to being sent to spectral analysis submodule 115.

After passing through spectral analysis submodule 115, the local field potential signal may pass through a first power determination submodule 126, which may determine a power of the local field potential signal in a first frequency band, and a second power determination submodule 127, which may determine a power of the local field potential signal in a second frequency band. In other examples, a bandpass filter may be used to extract the desired frequency band components of the local field potential signal.

In some examples, the first frequency band may be a beta band (e.g., about 10 Hz to about 30 Hz) or a subset of the beta band, and the second frequency band may be an alpha band (e.g., about 8 Hz to about 12 Hz) or a subset of the alpha band. In another example, the first frequency band may be a sigma band (e.g., about 12 Hz to about 16 Hz) or a subset of the sigma band, and the second frequency band may be a high beta band (e.g., about 16 Hz to about 30 Hz) or a subset of the high beta band. In another example, the first frequency band may be a theta band (e.g., about 4 Hz to about 8 Hz) or a subset of the theta band, and the second frequency band may be an alpha band (e.g., about 8 Hz to about 12 Hz) or a subset of the alpha band. Other frequency band combinations for determining a ratio are contemplated.

The extracted power levels of the local field potential signal outputted by power determination submodules 126, 127 may be sent to a ratio calculator 128, which may determine a value of the ratio between a first power level determined by first power determination module 126 and a second power level determined by second power determination module 127. The value determined by ratio calculator 128 may be sent to comparator 129, along with a threshold value, which may be provided by processor 50. As indicated above, the threshold value may be specific to a particular sleep stage or a group of sleep stages. Comparator 129 may compare the threshold value and the ratio value determined by ratio calculator 128, e.g., to determine whether the threshold is greater than or equal to, or, in some cases, less than or equal to the threshold value.

The signal from comparator 129 may be indicative of a sleep stage or a group of sleep stages of patient 12. Sleep stage logic 130 may determine the patient sleep stage based on the signal from comparator 129 and generate a sleep stage indication indicating that patient 12 may be within the determine sleep stage. Processor 50 may then take an action associated with the sleep stage indication, such as by referencing a look-up table (e.g., table 60 in FIG. 4). The look-up table may specify actions such as selecting a therapy program, activating or deactivating therapy delivery to patient 12 or modifying a therapy program.

In some examples, sleep stage logic 130 may include duration logic that determines whether a power level of the biosignal within a selected frequency band or a ratio of power levels within two or more selected frequency bands is greater than (or, in some cases, less than, and, in some cases equal to) a stored threshold value for a predetermined amount of time. If sleep stage logic 130 determines that the power level or ratio of power levels is greater than or equal to the stored threshold value for the predetermined amount of time, sleep stage logic 130 may determine that patient 12 is in the sleep stage associated with the threshold value. In other examples, sleep stage logic 130 may include duration logic that determines whether a power level of the biosignal within a selected frequency band or a ratio of power levels within two or more selected frequency bands is less than or equal to a stored threshold value for a predetermined amount of time.

Figure 18:
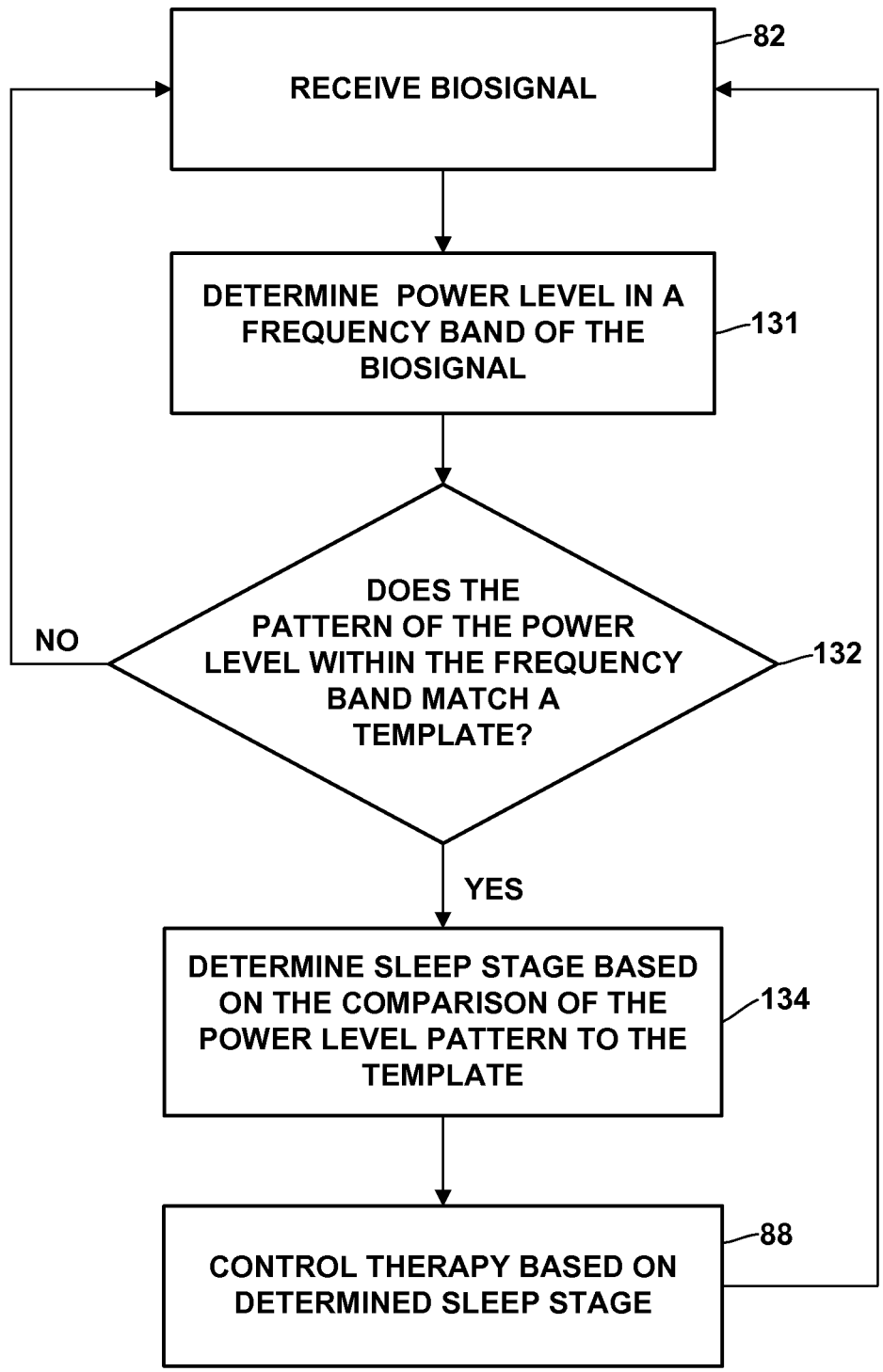
FIG. 18 is a flow diagram illustrating another example technique for controlling therapy delivery based on a determined patient sleep stage.

FIG. 18 is a flow diagram illustrating another example technique for controlling therapy delivery to patient 12 based on a determined sleep stage. Processor 50 may receive a biosignal that is sensed within brain 13 of patient 12 (82) and sleep stage detection module 59 may determine a power level within a selected frequency band of the biosignal (131). Sleep stage detection module 59 may determine a pattern in the power level within the selected frequency band over time and compare the pattern to a template. The template may be stored within memory 52 of IMD 16. Sleep stage detection module 59 may determine whether the pattern in the power level of the biosignal within the selected frequency band over time matches the template (132).

In some examples, sleep stage detection module 59 may sample a waveform with a sliding window, where the waveform may be defined by plotting the power level of the biosignal within the selected frequency over time with a sliding window and compare the waveform with stored template waveform. For example, sleep stage detection module 59 may perform a correlation analysis by moving a window along a digitized plot of the waveform of the biosignal at regular intervals, such as between about one millisecond to about ten millisecond intervals, to define a sample of the biosignal. The sample window may be slid along the plot until a correlation is detected between the template and the waveform defined by the power levels within the selected frequency band over time. By moving the window at regular time intervals, multiple sample periods may be defined.

The correlation may be detected by, for example, matching multiple points between the template waveform and the waveform of the plot of the power level within the selected frequency band of the biosignal over time, or by applying any suitable mathematical correlation algorithm between the sample in the sampling window and a corresponding set of samples stored in the template waveform. In some examples, the template matching algorithm that is employed to determine whether the pattern matches the template (132) may not require a one hundred percent (100%) correlation match, but rather may only match some percentage of the pattern. For example, if the pattern in the power level of the biosignal within the selected frequency band over time exhibits a pattern that matches about 75% or more of the template, the algorithm employed by sleep stage detection module 59 may determine that there is a substantial match between the pattern and the template.

If the pattern of the plot of the power level of the biosignal within the selected frequency band over time substantially matches a template (132), sleep stage detection module 59 may determine a sleep stage (134) of patient 12 and control therapy delivery to patient 12 based on the determined sleep stage (88). Sleep stage detection module 59 may determine the sleep stage (134) by referencing a data structure that may be stored within memory 52. For example, the data structure may associate the template with one or more sleep stages, and processor 50 may determine that patient 12 is in one or more of the sleep stages upon detecting a match between the pattern of power levels over time and the template.

If the pattern of the plot of the power level of the biosignal within the selected frequency band over time does not substantially match a pattern template (132), processor 50 may continue monitoring the biosignal (82) to detect the one or more sleep stages associated with the biosignal. In some cases, processor 50 may sequentially or substantially simultaneously compare the pattern of the plot of the power level of the biosignal within the selected frequency band over time to another template, which may be associated with another sleep stage or another group of sleep stages.

Figure 19:
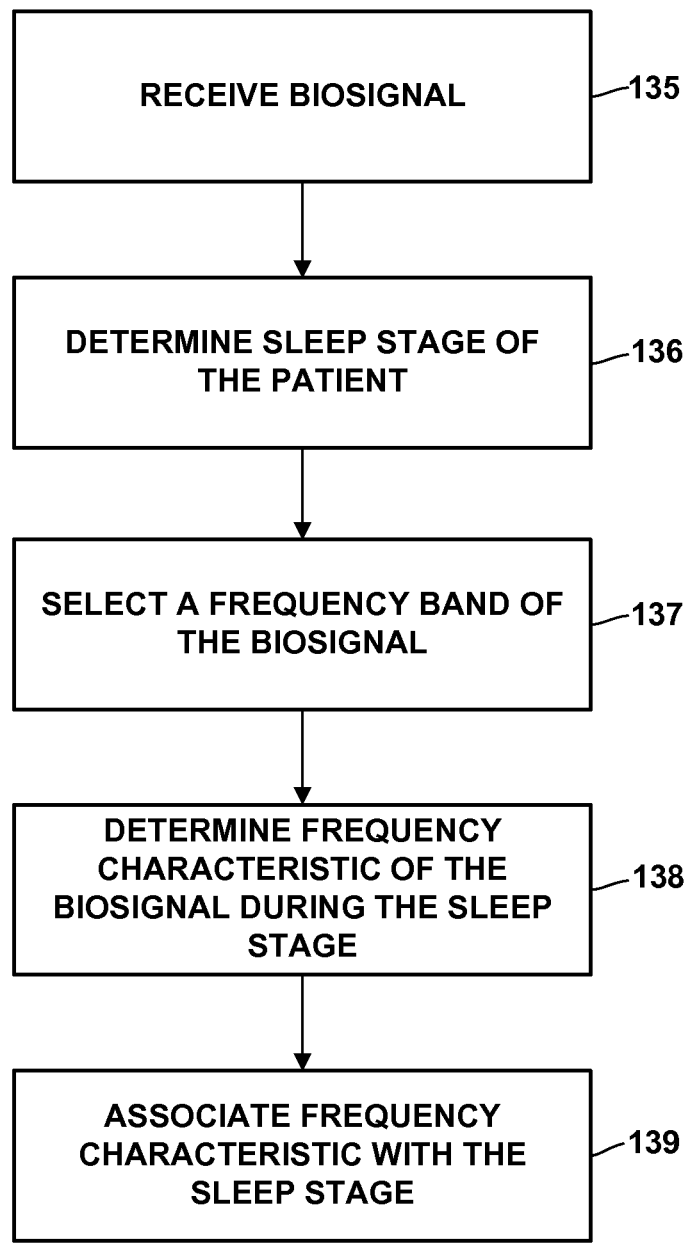
FIG. 19 is a flow diagram illustrating an example technique for associating one or more frequency characteristics of a biosignal with a patient sleep stage.

FIG. 19 is a flow diagram illustrating an example technique for associating one or more frequency characteristics of a biosignal with a sleep stage. The technique shown in FIG. 19 may be used to determine the threshold values or templates described above for determining one or more patient sleep stages based on a biosignal that is sensed within brain 13 of patient 12. Thus, in some examples, the technique shown in FIG. 19 may be performed during a programming session or a trial stage that occurs prior to implementation of the IMD 16 control technique based on a detected sleep stage (e.g., the techniques shown in FIGS. 6, 7, 14, and 18). In some examples, the one or more frequency characteristics of the biosignal that are associated with a sleep stage and are later used to determine a sleep stage of patient 12 may be specific to patient 12. For example, a sleep study may be conducted, during which the clinician may monitor a biosignal generated within brain 13 of patient 12 during the patient's sleep state and determine the one or more frequency characteristics while patient 12 is asleep. In other examples, the one or more frequency characteristics of the biosignal that are associated with a sleep stage and are later used to determine a sleep stage of patient 12 may be based on data from two or more patients, which may include, for example, patients having similar neurological disorders or at least similar sleep disorder symptoms. While FIG. 19 is primarily described with reference to processor 70 of programmer (FIG. 5), in other examples, another device (e.g., IMD 16 or another computing device), alone or in combination with programmer 14 may perform the technique shown in FIG. 19.

Processor 70 may receive a biosignal from IMD 16 or a different sensing module (135), where the biosignal indicates activity within brain 13 of patient 12. Processor 70 may determine a sleep stage of patient 12 (136). In one example, processor 70 may receive input from the clinician indicating the sleep stage of patient 12, or processor 70 may determine the sleep stage based on a physiological parameter of patient 12 other than a brain signal, as described below with reference to FIGS. 20 and 21.

Processor 70 may select one or more frequency bands of the biosignal (137) in order to determine a frequency characteristic of the sleep stage (138). If processor 70 determines a frequency characteristic that includes a ratio in two frequency bands, processor 70 may select two frequency bands of the biosignal (137). Depending on the patient or the sleep stage, the frequency bands that are useful for distinguishing between two or more different patient sleep stages or otherwise determining a patient sleep stage based on a biosignal from brain 13 may differ.

In some examples, processor 70 may select the one or more frequency bands based on input from the clinician. In other examples, processor 70 may reference information stored within memory 72 of programmer 14 to determine the one or more frequency bands to select. The information may suggest, for example, one or more frequency bands that may be useful for determining a frequency band characteristic for determining the determined sleep stage. The information may based on prior studies on patient 12 or a group of two or more patients that have similar sleep disorder or movement disorder symptoms as patient 12. The clinician or processor 70 may select a frequency band that is believed to distinguish the current sleep stage of patient (determined in block 136) from one or more other sleep stages.

Processor 70 may determine the frequency characteristic of the biosignal (138) using any suitable technique. In one example, the clinician may provide input via user interface 76 of programmer 14 that indicates the type of frequency characteristic processor 70 should extract from the biosignal. The clinician or processor 70 may automatically select a peak, median, average or lowest power level of the biosignal during the sleep stage or a portion of the sleep stage. The duration of the sleep stage may be determined based on clinician input or other physiological parameters that may indicate when patient 12 transitions to the next sleep stage following the currently detected sleep stage. The peak, median or average power level may then be stored as a threshold value for detecting the sleep stage.

As another example, the clinician or processor 70 may automatically select a peak, median, average or lowest value of the ratio of power levels of the biosignal in the selected frequency bands during the sleep stage or at least a portion of the sleep stage as the frequency characteristic. The peak, median, average or lowest value may then be stored as a threshold value for detecting the sleep stage. As another example, the clinician or processor 70 may automatically select a pattern of the power levels of the biosignal in the selected frequency band during the sleep stage or at least a portion of the sleep stage as the frequency characteristic. The pattern of the power levels of the biosignal over time or the amplitude waveform of the biosignal during the selected time period may be stored as a template for detecting the sleep stage. If the amplitude waveform of the biosignal is stored, processor 50 of IMD 16 may later analyze the frequency band components of the biosignal waveform to determine the pattern of power levels that indicate patient 12 is in the sleep stage.

After determining the frequency characteristic of the biosignal, processor 70 may associate the characteristic with the sleep stage in memory 72 of programmer 14 (139). In some examples, processor 70 may transmit the frequency characteristic and associated sleep stage information to IMD 16 via the respective telemetry modules 74, 56. In some examples, the clinician may review and modify the information prior to programming IMD 16 with the frequency characteristic information.

Figure 20:
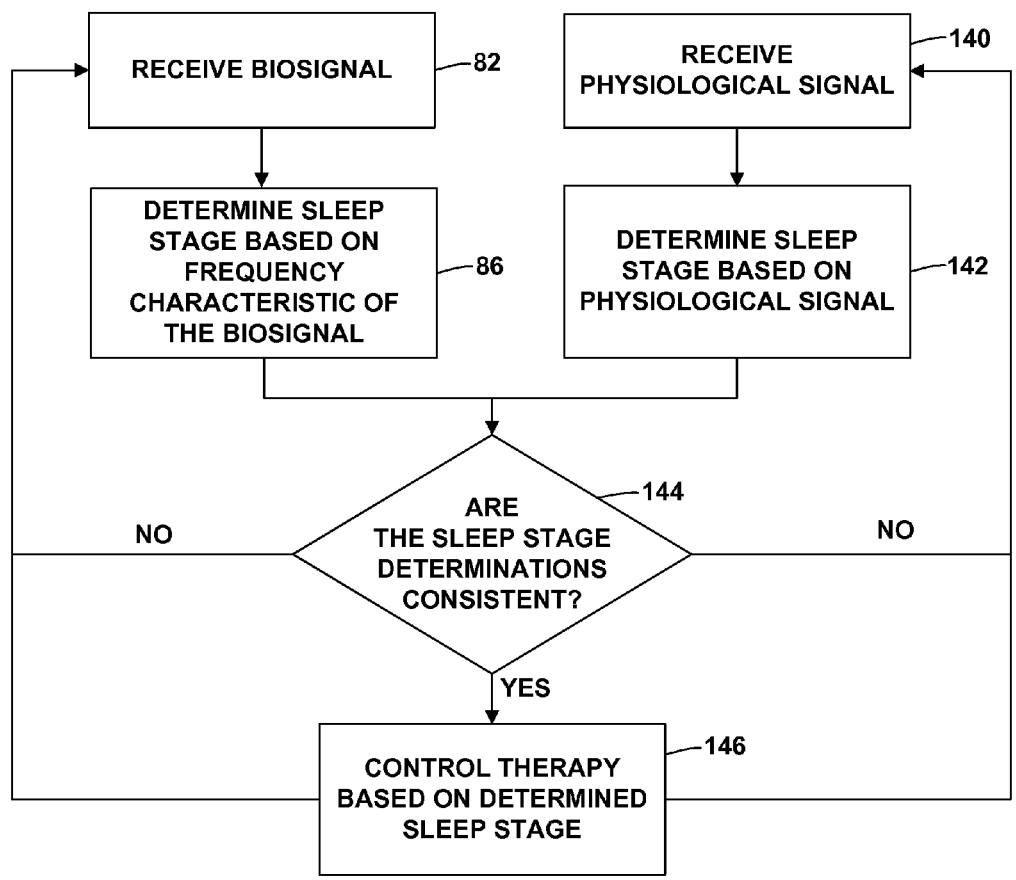
FIG. 20 is a flow diagram illustrating an example technique for controlling therapy delivery based on multiple sleep stage determinations.

FIG. 20 is a flow diagram illustrating an example technique for confirming that patient 12 is in a particular sleep stage based on at least two determinations of the sleep stage based on different variables. In some examples, as shown in FIG. 20, processor 50 may determine the sleep stage after determining that a sleep stage determination by sleep stage detection module 59 based on a frequency characteristic of a biosignal from within brain 13 of patient 12 substantially matches a sleep stage determination based on another physiological parameter of patient. Independently validating the patient sleep stage based on two different signals may help detect a potential failure mode of the sleep stage detection module 59 or sensing module 55.

Processor 50 may receive a biosignal (82) and determine a sleep stage based on a frequency characteristic of the biosignal, e.g., using the techniques described with respect to FIGS. 6, 7, 14, and 18. As previously described, in other examples, sleep stage detection module 59 may determine the frequency characteristic of the biosignal and/or the sleep stage determination.

Processor 50 may also receive a physiological signal (140). The physiological signal may change as a function of a physiological parameter of patient 12 that is indicative of a sleep stage, such as an activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response. Processor 50 may determine a sleep stage based on the physiological signal (142). Processor 50 may detect a sleep stage of patient 12 based on the physiological signal using any suitable technique. As various examples, processor 50 may compare a voltage or current amplitude of the physiological signal with a threshold value, correlate an amplitude waveform of the physiological signal in the time domain or frequency domain with a template signal, or combinations thereof. The threshold values or templates may be determined based on sleep studies performed on patient 12 or one or more patients, which case the thresholds and templates may not be specific to patient 12.

In one example, the instantaneous or average amplitude of the physiological signal over a period of time may be compared to an amplitude threshold, which may be associated with one or more sleep stages. As another example, a slope of the amplitude of the physiological signal over time or timing between inflection points or other critical points in the pattern of the amplitude of the physiological signal over time may be compared to trend information. Different trends may be associated with one or more sleep stages. A correlation between the inflection points in the amplitude waveform of the physiological signal or other critical points and a template may indicate the occurrence of the sleep stage associated with the template.

As another example, processor 50 may perform temporal correlation with templates by sampling the waveform generated by the physiological signal with a sliding window and comparing the waveform with stored template waveforms that are indicative of the one or more different sleep stages. If more than one sleep stage may be detected with different templates, processor 50 may compare the physiological signal waveform with the template waveforms for the plurality of sleep stages in any desired order or substantially simultaneously. For example, processor 50 may compare the physiological signal with the template waveform indicative of a first sleep stage, followed by the template waveform indicative of a second sleep stage, and so forth.

In one example, processor 50 may perform a correlation analysis by moving a window along a digitized plot of the amplitude waveform of physiological signal at regular intervals, such as between about one millisecond to about ten millisecond intervals, to define a sample of the physiological signal. The sample window may be slid along the plot until a correlation is detected between a waveform of a template stored within memory 52 and the waveform of the sample of the physiological signal defined by the window. By moving the window at regular time intervals, multiple sample periods may be defined. The correlation may be detected by, for example, matching multiple points between a template waveform and the waveform of the plot of the physiological signal over time, or by applying any suitable mathematical correlation algorithm between the sample in the sampling window and a corresponding set of samples stored in the template waveform.

After making separate and independent determinations of the sleep stage based on the physiological signal (142) and the frequency characteristic of the biosignal (86), processor 50 may determine whether the sleep stage determinations are consistent (144). The sleep stage determinations may be consistent if both sleep stage determinations indicate patient 12 is in the same sleep stage or the same group of sleep stages. For example, if processor 50 determines that the frequency characteristic of the biosignal indicates patient 12 is in a first sleep stage, and the physiological signal indicates patient 12 is in a second sleep stage, but the first and second sleep stages are associated with a common sleep stage group (e.g., which is associated with the same therapy program), processor 50 may determine that the sleep stage determinations are consistent.

If the sleep stage determinations are consistent (144), processor 50 may control therapy delivery based on the determined sleep stage (146). If the sleep stage determinations are not consistent (144), processor 50 may determine that the sleep stage module 59 or the sensing module providing the physiological signal failed, and one of the sleep stage determinations was incorrect. Processor 50 may not control therapy delivery to patient 12 in response to detecting the sleep stage. Accordingly, if IMD 16 is delivering therapy to patient 12 according to a therapy program, IMD 16 may continue delivering therapy to patient 12 according to the therapy program. As another example, if IMD 16 is not delivering therapy to patient 12, IMD 16 may remain in a deactivated state. Processor 50 may then continue monitoring the biological signal (82) and physiological signal (140) until sleep stage determinations based on a respective one of the physiological signal and biological signal match.

Figure 21:
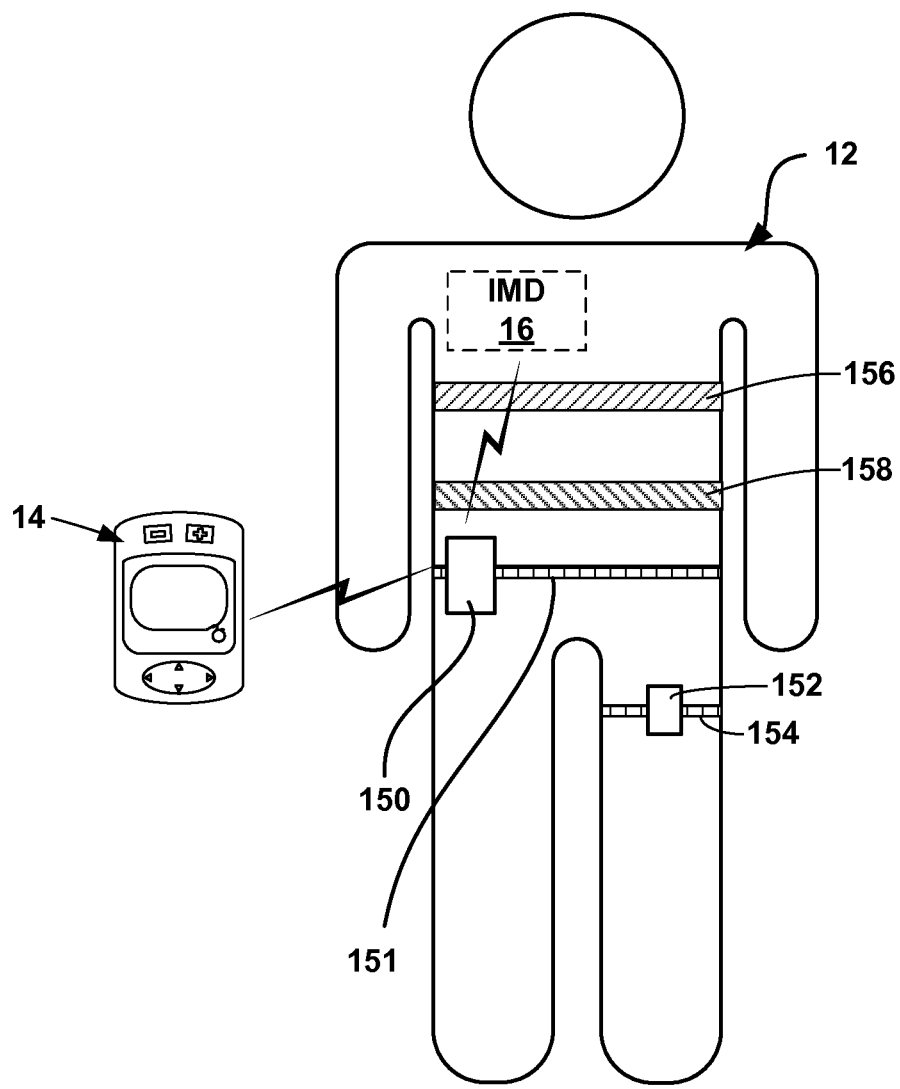
FIG. 21 is a conceptual illustration of examples of different sensing modules that may be used to generate physiological signals indicative of one or more physiological parameters of a patient.

As previously indicated, in some examples, processor 50 of IMD 16 or a processor of another device may determine whether patient 12 is in a sleep state prior to determining the particular sleep stage of the sleep state patient is in. The sleep state, and, in some examples, the sleep stage of patient 12 may be determined based on a physiological parameter of patient 12 other than biosignals within brain 13. FIG. 21 is a conceptual illustration of examples of different sensing modules that may be used to generate physiological signals indicative of one or more physiological parameters of patient 12. The sensing modules shown in FIG. 21 may be used instead of or in addition to sensors that are coupled to IMD 16 or implanted within patient 12 separate from IMD 16. One example of a sensing module is motion sensor 150, which includes sensors that generate a signal indicative of patient motion, such as 2-axis or 3-axis accelerometer or a piezoelectric crystal. Motion sensor 150 is coupled to a torso of patient 12 via a belt 151 and may transmit signals to IMD 16, programmer 14 or another device.

Detection of patient movement via signals generated by motion sensor 150 may be used to determine whether patient 12 is in a sleep state, e.g., by detecting a relatively high level of motion, which may indicate patient is in an awake state or detecting a relatively low level of motion, which may indicate patient 12 is in a sleep state. As examples, threshold comparisons, peak level detection or threshold crossings may be used to determine whether patient 12 is in an awake state or sleep state stated based on signals from motion sensor 110.

Processor 50 of IMD 16 may monitor output from motion sensor 150. Signals generated by motion sensor 150 may be sent to processor 50 of IMD 16 (FIG. 3) via wireless signals. Processor 50 or another processor may determine a patient's posture or activity level using any suitable technique, such as by output from motion sensor 150 or another sensing that generates a signal indicative of heart rate, respiration rate, respiratory volume, core temperature, blood pressure, blood oxygen saturation, partial pressure of oxygen within blood, partial pressure of oxygen within cerebrospinal fluid, muscular activity, arterial blood flow, EMG, an EEG, an ECG or galvanic skin response. Processor 50 may associate the signal generated by a 3-axis accelerometer or multiple single-axis accelerometers (or a combination of a three-axis and single-axis accelerometers) with a patient posture, such as sitting, recumbent, upright, and so forth, and may associate physiological parameter values with patient activity level. For example, processor 50 may process the output from accelerometers located at a hip joint, thigh or knee joint flexure coupled with a vertical orientation sensor (e.g., an accelerometer) located on the patient's torso or head in order to determine the patient's posture. The determined posture level may also indicate whether patient 12 is in a sleep state or an awake state. For example, when patient 12 is determined to be in a recumbent posture, processor 50 may determine patient 12 is sleeping. As another example, if processor 50 determines patient 12 is standing or sitting up, processor 50 may determine patient 12 is in an awake state.

Suitable techniques for determining a patient's activity level or posture are described in commonly-assigned U.S. Pat. No. 7,395,113 to Heruth et al., entitled, "COLLECTING ACTIVITY INFORMATION TO EVALUATE THERAPY," and U.S. Pat. No. 7,769,464 to Gerber et al., entitled, "THERAPY ADJUSTMENT." U.S. Pat. No. 7,395,113 and U.S. Pat. No. 7,769,464 are incorporated herein by reference in their entireties. As described in U.S. Pat. No. 7,395,113, a processor may determine an activity level based on a signal from a sensor, such as an accelerometer, a bonded piezoelectric crystal, a mercury switch or a gyro, by sampling the signal and determining a number of activity counts during the sample period. For example, processor 50 may compare the sample of a signal generated by an accelerometer or piezoelectric crystal to one or more amplitude thresholds stored within memory 52. Processor 50 may identify each threshold crossing as an activity count. Where processor 50 compares the sample to multiple thresholds with varying amplitudes, processor 50 may identify crossing of higher amplitude thresholds as multiple activity counts.

A motion sensor may be coupled to patient 12 at any suitable location and via any suitable technique, and more than two motion sensors may be used to determine a patient awake or sleep state, and, in some cases, a patient sleep stage within the sleep state. For example, as shown in FIG. 21, accelerometer 152 may be coupled to a leg of patient 12 via band 154. Alternatively, a motion sensor may be attached to patient 12 by any other suitable technique, such as via a wristband. In other examples, a motion sensor may be incorporated into IMD 16.

In some examples, a sensing module that senses a physiological parameter of patient 12 other than a biosignal within brain 13 may include ECG electrodes, which may be carried by an ECG belt 156. ECG belt 156 incorporates a plurality of electrodes for sensing the electrical activity of the heart of patient 12. In the example shown in FIG. 21, ECG belt 156 is worn by patient 12. Processor 50 may monitor the patient's heart rate and, in some examples, ECG morphology based on the signal provided by ECG belt 156. Examples of suitable ECG belts for sensing the heart rate of patient 12 are the "M" and "F" heart rate monitor models commercially available from Polar Electro OY of Kempele, Finland. In some examples, instead of ECG belt 156, patient 12 may wear a plurality of ECG electrodes (not shown in FIG. 21) attached, e.g., via adhesive patches, at various locations on the chest of patient 12, as is known in the art. An ECG signal derived from the signals sensed by such an array of electrodes may enable both heart rate and ECG morphology monitoring, as is known in the art. In addition to or instead of ECG belt 156, IMD 16 may sense the patient's heart rate, e.g., using electrodes on a housing of IMD 16, electrodes 22 of leads 20, electrodes coupled to other leads or any combination thereof.

In other examples, a therapy system (e.g., DBS system 10 of FIG. 1) may include a respiration belt 158 that outputs a signal that varies as a function of respiration of the patient may also be worn by patient 12 to monitor activity to determine whether patient 12 is in a sleep state, and, in some cases, to determine a sleep stage of patient 12. For example, in an REM sleep stage, the patient's respiration rate may increase relative to a baseline respiration rate associated with Stage 2 or Deep Sleep stages of patient 12. Respiration belt 158 may be a plethysmography belt, and the signal output by respiration belt 158 may vary as a function of the changes is the thoracic or abdominal circumference of patient 12 that accompany breathing by patient 12. An example of a suitable respiration belt is the TSD201 Respiratory Effort Transducer commercially available from Biopac Systems, Inc. of Goleta, Calif. Alternatively, respiration belt 158 may incorporate or be replaced by a plurality of electrodes that direct an electrical signal through the thorax of patient 12, and circuitry to sense the impedance of the thorax, which varies as a function of respiration of patient 12, based on the signal. The respiration belt may, for example, be used to generate an impedance cardiograph (ICG), which detects properties of blood flow in the thorax. In some examples, the ECG and respiration belts 156, 158, respectively, may be a common belt worn by patient 12.

In some examples, a therapy system may also include one or more electrodes (not shown in FIG. 21), which may be a surface electrode or intramuscular electrode, that are positioned to monitor muscle activity (e.g., EMG) of patient 12. Processor 50 may determine muscle activity within a limb of patient 12, such as an arm or leg. Movement of muscles within the patient's limb may be indicative of whether patient 12 is in a movement state (relatively high muscle activity) or sleep state (relatively little muscle activity for an extended period of time). Each of the types of sensing modules 150, 152, 156, 158 or EMG electrodes described above may be used alone or in combination with each other, as well as in addition to other sensing devices. Furthermore, in some examples, the sensing modules may transmit signals to IMD 16, programmer 14 or another device, and a processor within the receiving device may determine whether patient 12 is awake or asleep, and, in some examples, may determine a sleep stage of the sleep state of patient 12.

While DBS system 10 that delivers electrical stimulation to brain 13 patient 12 is primarily referred to in the disclosure, in other examples, IMD 16 may deliver electrical stimulation to other tissue sites within patient 12, such as to provide functional electrical stimulation of specific muscles or muscle groups. In addition, in other examples, a therapy system that delivers a therapeutic agent to patient 12 may also control therapy delivery based on a detection of whether patient 12 is in an awake state or a sleep state, or based on a detection of a sleep stage of the sleep state. A medical device may deliver one or more therapeutic agents to tissue sites within brain 13 of patient 12 or to other tissue sites within patient.

Figure 22:
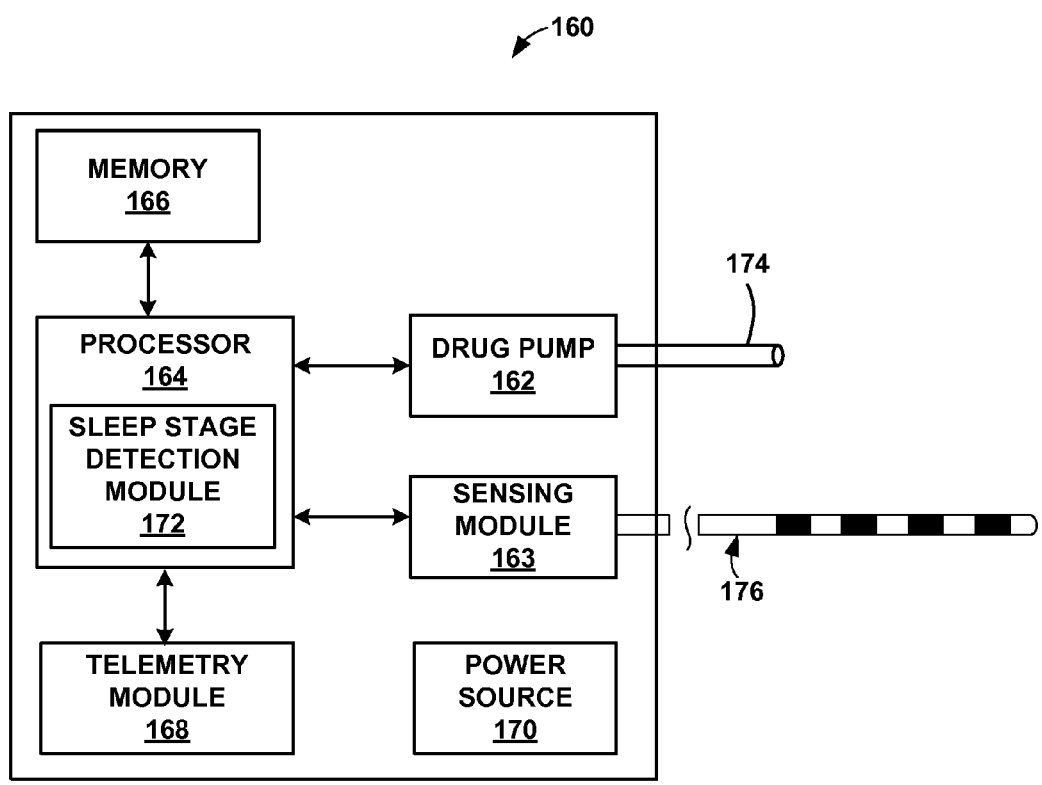
FIG. 22 is functional block diagram illustrating components of an example medical device that delivers a therapeutic agent to a patient.

FIG. 22 is functional block diagram illustrating components of an example medical device 160 with a drug pump 162. Medical device 160 may be used a therapy system in which therapy delivery is controlled based on a determined sleep stage of patient 12. Medical device 160 may be implanted or carried externally to patient 12. As shown in FIG. 22, medical device 160 includes drug pump 162, sensing module 163, processor 164, memory 166, telemetry module 168, power source 170, and sleep stage detection module 172. Processor 164, memory 166, telemetry module 168, power source 170, sensing module 163, and sleep stage detection module 172 may be substantially similar to processor 50, memory 52, telemetry module 56, power source 58, sensing module 55, and sleep stage detection module 59, respectively, of IMD 16 (FIG. 2).

Processor 164 controls drug pump 162 to deliver a specific quantity of a pharmaceutical agent to a desired tissue within patient 12 via catheter 174 that is at least partially implanted within patient 12. In some examples, medical device 160 may include stimulation generator for producing electrical stimulation in addition to delivering drug therapy. Processor 164 may control the operation of medical device 160 with the aid of instructions that are stored in memory 166.

Medical device 160 is configured to deliver a drug (i.e., a pharmaceutical agent) or another fluid to tissue sites within patient 12. Just as with sleep stage detection module 59 of IMD 16, sleep stage detection module 172 (alone or with processor 164) may be configured to determine a sleep stage of patient 12 based on a frequency characteristic of a biosignal generated within brain 13. Sensing module 163 may monitor a biosignal from within brain 13 of patient 12 via electrodes of lead 176. Sleep stage detection module 172 may determine the determined sleep stage based on a biosignal from sensing module 163, and processor 164 may control drug pump 162 to deliver therapy associated with the determined patient stage. For example, processor 164 may select a therapy program from memory 52 based on the determined sleep stage, such as by selecting a stored program or modifying a stored program, where the program includes different fluid delivery parameter values, and control drug pump 162 to deliver a pharmaceutical agent or another fluid to patient 12 in accordance with the selected therapy program. The fluid delivery parameter values may include, for example, a dose (e.g., a bolus or a group of boluses) size, a frequency of bolus delivery, a concentration of a therapeutic agent in the bolus, a type of therapeutic agent to be delivered to the patient (if the medical device is configured to deliver more than one type of agent), a lock-out interval, and so forth.

In the example shown in FIG. 22, sleep stage detection module 172 is a part of processor 164. In other examples, sleep stage detection module 172 and processor 164 may be separate components, and, in some cases, the separate sleep stage detection module 172 may include a separate processor. In addition, sensing module 163 may be in a separate housing from IMD 160.

In other examples of IMD 16 (FIG. 2) and medical device 160 (FIG. 22), the respective sleep stage detection module 59, 172 may be disposed in a separate housing from IMD 16, medical device 160, respectively. In such examples, the sleep stage detection module may communicate wirelessly with IMD 16 or medical device 160, thereby eliminating the need for a lead or other elongated member that couples the sleep stage detection module to IMD 16 or medical device 160.

The frequency ranges for the frequency bands described herein, such as the theta, alpha, beta, and sigma bands, are merely examples. In other examples, frequency bands may be defined by other frequency ranges.

In general, different therapy systems may require different algorithms for controlling therapy delivery to patient 12 based on a determined sleep stage. For example, processor 50 or another controller may automatically turn off therapy delivery to patient during all sleep stages if a patient has essential tremor. In other examples, such as with a patient with Parkinson's disease, processor 50 or another controller may automatically activate therapy when the patient is awake or in one of the Stage 1 or REM sleep stages, and deactivate therapy or decrease the intensity when the patient is in the Stage 2 or Deep Sleep stages. Other control algorithms are contemplated and may be specific to the patient or patient condition. In addition, other sleep stages and sleep stage groups are contemplated and may be selected based on the patient, patient condition or other factors.

An example of a logic diagram that may be used to detect the sleep stage of a patient based on an EEG signal (one example of a biosignal) is described at FIG. 4 in commonly-assigned U.S. Patent Application Serial No. 2007/0123758 to Miesel et al., entitled, "DETERMINATION OF SLEEP QUALITY FOR NEUROLOGICAL DISORDERS," which was filed on Oct. 31, 2006, and is incorporated herein by reference in its entirety.

In some examples, the devices, systems, and methods for determining whether patient 12 is in an awake state or a sleep state, and determining a sleep stage of a patient may be useful in the therapy systems described in commonly-assigned U.S. Pat. No. 8,290,596 to Wei et al, entitled, "THERAPY PROGRAM SELECTION," which was filed on Sep. 25, 2008, issued on Oct. 16, 2012, and is incorporated herein by reference in its entirety, and U.S. Provisional Patent Application No. 61/023,522 by Stone et al., entitled, "THERAPY PROGRAM SELECTION," which was filed on Jan. 25, 2008 and is incorporated herein by reference in its entirety.

In some examples described by U.S. Pat. No. 8,290,596 to Wei et al and U.S. Provisional Patent Application No. 61/023,522 by Stone et al., therapy program for a patient may be selected based on whether the patient is in a movement, sleep or speech state. Many patient conditions, such as Parkinson's disease or other neurological disorders, include impaired movement, sleep, and speech states, or combinations of impairment at least two of the movement, sleep, and speech states. Different therapy parameter values may provide efficacious therapy for the patient's movement, sleep and speech states. A movement state may include a state in which the patient is intending on moving, is attempting to initiate movement or has initiated movement. A speech state may include a state in which the patient is intending on speaking, is attempting to speak or has initiated speech. A sleep state may include a state in which the patient is intending on sleeping, is attempting to sleep or has initiated sleep. The techniques described herein may be useful for controlling the therapy delivery during the sleep state, e.g., based on a sleep stage of the patient during the sleep state.

Various embodiments of the described invention may be implemented using one or more processors that are realized by one or more microprocessors, ASIC, FPGA, or other equivalent integrated or discrete logic circuitry, alone or in any combination. In some cases, the functions attributed to the one or more processors described herein may be embodied as software, firmware, hardware or any combination thereof. The processors may also utilize several different types of storage methods to hold computer-readable instructions for the device operation and data storage. These memory and storage media types may include a type of hard disk, RAM, ROM, EEPROM, or flash memory, e.g. CompactFlash, SmartMedia, or Secure Digital (SD). Each storage option may be chosen depending on the example.

The disclosure also contemplates computer-readable media comprising instructions to cause a processor to perform any of the functions described herein. The computer-readable media may take the form of any volatile, non-volatile, magnetic, optical, or electrical media, such as a RAM, ROM, NVRAM, EEPROM, flash memory, or any other digital media. A programmer, such as clinician programmer 22 or patient programmer 24, may also contain a more portable removable memory type to enable easy data transfer or offline data analysis.

Various examples have been described. These and other examples are within the scope of the following claims.

The invention claimed is:

1. A system comprising:
   a medical device configured to be implanted in a patient, the medical device comprising a therapy module configured to deliver therapy to a patient;

a sensing module;
external electrodes configured to be located external to the patient and electrically coupled to the sensing module, wherein the sensing module is configured to sense a brain signal of the patient via the external electrodes; and
a processor configured to receive the brain signal from the sensing module, detect a non-REM sleep stage of the patient based on the brain signal, and, in response to detecting the non-REM sleep stage, control the therapy module to deliver therapy configured to improve performance of one or more motor tasks by the patient relative to a patient state in which the patient is not receiving the therapy.

2. The system of claim 1, wherein the non-REM sleep stage comprises one or more of a Stage 1 sleep stage, a Stage 2 sleep stage, or a Deep Sleep sleep stage.

3. The system of claim 1, wherein the processor is configured to detect the non-REM sleep stage by at least:
determining a frequency characteristic of the brain signal, and
determining a sleep stage of the patient based on the determined frequency characteristic of the brain signal.

4. The system of claim 3, wherein the frequency characteristic comprises at least one of: a power level of the brain signal within one or more frequency bands, a ratio of power levels in two or more frequency bands of the brain signal, or a trend in a power level of the brain signal within one or more frequency bands over time.

5. The system of claim 3, wherein the sensing module comprises a first sensing module, the system further comprising a second sensing module configured to generate a physiological signal indicative of a physiological parameter of the patient, wherein the physiological signal is different than the brain signal, wherein the processor is configured to determine a first sleep stage based on the frequency characteristic of the brain signal, receive the physiological signal from the second sensing module, determine a second sleep stage based on the physiological signal, and determine the sleep stage of the patient based on the first and second sleep stage determinations.

6. The system of claim 1, wherein the sensing module is separate from the medical device.

7. The system of claim 1, wherein the therapy comprises electrical stimulation therapy.

8. The system of claim 7, wherein the electrical stimulation therapy comprises deep brain electrical stimulation therapy.

9. The system of claim 1, wherein the therapy comprises delivery of a therapeutic agent.

10. The system of claim 1, wherein the processor is configured to determine the patient is in at least one of an awake state, a first sleep stage or a second sleep stage based on a frequency characteristic of the brain signal, and control the therapy module to activate therapy delivery to the patient in response to determining the patient is in the awake state or the first sleep stage and control the therapy module to deactivate or decrease an intensity of therapy delivered to the patient in response to determining the patient is in the second sleep stage.

11. The system of claim 10, wherein the first sleep stage comprises at least one of a Stage 1 or rapid eye movement sleep stage and the second sleep stage comprises at least one of a Deep Sleep or Stage 2 sleep stage.

12. The system of claim 1, wherein the processor is further configured to detect a REM sleep stage of the patient based on the brain signal and control the therapy module to, in response to detecting the REM sleep stage, to deliver therapy that minimizes movement of the patient relative to the patient state in which the patient is not receiving the therapy.

13. The system of claim 1, wherein the processor is configured to determine whether the patient is in a sleep state.

14. The system of claim 13, wherein the sensing module comprises a first sensing module, the system further comprising a second sensing module configured to generate a physiological signal indicative of a physiological parameter of the patient, wherein the physiological parameter comprises at least one of an activity level, posture, heart rate, electrocardiogram morphology, or core temperature, wherein the processor is configured to receive the physiological signal and determine whether the patient is in the sleep state based on the physiological signal.

15. The system of claim 1, wherein the brain signal comprises an electrocorticogram (ECoG) signal.

16. The system of claim 1, wherein the brain signal comprises an electroencephalogram (EEG) signal.

17. The system of claim 1, wherein the processor is configured to control the therapy module to deliver therapy configured to improve performance of one or more motor tasks by the patient relative to a patient state in which the patient is not receiving the therapy by at least controlling the therapy module to deliver therapy configured to improve performance of one or more of initiating movement or maintaining movement by the patient relative to a patient state in which the patient is not receiving the therapy.

18. A method comprising:
receiving, by a processor, a brain signal of a patient sensed by a sensing module via external electrodes electrically coupled to the sensing module, wherein the external electrodes are located external to the patient;
detecting, by the processor, a non-REM sleep stage of the patient based on the brain signal; and
in response to detecting the non-REM sleep stage, controlling, by the processor, a therapy module of an implantable medical device to deliver therapy configured to improve performance of one or more motor tasks by the patient relative to a patient state in which the patient is not receiving the therapy.

19. The method of claim 18, wherein receiving the brain signal comprises receiving the brain signal sensed by the sensing module via the external electrodes placed on a scalp of the patient.

20. The method of claim 18, wherein the brain signal comprises an electrocorticogram (ECoG) signal.

21. The method of claim 18, wherein the brain signal comprises an electroencephalogram (EEG) signal.

22. The method of claim 18, wherein the non-REM sleep stage comprises one or more of a Stage 1 sleep stage, a Stage 2 sleep stage, or a Deep Sleep sleep stage.

23. The method of claim 18, wherein detecting the non-REM sleep stage comprises:
determining a frequency characteristic of the brain signal, and
determining a sleep stage of the patient based on the determined frequency characteristic of the brain signal.

24. The method of claim 18, further comprising:
determining a first sleep stage determination based on the brain signal;
receiving a physiological signal indicative of a physiological parameter of the patient, wherein the physiological signal is different than the brain signal; and determining a second sleep stage determination based on the physiological signal, wherein detecting the non-REM sleep stage of the patient comprises detecting the non-REM sleep stage based on the first and second sleep stage determinations.

25. The method of claim 18, wherein receiving the brain signal comprises receiving the brain signal from the sensing module that is separate from the implantable medical device.

26. The method of claim 18, wherein the therapy comprises electrical stimulation therapy.

27. The method of claim 18, wherein the therapy comprises delivery of a therapeutic agent.

28. The method of claim 18, further comprising:
determining, by the processor, the patient is in at least one of an awake state, a first sleep stage or a second sleep stage based on a frequency characteristic of the brain signal; and
controlling, by the processor, the therapy module to activate therapy delivery to the patient in response to determining the patient is in the awake state or the first sleep stage, and deactivate or decrease an intensity of therapy delivered to the patient in response to determining the patient is in the second sleep stage.

29. The method of claim 28, wherein the first sleep stage comprises at least one of a Stage 1 or rapid eye movement sleep stage and the second sleep stage comprises at least one of a Deep Sleep or Stage 2 sleep stage.

30. The method of claim 18, further comprising:
detecting, by the processor, a REM sleep stage of the patient based on the brain signal and
controlling, by the processor, the therapy module to deliver therapy that minimizes movement of the patient relative to the patient state in which the patient is not receiving the therapy in response to detecting the REM sleep stage.

31. The method of claim 18, further comprising:
determining, by the processor, a physiological parameter of the patient, wherein the physiological parameter comprises at least one of an activity level, posture, heart rate, electrocardiogram morphology or core temperature; and
determining whether the patient is in a sleep state based on the physiological parameter of the patient.

32. The method of claim 18, wherein controlling, by the processor, the therapy module to deliver therapy configured to improve performance of one or more motor tasks by the patient relative to a patient state in which the patient is not receiving the therapy comprises controlling, by the processor, the therapy module to deliver therapy configured to improve performance of one or more of initiating movement or maintaining movement by the patient relative to a patient state in which the patient is not receiving the therapy.

33. A system comprising:
an implantable medical device comprising a therapy module;
means for detecting a non-REM sleep stage of a patient based on a brain signal sensed via external electrodes located external to the patient; and
means for controlling the therapy module of the implantable medical device to deliver therapy to the patient configured to improve performance of one or more motor tasks by the patient relative to a patient state in which the patient is not receiving the therapy in response to detection of the non-REM sleep stage by the means for detecting.

34. The system of claim 33, further comprising means for detecting a REM sleep stage of the patient based on the brain signal, wherein the means for controlling controls the means for delivering therapy to deliver therapy that minimizes movement of the patient relative to the patient state in which the patient is not receiving the therapy in response to detection of the REM sleep stage by the means for detecting.

35. A non-transitory computer-readable medium comprising instructions that cause a processor to:
receive a brain signal of a patient sensed by a sensing module via external electrodes electrically coupled to the sensing module, wherein the external electrodes are located external to the patient;
detect a non-REM sleep stage of the patient based on the brain signal; and
in response to detecting the non-REM sleep stage, control a therapy module of an implantable medical device to deliver therapy configured to improve performance of one or more motor tasks by the patient relative to a patient state in which the patient is not receiving the therapy.

36. The non-transitory computer-readable medium of claim 35, further comprising instructions that cause the processor to detect a REM sleep stage of the patient based on the brain signal, and, in response to detecting the REM sleep stage, control the therapy module to deliver therapy that minimizes movement of the patient relative to the patient state in which the patient is not receiving the therapy.

* * * * *